US008927117B2

(12) United States Patent
Buesing et al.

(10) Patent No.: US 8,927,117 B2
(45) Date of Patent: Jan. 6, 2015

(54) MATERIALS FOR ORGANIC ELECTROLUMINESCENCE DEVICE

(75) Inventors: Arne Buesing, Frankfurt am Main (DE); Holger Heil, Frankfurt am Main (DE); Philipp Stoessel, Frankfurt am Main (DE)

(73) Assignee: Merck Patent GmbH (DE)

( * ) Notice: Subject to any disclaimer, the term of this patent is extended or adjusted under 35 U.S.C. 154(b) by 462 days.

(21) Appl. No.: 12/937,794

(22) PCT Filed: Mar. 17, 2009

(86) PCT No.: PCT/EP2009/001938
§ 371 (c)(1),
(2), (4) Date: Oct. 14, 2010

(87) PCT Pub. No.: WO2009/127307
PCT Pub. Date: Oct. 22, 2009

(65) Prior Publication Data
US 2011/0037063 A1    Feb. 17, 2011

(30) Foreign Application Priority Data

Apr. 14, 2008   (DE) .................... 10 2008 018 670

(51) Int. Cl.
| H01L 51/50 | (2006.01) |
| H05B 33/14 | (2006.01) |
| C07D 213/38 | (2006.01) |
| H01L 51/00 | (2006.01) |
| C07D 235/08 | (2006.01) |
| C07D 307/80 | (2006.01) |
| C07D 333/18 | (2006.01) |
| C07D 317/72 | (2006.01) |
| C09K 11/06 | (2006.01) |
| C07D 335/04 | (2006.01) |
| C07C 13/62 | (2006.01) |
| C07D 307/94 | (2006.01) |
| C07D 471/04 | (2006.01) |
| C07D 495/04 | (2006.01) |

(52) U.S. Cl.
CPC ......... C09K 11/06 (2013.01); *C09K 2211/1088* (2013.01); *C09K 2211/1092* (2013.01); H05B 33/14 (2013.01); *C09K 2211/1011* (2013.01); C07D 213/38 (2013.01); *H01L 51/5048* (2013.01); *C09K 2211/1014* (2013.01); H01L 51/0056 (2013.01); *C09K 2211/1044* (2013.01); *Y02E 10/549* (2013.01); C07D 235/08 (2013.01); *C09K 2211/1007* (2013.01); C07D 307/80 (2013.01); *C09K 2211/1029* (2013.01); C07D 333/18 (2013.01); C07D 317/72 (2013.01); *H01L 51/5012* (2013.01); C07D 335/04 (2013.01); C07C 13/62 (2013.01); *H01L 51/0055* (2013.01); C07D 307/94 (2013.01); C07D 471/04 (2013.01); C07D 495/04 (2013.01); *C09K 2211/1022* (2013.01); *Y10S 428/917* (2013.01)

USPC ........... 428/690; 428/917; 313/504; 313/505; 313/506; 257/40; 257/E51.05; 257/E51.026; 257/E51.032; 585/27; 548/304.1; 548/418; 548/440; 548/444; 546/19; 546/79; 546/81; 546/101

(58) Field of Classification Search
USPC ............. 428/690, 917; 313/504, 506; 257/40, 257/E51.05, E51.026, E51.032; 585/27
See application file for complete search history.

(56) References Cited

U.S. PATENT DOCUMENTS

| 5,942,340 | A  | * | 8/1999  | Hu et al. ..................... 428/690 |
| 7,049,011 | B2 | * | 5/2006  | Ebisawa et al. ............... 428/690 |
| 2002/0132134 | A1 | | 9/2002 | Hu et al. |
| 2004/0131881 | A1 | * | 7/2004 | Zheng et al. ................. 428/690 |
| 2008/0297037 | A1 | | 12/2008 | Vestweber et al. |
| 2008/0303423 | A1 | | 12/2008 | Heil et al. |
| 2009/0159874 | A1 | | 6/2009 | Vestweber et al. |
| 2009/0261717 | A1 | | 10/2009 | Buesing et al. |
| 2010/0013381 | A1 | | 1/2010 | Stoessel et al. |

FOREIGN PATENT DOCUMENTS

| DE | 102004031000 A1 | 1/2006 |
| DE | 102005058557 A1 | 6/2007 |
| DE | 102006031990 A1 | 1/2008 |
| DE | 102006035035 A1 | 1/2008 |

* cited by examiner

Primary Examiner — Gregory Clark
(74) Attorney, Agent, or Firm — Drinker Biddle & Reath LLP

(57) ABSTRACT

The present invention relates to a compound of the formula (1) and (2)

formula (1)

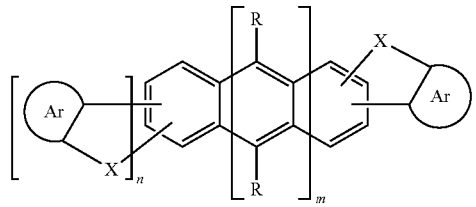

formula (2)

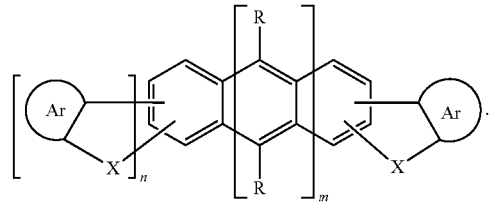

The invention further relates to a process to produce the compound. The invention additionally relates and an electronic device containing the compound of the formula (1) or (2). The electronic device can be an organic electroluminescence devices, particularly a blue emitting device, in which compounds are used as host materials or dopants in the emitting layer and/or as hole transport materials and/or as electron transport materials.

16 Claims, 1 Drawing Sheet

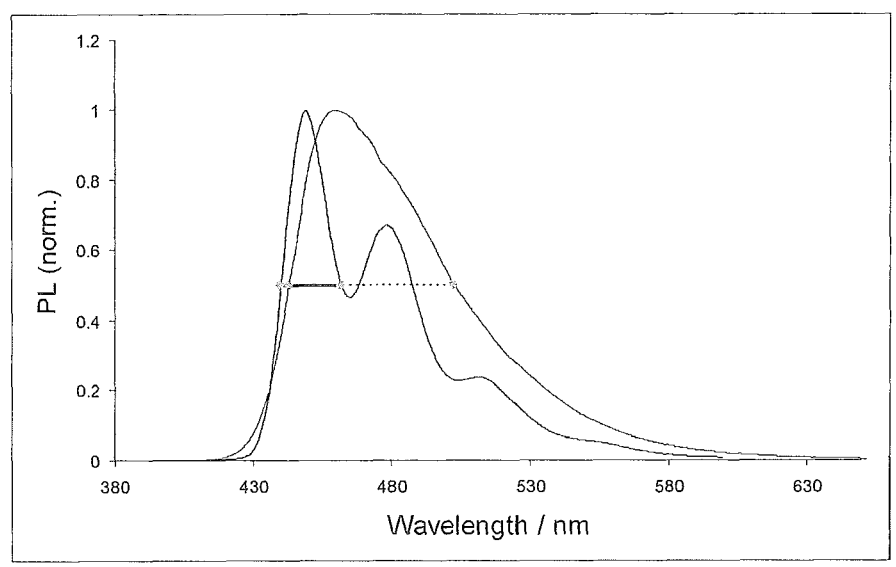

MATERIALS FOR ORGANIC ELECTROLUMINESCENCE DEVICE

CROSS-REFERENCE TO RELATED APPLICATIONS

This application is a national stage application (under 35 U.S.C. §371) of PCT/EP2009/001938, filed Mar. 17, 2009, which claims benefit of German application 10 2008 018 670.8, filed Apr. 14, 2008.

BACKGROUND OF THE INVENTION

The present invention relates to organic semiconductors and to the use thereof in organic electronic devices.

Organic semiconductors are being developed for a number of electronic applications of different types. The structure of organic electroluminescent devices (OLEDs) in which these organic semiconductors are employed as functional materials is described, for example, in U.S. Pat. Nos. 4,539,507, 5,151,629, EP 0676461 and WO 98/27136. However, further improvements are still desirable to enable these devices to be used for high-quality and long-lived displays. Thus, in particular, the lifetime and the efficiency of blue-emitting organic electroluminescent devices currently still represent a problem for which there is still a need for improvement. Furthermore, it is necessary for the compounds to have high thermal stability and a high glass-transition temperature and to be sublimable without decomposition. In particular for use at elevated temperature, a high glass-transition temperature is essential in order to achieve long lifetimes.

For fluorescent OLEDs, principally condensed aromatic compounds, in particular anthracene derivatives, are used in accordance with the prior art as host materials, especially for blue-emitting electroluminescent devices, for example 9,10-bis(2-naphthyl)anthracene (U.S. Pat. No. 5,935,721). WO 03/095445 and CN 1362464 disclose 9,10-bis(1-naphthyl) anthracene derivatives for use in OLEDs. Further anthracene derivatives are disclosed in WO 01/076323, in WO 01/021729, in WO 04/013073, in WO 04/018588, in WO 03/087023 or in WO 04/018587. Host materials based on aryl-substituted pyrenes and chrysenes are disclosed in WO 04/016575, host materials based on benzanthracenes are disclosed in WO 08/145,239. For high-quality applications, it is desirable to have available improved host materials. The same also applies to host materials for green- and red-fluorescing dopants.

Prior art which may be mentioned in the case of blue-emitting compounds is the use of arylvinylamines (for example WO 04/013073, WO 04/016575, WO 04/018587). However, these compounds are thermally unstable and cannot be evaporated without decomposition, which requires high technical complexity for OLED production and thus represents a technical disadvantage. It is therefore necessary for high-quality applications to have available improved emitters, particularly with respect to device and sublimation stability and emission colour. It would furthermore be advantageous to have available emitters which have a narrower emission spectrum.

There thus continues to be a demand for improved materials, in particular host materials for fluorescent emitters, especially for green- and red-fluorescing emitters, but also for blue-fluorescing emitters, and fluorescent materials which are thermally stable, which result in good efficiencies and at the same time in long lifetimes in organic electronic devices, which give reproducible results during production and operation of the device and which are readily accessible synthetically. Further improvements are also necessary in the case of hole- and electron-transport materials.

Surprisingly, it has been found that anthracene derivatives which are substituted in the 9- or 9,10-position and onto which an indeno group is condensed in the 1,2-position or 2,3-position or 3,4-position and/or in the 5,6-position or 6,7-position or 7,8-position are very highly suitable for use in organic electroluminescent devices. This likewise applies if corresponding heterocyclic groups, such as, for example, indolo groups or benzothienyl groups, are condensed on instead of the indeno group. These compounds enable an increase in the efficiency and especially the lifetime of the organic electronic device compared with materials in accordance with the prior art. This applies, in particular, to blue-fluorescing devices. Furthermore, these compounds have high thermal stability. In general, these materials are very highly suitable for use in organic electronic devices since they have a high glass-transition temperature. The present invention therefore relates to these materials and to the use thereof in organic electronic devices.

The closest prior art can be regarded as US 2002/132134. This discloses condensed aromatic compounds onto which two aryl-substituted indeno groups are condensed. However, these compounds have a large Stokes shift, which is possibly caused by the degrees of rotational freedom of the aryl substituents. The compounds disclosed in US 2002/132134 are therefore not suitable as host material for deep-blue emitters. There is therefore still a need for improvement here. It would furthermore be advantageous to have available compounds which have a narrower emission spectrum.

Furthermore, 9,10-diphenylanthracene is known as emitter. Although this has a fluorescence quantum efficiency of 100% (H. Du et al., *Photochemistry and Photobiology* 1998, 68, 141-142), the emission is, however, too far in the blue region, meaning that this compound cannot be used as blue emitter.

For clarity, the structure and numbering of anthracene are shown below:

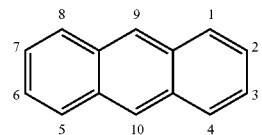

BRIEF SUMMARY OF THE INVENTION

The invention therefore relates to compounds of the formulae (1) and (2):

formula (1)

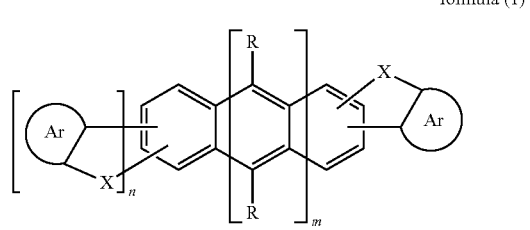

-continued

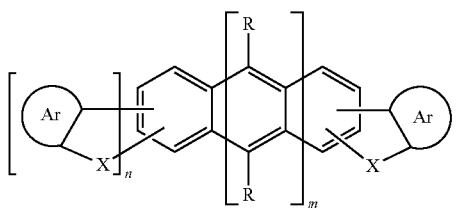

formula (2)

in which one or more unsubstituted carbon atoms in the anthracene unit may also be replaced by nitrogen; furthermore, the following applies to the symbols and indices used:

X is on each occurrence, identically or differently, a divalent bridge selected from $B(R^1)$, $C(R^1)_2$, $Si(R^1)_2$, $C=O$, $C=NR^1$, $C=C(R^1)_2$, O, S, $S=O$, $SO_2$, $N(R^1)$, $P(R^1)$ and $P(=O)R^1$;

Ar is on each occurrence, identically or differently, an aryl group having 6 to 40 C atoms or a heteroaryl group having 2 to 40 C atoms, each of which may be substituted by one or more radicals $R^2$;

$R^1$ is on each occurrence, identically or differently, H, D, F, Cl, Br, I, CHO, $N(R^3)_2$, $N(Ar^1)_2$, $C(=O)Ar^1$, $P(=O)(Ar^1)_2$, $S(=O)Ar^1$, $S(=O)_2Ar^1$, $CR^3=CR^3Ar^1$, CN, $NO_2$, $Si(R^3)_3$, $B(OR^3)_2$, $OSO_2R^3$, a straight-chain alkyl, alkenyl, alkynyl, alkoxy or thioalkoxy group having 1 to 40 C atoms or a branched or cyclic alkyl, alkenyl, alkynyl, alkoxy or thioalkoxy group having 3 to 40 C atoms, each of which may be substituted by one or more radicals $R^3$, where one or more non-adjacent $CH_2$ groups may be replaced by $R^3C=CR^3$, $C\equiv C$, $Si(R^3)_2$, $Ge(R^3)_2$, $Sn(R^3)_2$, $C=O$, $C=S$, $C=Se$, $C=NR^2$, $P(=O)(R^3)$, SO, $SO_2$, $NR^3$, O, S or $CONR^3$ and where one or more H atoms may be replaced by D, F, Cl, Br, I, CN or $NO_2$, or an aromatic or heteroaromatic ring system having 5 to 40 aromatic ring atoms, each of which may be substituted by one or more radicals $R^2$, or an aryloxy or heteroaryloxy group having 5 to 40 aromatic ring atoms, which may be substituted by one or more radicals $R^2$, or a combination of these systems; two or more adjacent substituents $R^1$ here may also form a mono- or polycyclic, aliphatic or aromatic ring system with one another;

R is on each occurrence, identically or differently, $R^1$, with the proviso that at least one substituent R is not equal to H;

$Ar^1$ is on each occurrence, identically or differently, an aromatic or heteroaromatic ring system having 5 to 30 aromatic ring atoms, which may be substituted by one or more radicals $R^3$; two radicals Ar here which are bonded to the same nitrogen or phosphorus atom may also be linked to one another by a single bond or a bridge selected from $B(R^3)$, $C(R^3)_2$, $Si(R^3)_2$, $C=O$, $C=NR^3$, $C=C(R^3)_2$, O, S, $S=O$, $SO_2$, $N(R^3)$, $P(R^3)$ and $P(=O)R^3$;

$R^2$ is on each occurrence, identically or differently, H, D, F, Cl, Br, I, CHO, $N(R^3)_2$, $N(Ar^1)_2$, $C(=O)Ar^1$, $P(=O)(Ar^1)_2$, $S(=O)Ar^1$, $S(=O)_2Ar^1$, $CR^3=CR^3Ar^1$, CN, $NO_2$, $Si(R^3)_3$, $B(OR^3)_2$, $OSO_2R^3$, a straight-chain alkyl, alkenyl, alkynyl, alkoxy or thioalkoxy group having 1 to 40 C atoms or a branched or cyclic alkyl, alkenyl, alkynyl, alkoxy or thioalkoxy group having 3 to 40 C atoms, each of which may be substituted by one or more radicals $R^3$, where one or more non-adjacent $CH_2$ groups may be replaced by $R^3C=CR^3$, $C\equiv C$, $Si(R^3)_2$, $Ge(R^3)_2$, $Sn(R^3)_2$, $C=O$, $C=S$, $C=Se$, $C=NR^2$, $P(=O)(R^3)$, SO, $SO_2$, $NR^3$, O, S or $CONR^3$ and where one or more H atoms may be replaced by F, Cl, Br, I, CN or $NO_2$, or a combination of these systems; two or more adjacent substituents $R^2$ here may also form a mono- or polycyclic, aliphatic or aromatic ring system with one another;

$R^3$ is on each occurrence, identically or differently, H, D, F or an aliphatic, aromatic and/or heteroaromatic hydrocarbon radical having 1 to 20 C atoms, in which, in addition, H atoms may be replaced by F; two or more adjacent substituents $R^2$ here may also form a mono- or polycyclic, aliphatic or aromatic ring system with one another;

m is 1, 2 or 3;
n is 0 or 1.

BRIEF DESCRIPTION OF THE FIGURE

FIG. 1 illustrates the significantly narrower half-value width of the emission peak.

DETAILED DESCRIPTION OF THE INVENTION

In the structures of the formulae (1) and (2), the group Ar is bonded to the anthracene via a carbon atom and the group X is bonded to an adjacent carbon atom of the group Ar and to an adjacent carbon atom of the anthracene. Analogously to indenofluorene, cis- and trans-diindenoanthracene derivatives and corresponding derivatives with other condensed-on groups are also possible for n=1, where structures of the formula (1) result in trans-derivatives and structures of the formula (2) result in cis-derivatives.

The compounds of the formula (1) preferably have a glass-transition temperature $T_G$ of greater than 70° C., particularly preferably greater than 100° C., very particularly preferably greater than 130° C.

For the purposes of this invention, an aryl group contains 6 to 40 C atoms; for the purposes of this invention, a heteroaryl group contains 2 to 40 C atoms and at least one heteroatom, with the proviso that the sum of C atoms and heteroatoms is at least 5. The heteroatoms are preferably selected from N, O and/or S. An aryl group or heteroaryl group here is taken to mean either a single aromatic ring, i.e. benzene, or a single heteroaromatic ring, for example pyridine, pyrimidine, thiophene, etc., or a condensed aryl or heteroaryl group, for example naphthalene, anthracene, pyrene, quinoline, isoquinoline, etc.

For the purposes of this invention, an aromatic ring system contains 6 to 40 C atoms in the ring system. For the purposes of this invention, a heteroaromatic ring system contains 2 to 40 C atoms and at least one heteroatom in the ring system, with the proviso that the sum of C atoms and heteroatoms is at least 5. The heteroatoms are preferably selected from N, O and/or S. For the purposes of this invention, an aromatic or heteroaromatic ring system is intended to be taken to mean a system which does not necessarily contain only aryl or heteroaryl groups, but instead in which a plurality of aryl or heteroaryl groups may also be interrupted by a short non-aromatic unit (preferably less than 10% of the atoms other than H), such as, for example, an $sp^3$-hybridised C, N or O atom. Thus, for example, systems such as 9,9'-spirobifluorene, 9,9-diarylfluorene, triarylamine, diaryl ether, stilbene, benzophenone, etc., are also intended to be taken to mean aromatic ring systems for the purposes of this invention. An aromatic or heteroaromatic ring system is likewise taken to mean systems in which a plurality of aryl or heteroaryl groups are linked to one another by single bonds, for example biphenyl, terphenyl or bipyridine.

For the purposes of the present invention, a $C_1$- to $C_{40}$-alkyl group, in which, in addition, individual H atoms or $CH_2$ groups may be substituted by the above-mentioned groups, is particularly preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl or 2,2,2-trifluoroethyl. For the purposes of this invention, an alkenyl group is preferably taken to mean the radicals ethenyl, propenyl, butenyl, pentenyl, cyclopentenyl, hexenyl, cyclohexenyl, heptenyl, cycloheptenyl, octenyl or cyclooctenyl. For the purposes of this invention, an alkynyl group is preferably taken to mean ethynyl, propynyl, butynyl, pentynyl, hexynyl, heptenyl or octynyl. A $C_1$- to $C_{40}$-alkoxy group is particularly preferably taken to mean methoxy, trifluoromethoxy, ethoxy, n-propoxy, i-propoxy, n-butoxy, i-butoxy, s-butoxy, t-butoxy or 2-methylbutoxy. An aromatic or heteroaromatic ring system having 5-40 aromatic ring atoms, which may also in each case be substituted by the above-mentioned radicals R and which may be linked to the aromatic or heteroaromatic ring system via any desired positions, is taken to mean, in particular, groups derived from benzene, naphthalene, anthracene, phenanthrene, benzanthracene, pyrene, chrysene, perylene, fluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

A preferred embodiment of the compounds of the formulae (1) and (2) are the compounds of the formulae (3) to (15):

formula (3)

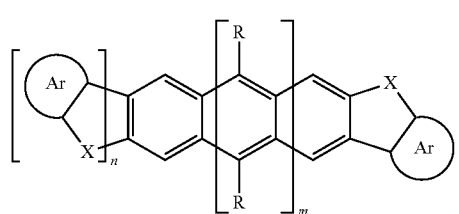

formula (4)

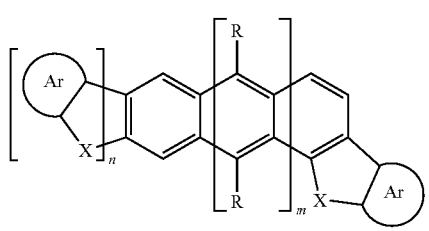

formula (5)

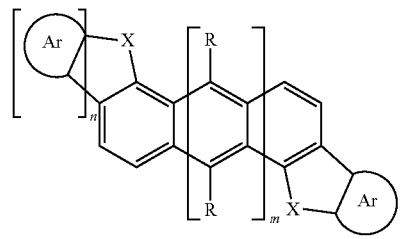

formula (6)

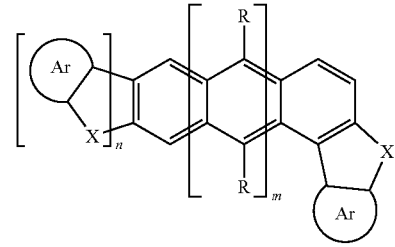

formula (7)

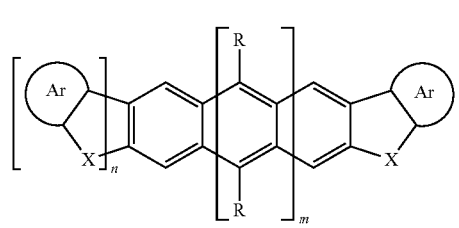

formula (8)

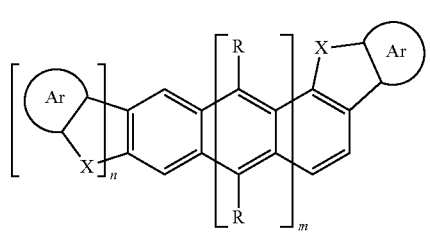

formula (9)

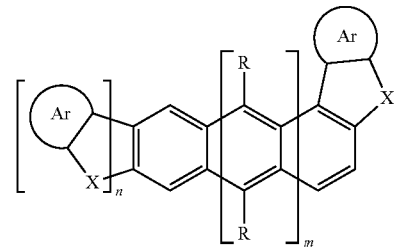

formula (10)

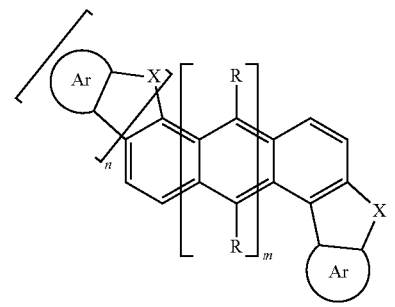

-continued formula (11)
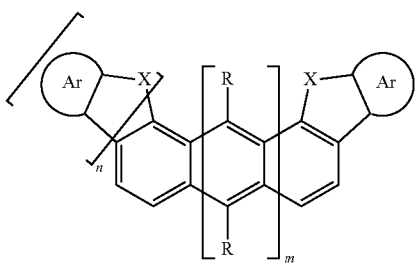

formula (12)
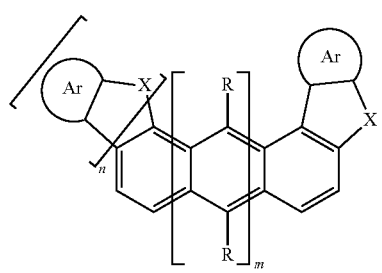

formula (13)
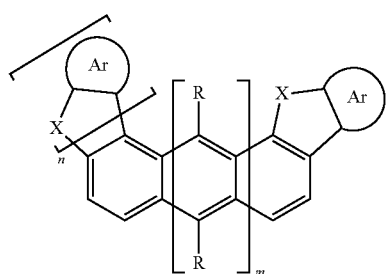

formula (14)
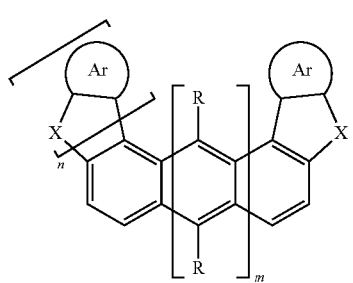

formula (15)
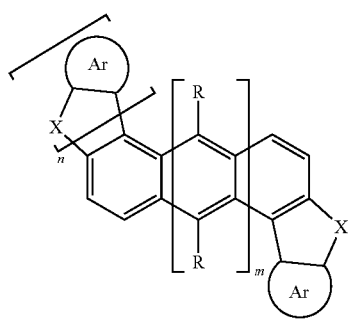

where one or more unsubstituted carbon atoms in the anthracene unit may also be replaced by nitrogen and where the symbols and indices have the meanings indicated above.

In a preferred embodiment of the invention, the symbol Ar stands, identically or differently on each occurrence, for an aryl group having 6 to 16 C atoms, particularly preferably having 6 to 14 C atoms, in particular having 6 to 10 C atoms, or for a heteroaryl group having 2 to 16 C atoms, particularly preferably having 3 to 13 C atoms, in particular having 4 to 9 C atoms, each of which may be substituted by one or more radicals $R^2$. In a very particularly preferred embodiment of the invention, the symbol Ar stands, identically or differently on each occurrence, for benzene, naphthalene, thiophene, pyrrole, furan, pyridine, pyrimidine, pyrazine, pyridazine, quinoline, quinoxaline, triazine, triazole, imidazole, benzimidazole, benzothiophene, indole or benzofuran, in particular for benzene, naphthalene or thiophene.

In a preferred embodiment of the invention, the two groups Ar are selected identically for n=1. This is due to the improved synthetic accessibility of the compounds.

Of the compounds of the formulae (3) to (15), the compounds of the formulae (3), (4) and (5) are particularly preferred since they can be synthesised starting from synthetically readily accessible 2-bromoanthraquinone for n=1 or 2,6-dibromoanthraquinone for n=2.

A particularly preferred embodiment of the compounds of the formulae (3) to (15) are the compounds of the formulae (3a) to (15a), (3b) to (15b) and (3c) to (15c):

formula (3a)
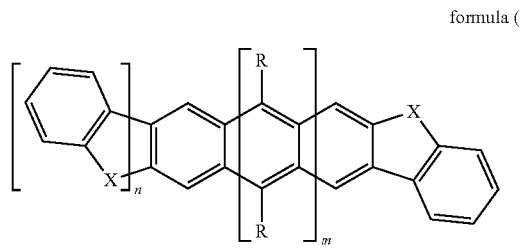

formula (4a)
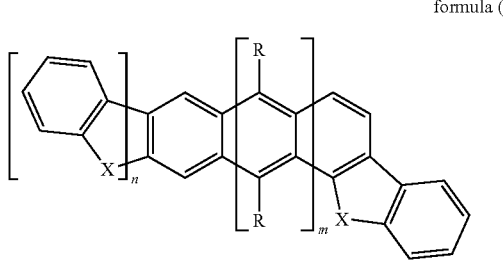

formula (5a)
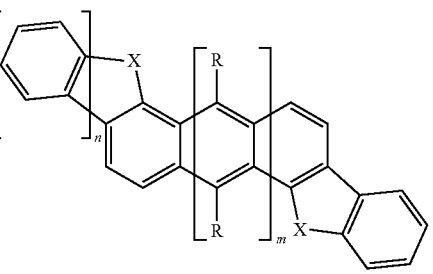

formula (6a)
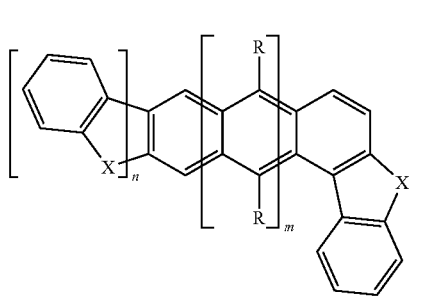

-continued
formula (7a)
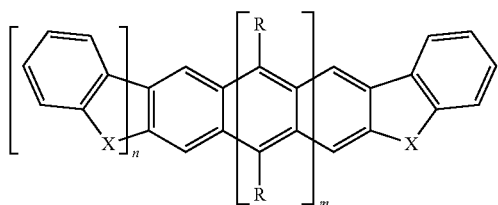
formula (8a)
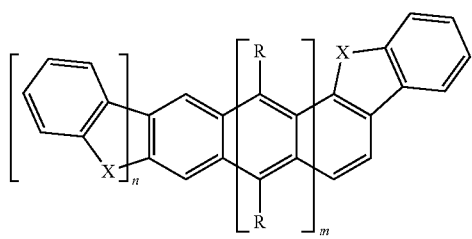
formula (9a)
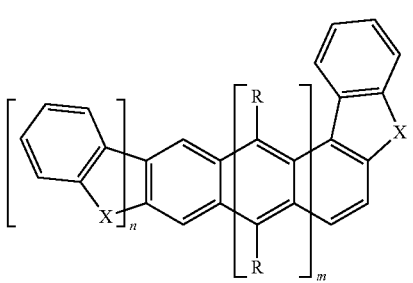
formula (10a)
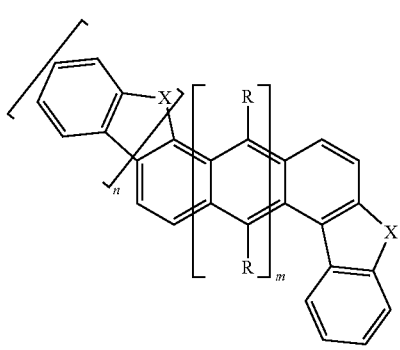
formula (11a)
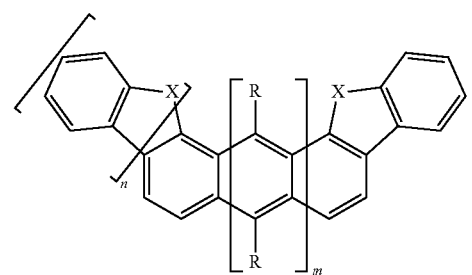
-continued
formula (12a)
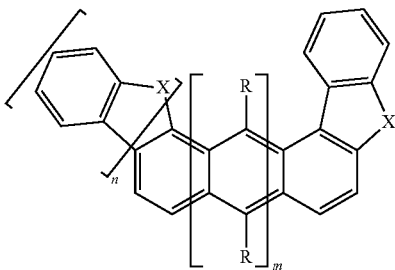
formula (13a)
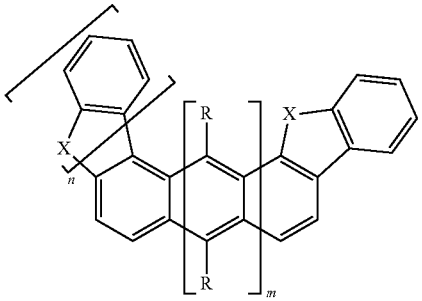
formula (14a)
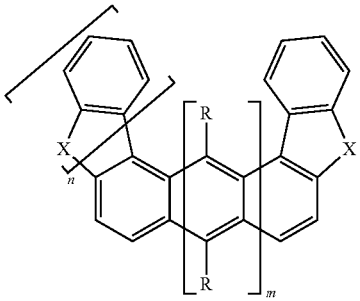
formula (15a)
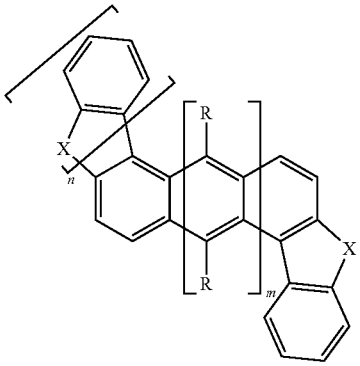
formula (3b)
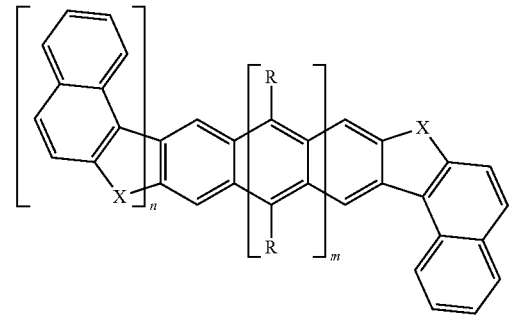

formula (4b)
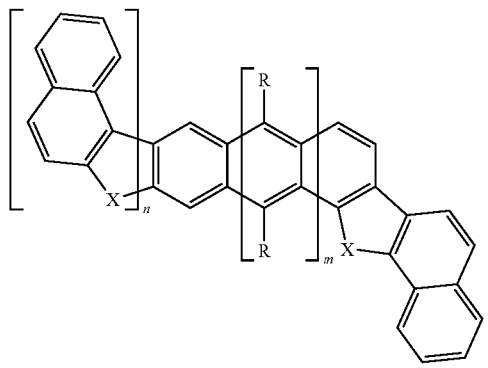
formula (5b)
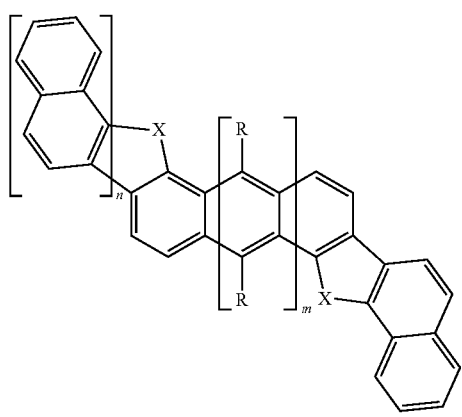
formula (6b)
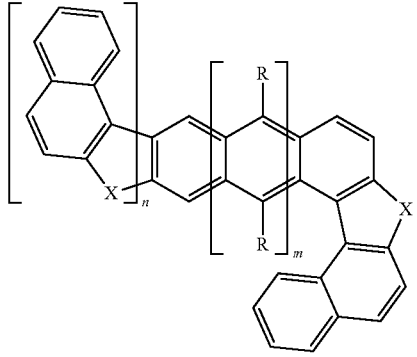
formula (7b)
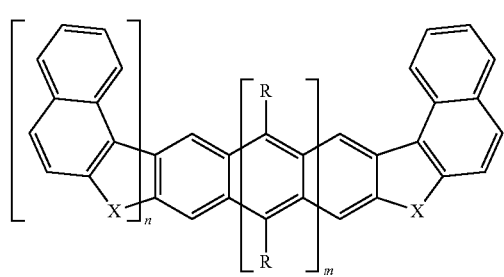
formula (8b)
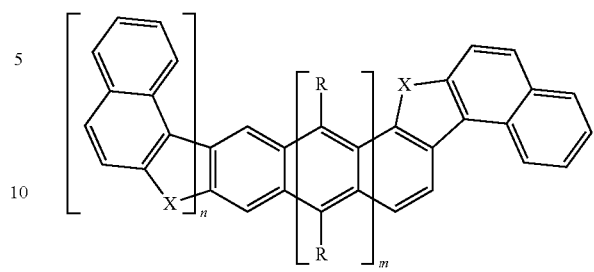
formula (9b)
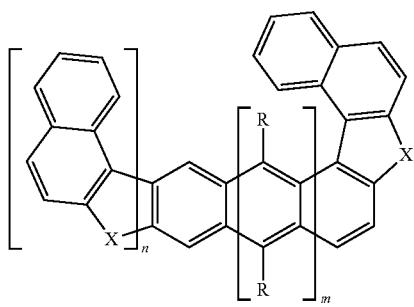
formula (10b)
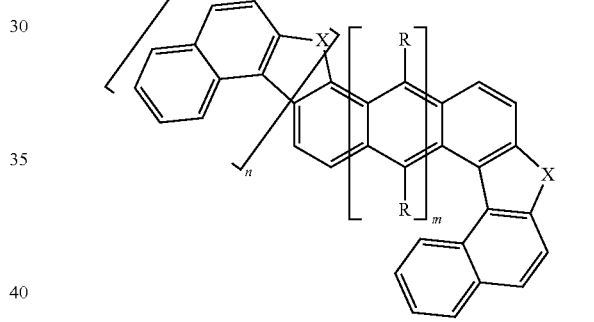
formula (11b)
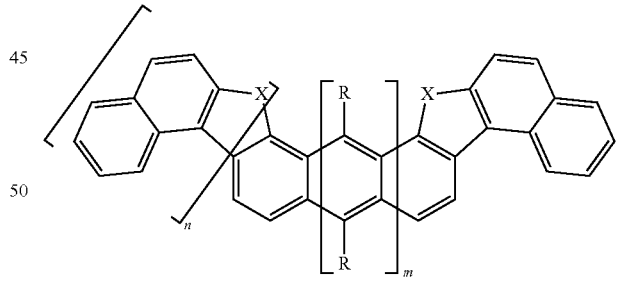
formula (12b)
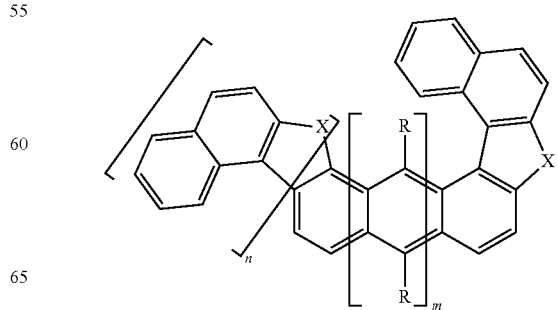

formula (13b)
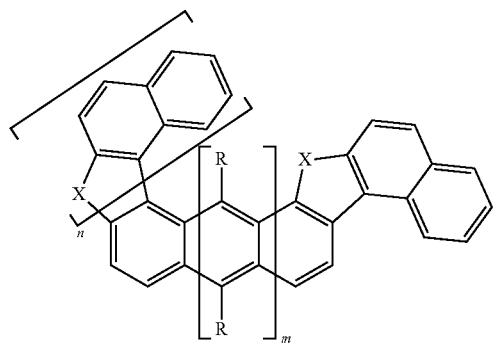
formula (14b)
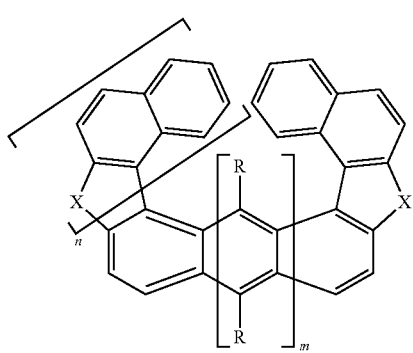
formula (15b)
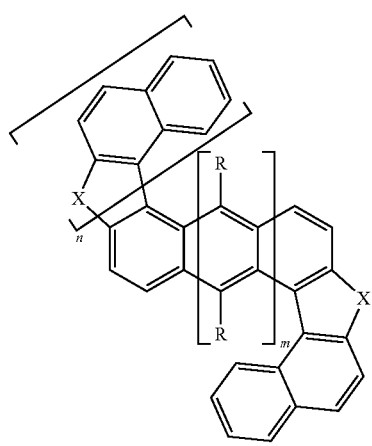
formula (3c)
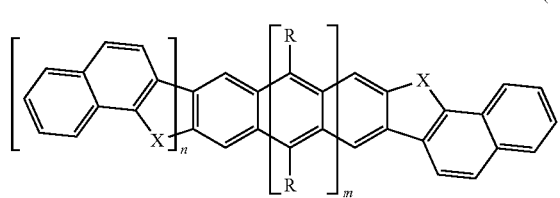
formula (4c)
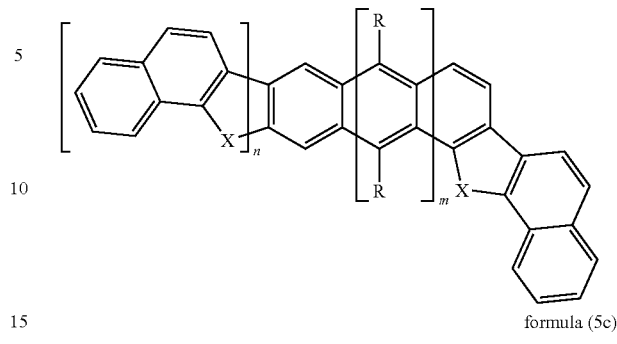
formula (5c)
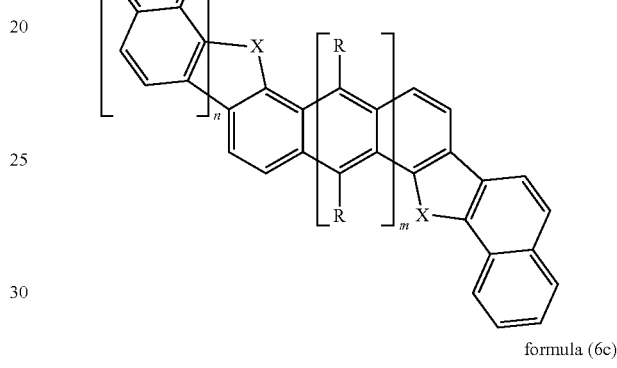
formula (6c)
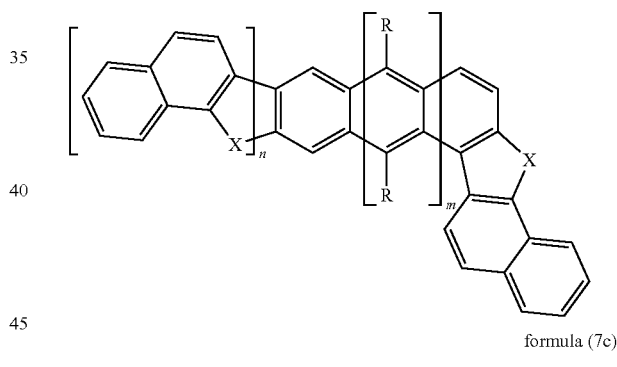
formula (7c)
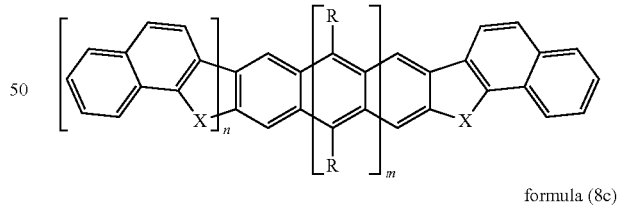
formula (8c)
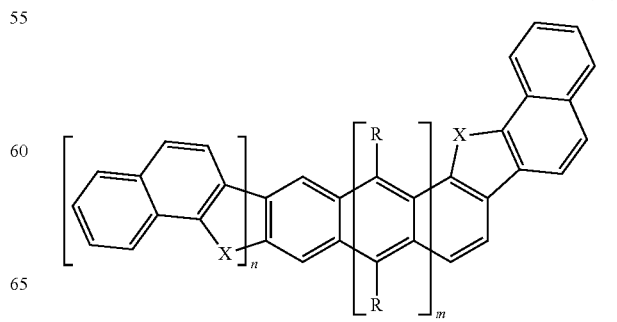

formula (9c)

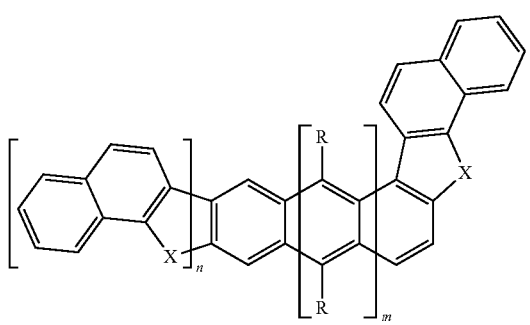

formula (10c)

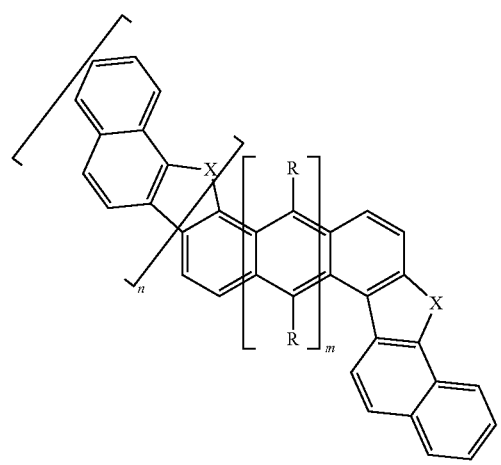

formula (11c)

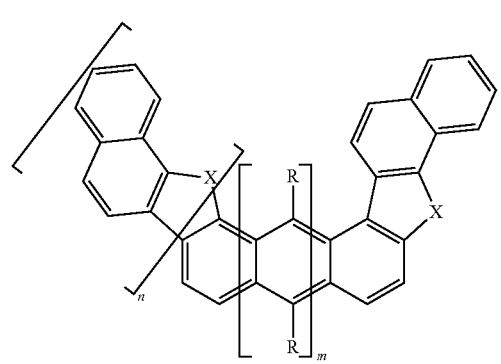

formula (12c)

formula (13c)

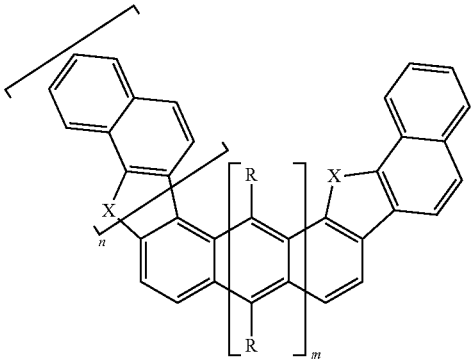

formula (14c)

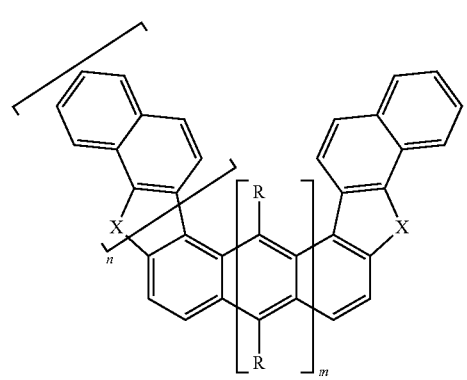

formula (15c)

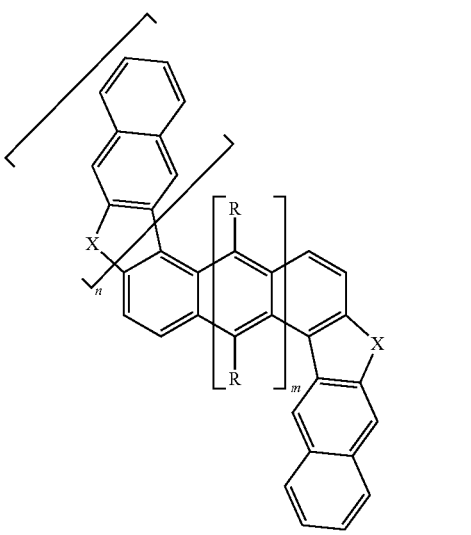

where the symbols and indices have the meanings indicated above. Particular preference is given to the compounds of the formulae (3a) to (15a) depicted above, in particular the compounds of the formulae (3a), (4a) and (5a).

In a preferred embodiment of the invention, the index m in compounds of the formulae (1) and (2) and (3) to (15) and (3a) to (15a) and (3b) to (15b) and (3c) to (15c) stands for 1 or 2, i.e. the central unit is an anthracene or a naphthacene. The index m is particularly preferably =1, i.e. the central unit is an anthracene.

In a preferred embodiment of the invention, the group X in compounds of the formulae (1) and (2) and (3) to (15) and (3a) to (15a) and (3b) to (15b) and (3c) to (15c) stands, identically or differently on each occurrence, for $C(R^1)_2$, C=O, O, S, S=O, $SO_2$, $N(R^1)$, $P(R^1)$ or $P(=O)R^1$, particularly preferably for $C(R^1)_2$, O, S or $N(R^1)$, very particularly preferably for $C(R^1)_2$. It should again be explicitly pointed out here that, for X=$C(R^1)_2$, the radicals $R^1$ may also form an aromatic or aliphatic ring system with one another. If a plurality of radicals $R^1$ on a group $C(R^1)_2$ form a ring system with one another, this results in spiro structures. The formation of spiro structures of this type through the formation of ring systems between two groups $R^1$ on $C(R^1)_2$ is a further preferred embodiment of the invention. This applies in particular if $R^1$ stands for a substituted or unsubstituted phenyl group and the two phenyl groups form a ring system together with the C atom of the bridge.

In a preferred embodiment of the invention, both groups R in compounds of the formulae (1) and (2) and (3) to (15) and (3a) to (15a) and (3b) to (15b) and (3c) to (15c) are not equal to H. The groups R in these compounds preferably stand, identically or differently on each occurrence, for Cl, Br, I, $N(Ar^1)_2$, $C(=O)Ar^1$, $P(=O)(Ar)_2$, $S(=O)Ar^1$, $S(=O)_2Ar^1$, $CR^3=CR^3Ar^1$, $B(OR^3)_2$, $OSO_2R^3$, a straight-chain alkyl or alkoxy group having 1 to 10 C atoms or a branched or cyclic alkyl or alkoxy group having 3 to 10 C atoms, each of which may be substituted by one or more radicals $R^3$, where one or more non-adjacent $CH_2$ groups may be replaced by $R^3C=CR^3$, C≡C, C=O, $P(=O)(R^3)$, SO, $SO_2$, $NR^3$, O, S or $CONR^3$ and where one or more H atoms may be replaced by F, or an aromatic or heteroaromatic ring system having 5 to 20 aromatic ring atoms, which may in each case be substituted by one or more radicals $R^2$, or an aryloxy or heteroaryloxy group having 5 to 20 aromatic ring atoms, which may be substituted by one or more radicals $R^2$, or a combination of these systems. The radical R in these compounds particularly preferably stands, identically or differently on each occurrence, for Br, I, $N(Ar^1)_2$, $C(=O)Ar^1$, $P(=O)(Ar^1)_2$, $S(=O)Ar^1$, $S(=O)_2Ar^1$, $CR^3=CR^3Ar^1$, $B(OR^3)_2$ or an aromatic or heteroaromatic ring system having 5 to 16 aromatic ring atoms, each of which may be substituted by one or more radicals $R^2$, or a combination of these systems. The groups Cl, Br, I and $OSO_2R^3$ are particularly preferred as reactive intermediates since these groups can be converted into the corresponding aryl- or diarylamino-substituted groups by standard reactions of organic chemistry, in particular by transition-metal-catalysed coupling reactions. These groups are furthermore preferred for use as monomer for polymerisation reactions. Very particularly preferred groups R are aromatic or heteroaromatic ring systems having 5 to 14 aromatic ring atoms, each of which may be substituted by one or more radicals $R^2$.

Preferred radicals $R^1$ which are bonded to the bridges X are identical or different and are selected from H, straight-chain alkyl groups having 1 to 5 C atoms or branched alkyl groups having 3 to 5 C atoms, where one or more non-adjacent $CH_2$ groups may be replaced by —$R^3C=CR^3$—, —C≡C— or —O— and where one or more H atoms may be replaced by F, or aryl groups having 6 to 16 C atoms or heteroaryl groups having 2 to 16 C atoms, each of which may be substituted by one or more radicals $R^2$, or a combination of two or three of these systems; two of the radicals $R^1$ which are bonded to the same bridge atom may also form a ring system with one another here. Particularly preferred radicals $R^1$ which are bonded to the bridges X are identical or different and are selected from methyl, ethyl, isopropyl, tert-butyl, where in each case one or more H atoms may be replaced by F, or aryl groups having 6 to 14 C atoms, which may be substituted by one or more radicals $R^2$, or a combination of two of these systems; two of the radicals $R^1$ which are bonded to the same bridge atom may also form a ring system with one another here. In the case of compounds which are processed from solution, linear or branched alkyl chains having up to 10 C atoms are also preferred.

In a further preferred embodiment of the invention, the groups Ar are unsubstituted, i.e. the symbol $R^2$ preferably stands for H.

In a further preferred embodiment of the invention, a maximum of two unsubstituted carbon atoms in the anthracene unit or the corresponding extended central aromatic unit for m>1 are replaced by nitrogen, preferably a maximum of one unsubstituted carbon atom; the central aromatic unit is particularly preferably a pure carbocycle.

If the radical R or $R^1$ stands for a group $N(Ar^1)_2$, this group is preferably selected from the groups of the formula (16) or formula (17):

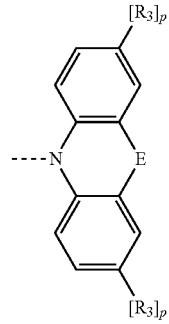

formula (16)

formula (17)

where $R^3$ has the meaning indicated above, and furthermore:

E stands for a single bond, O, S, $N(R^3)$ or $C(R^3)_2$;

$Ar^2$ is, identically or differently on each occurrence, an aryl or heteroaryl group having 5 to 20 aromatic ring atoms or a triarylamine group having 15 to 30 aromatic ring atoms, each of which may be substituted by one or more radicals $R^3$ or by Br, preferably an aryl or heteroaryl group having 6 to 14 aromatic ring atoms or a triarylamine group having 18 to 30 aromatic ring atoms, preferably having 18 to 22 aromatic ring atoms, each of which may be substituted by one or more radicals $R^3$ or by Br;

p is on each occurrence, identically or differently, 0 or 1.

$Ar^2$ particularly preferably stands, identically or differently, for phenyl, 1-naphthyl, 2-naphthyl, 2-, 3- or 4-triphenylamine, 1- or 2-naphthyldiphenylamine, which may in each case be bonded via the naphthyl or phenyl group, or 1- or 2-dinaphthylphenylamine, which may in each case be bonded via the naphthyl or phenyl group. These groups may each be substituted by one or more alkyl groups having 1 to 4 C atoms or by fluorine.

Examples of preferred compounds of the formulae (1) to (15) and (3a) to (15a) and (3b) to (15b) and (3c) to (15c) are structures (1) to (134) depicted below.

(1)
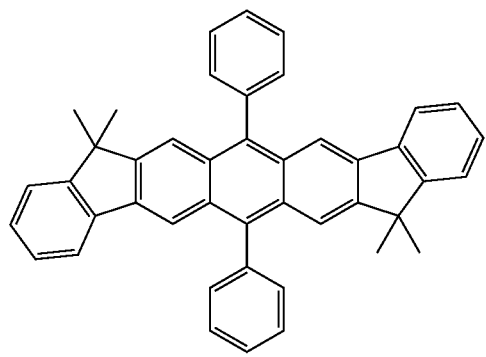
(2)
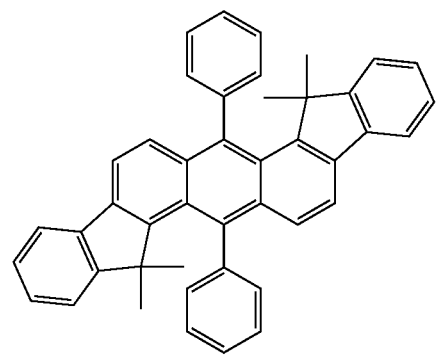
(3)
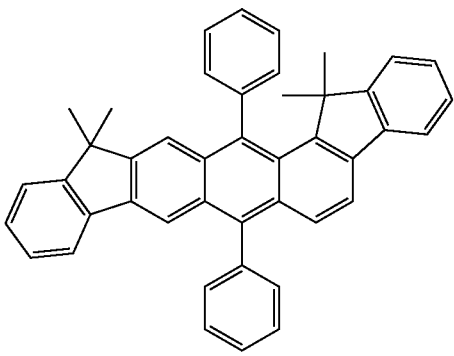
(4)
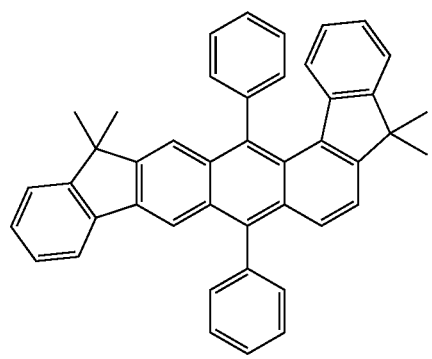
(5)
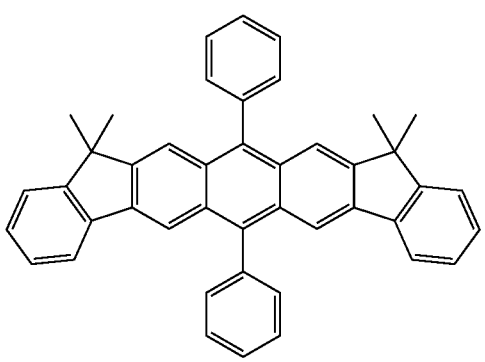
(6)
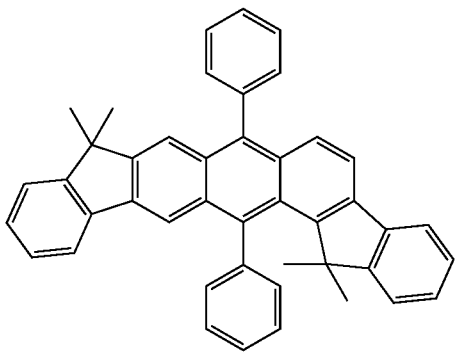
(7)
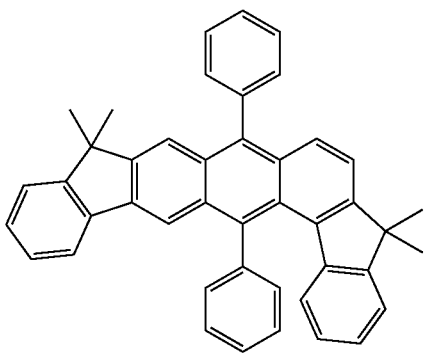
(8)
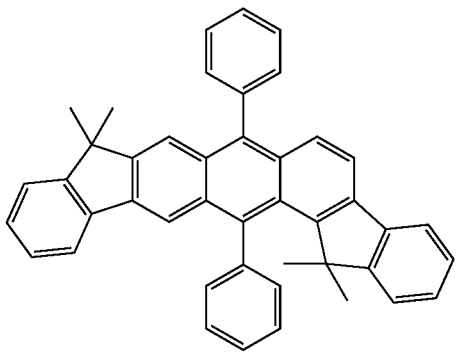

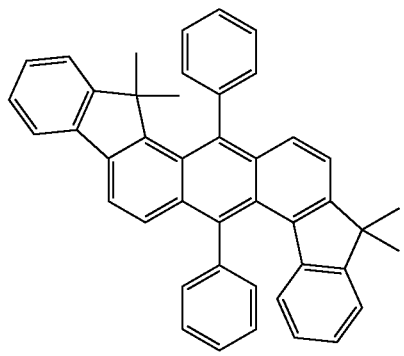
(9)
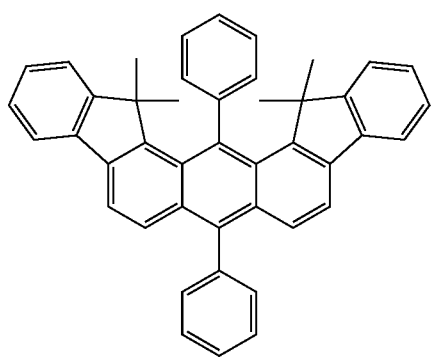
(10)
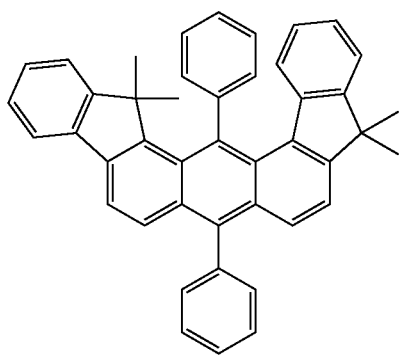
(11)
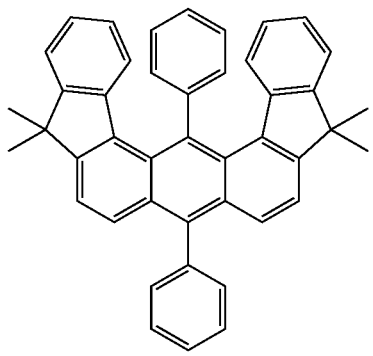
(12)
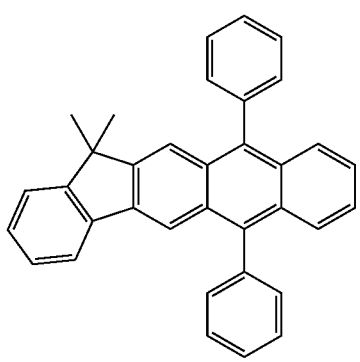
(13)
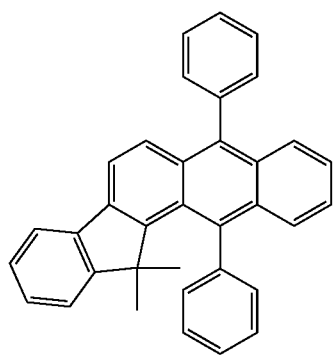
(14)
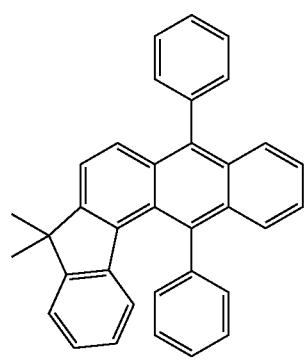
(15)
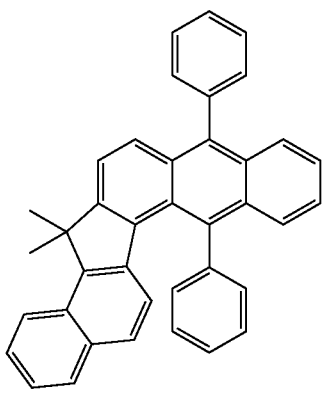
(16)

-continued
(17)
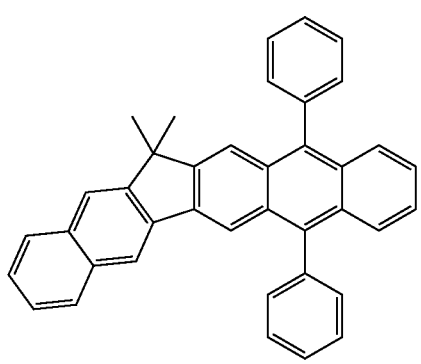
(18)
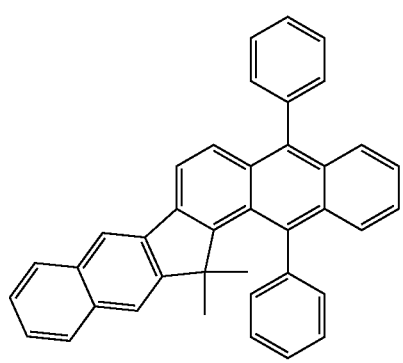
(19)
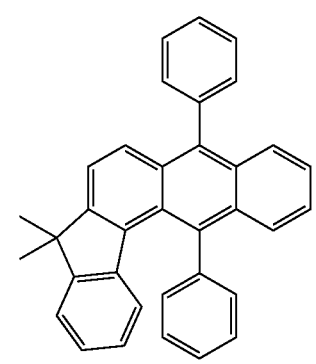
(20)
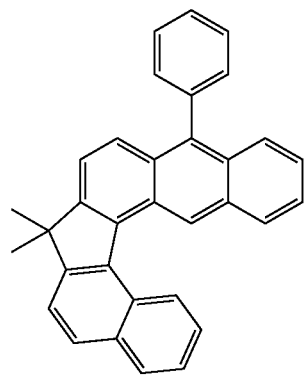
-continued
(21)
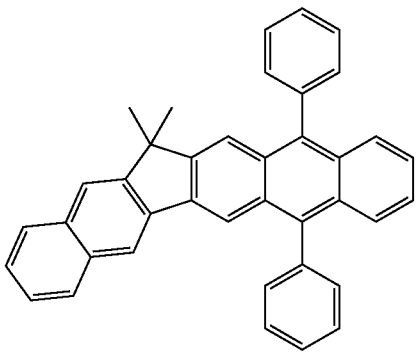
(22)
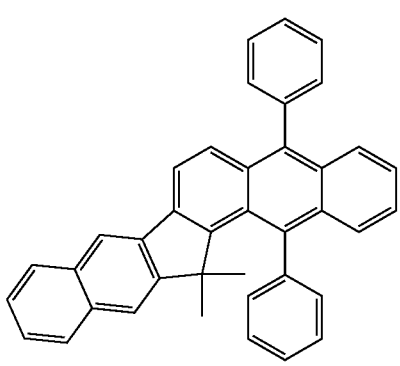
(23)
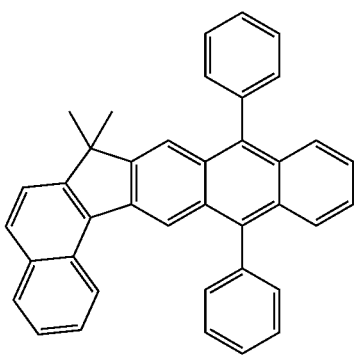
(24)
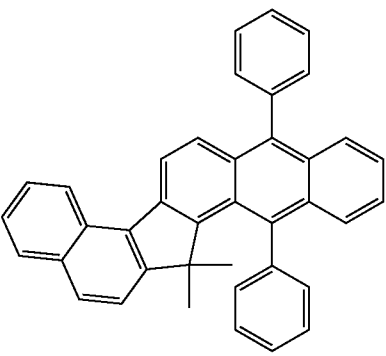

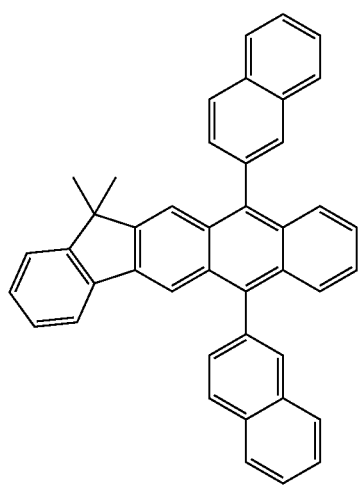
(25)
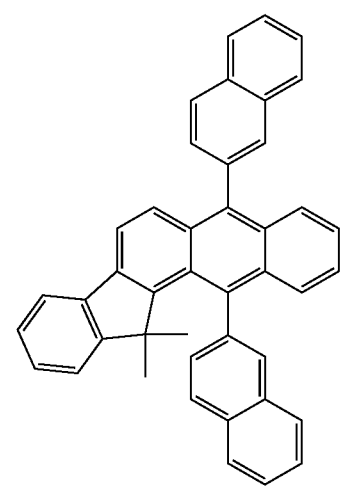
(26)
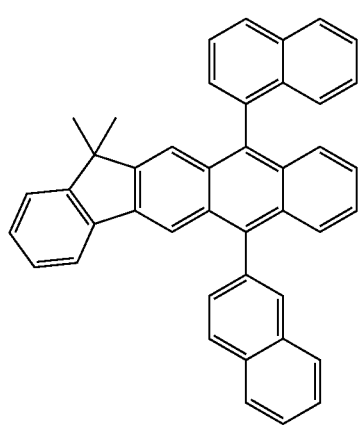
(27)
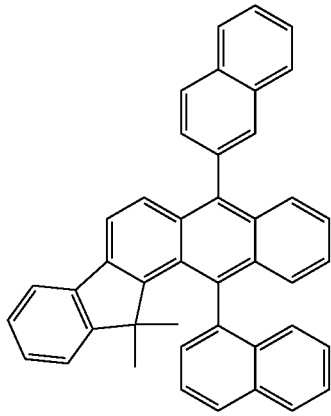
(28)
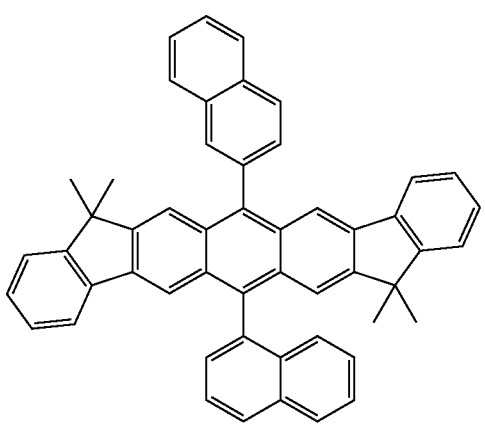
(29)
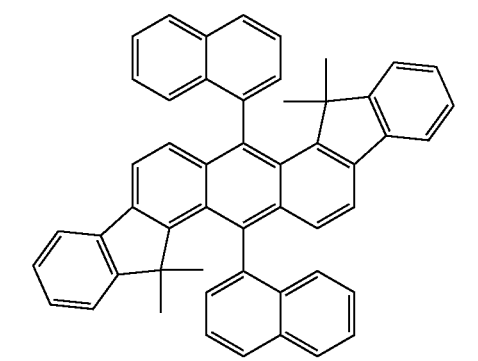
(30)
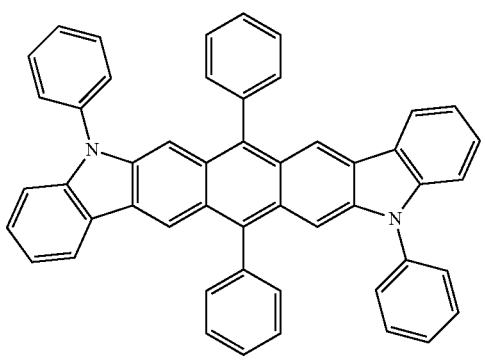
(31)

-continued
(32)
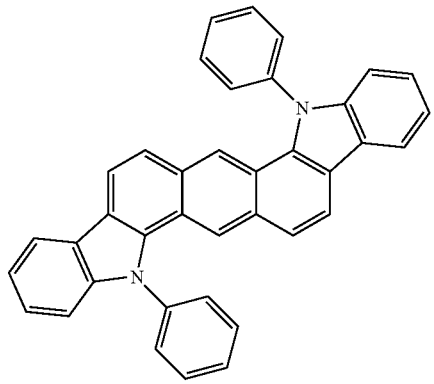
(33)
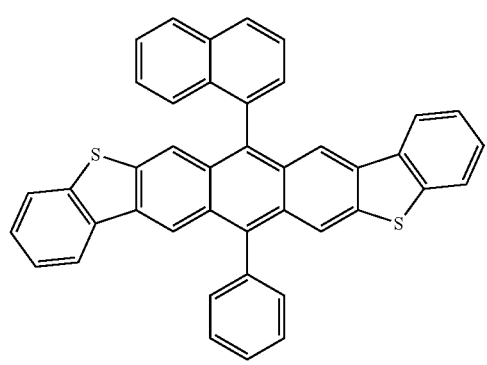
(34)
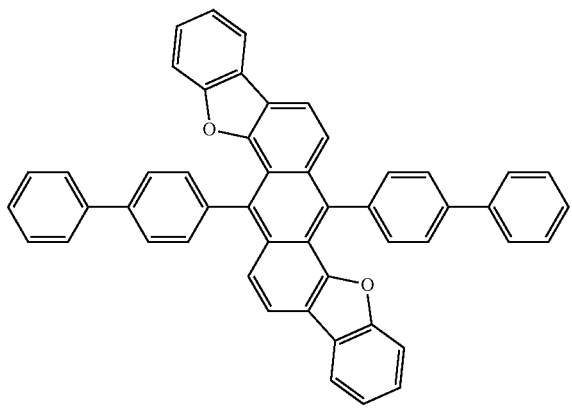
(35)
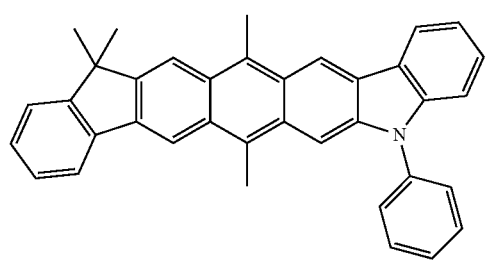
-continued
(36)
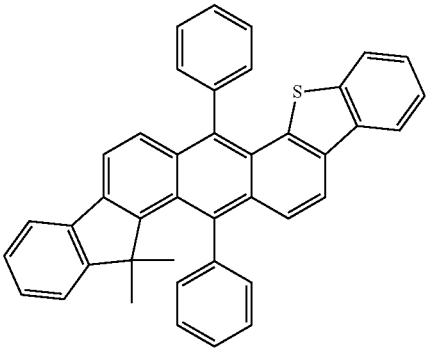
(37)
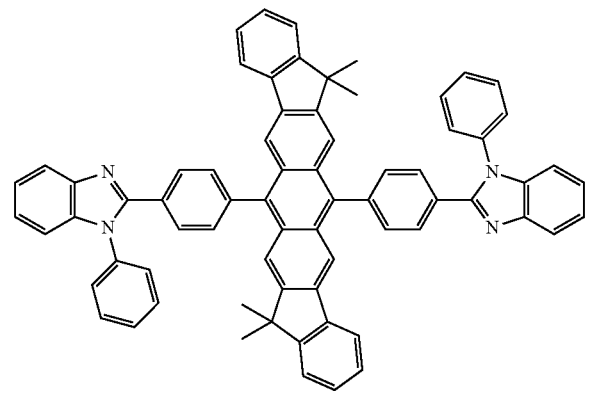
(38)
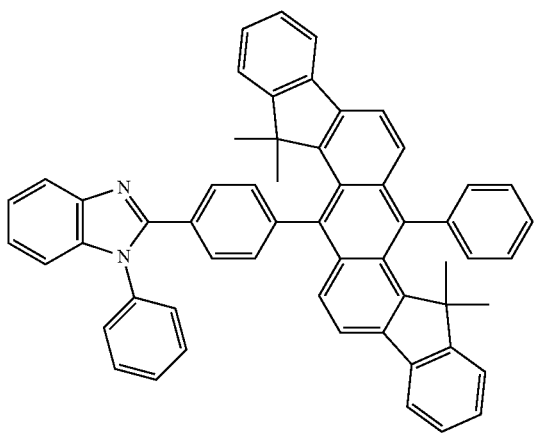
(39)
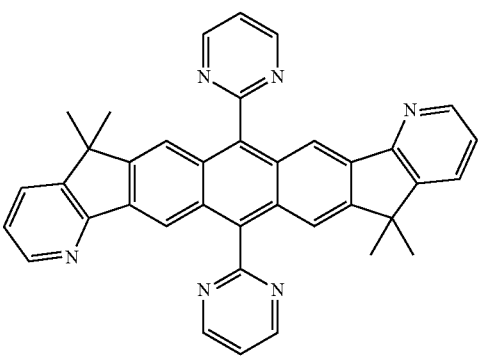

-continued
(40)
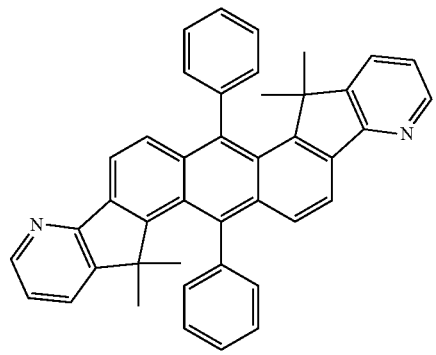
(41)
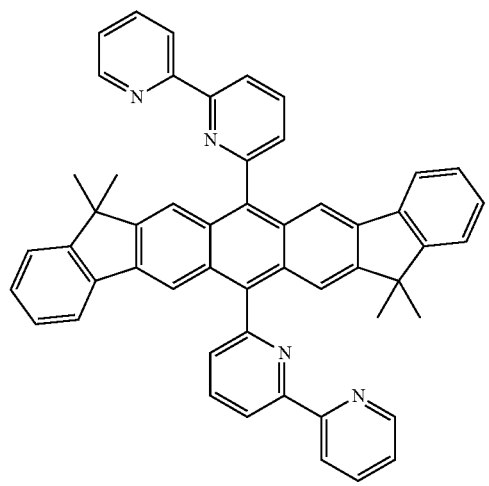
(42)
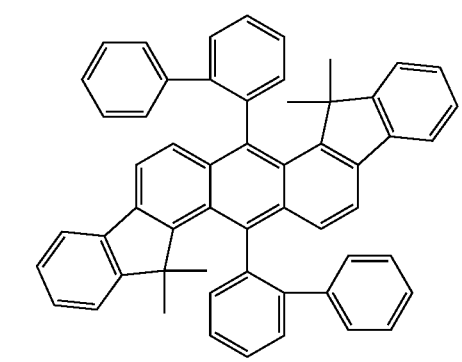
(43)
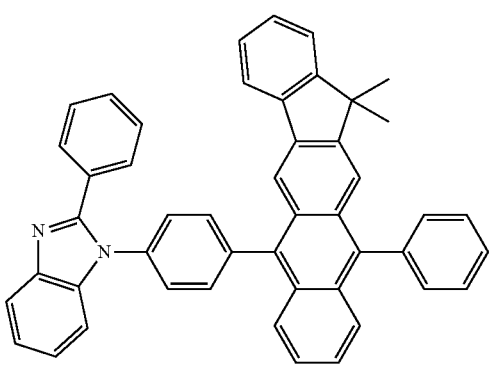
-continued
(44)
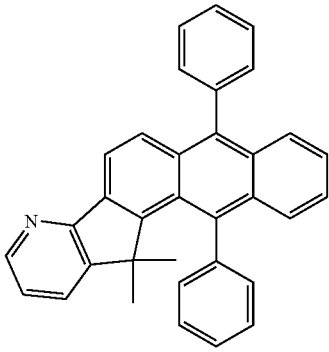
(45)
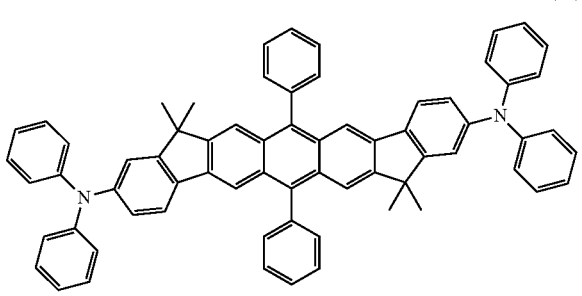
(46)
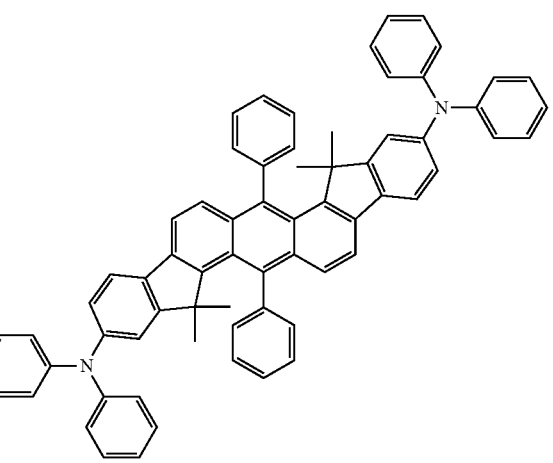
(47)
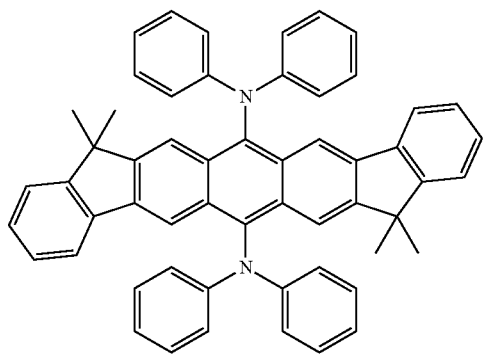

-continued
(48)
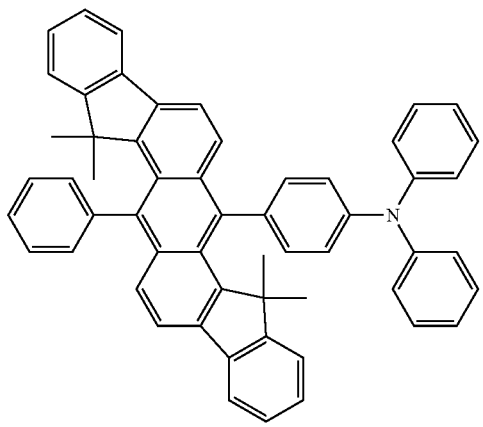
(49)
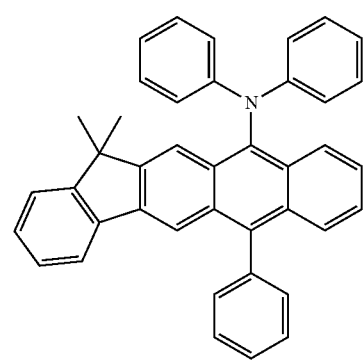
(50)
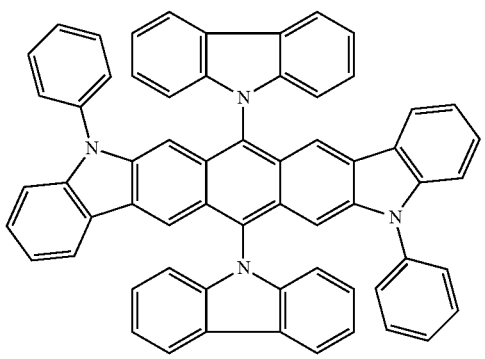
(51)
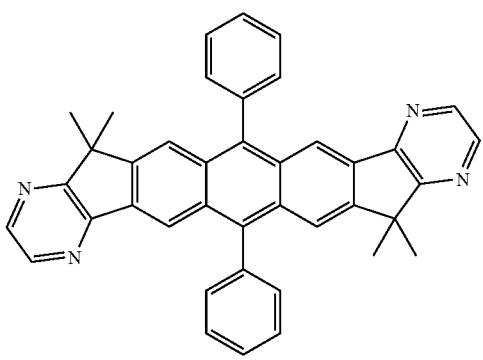
-continued
(52)
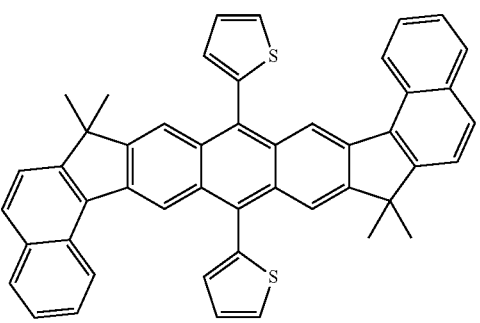
(53)
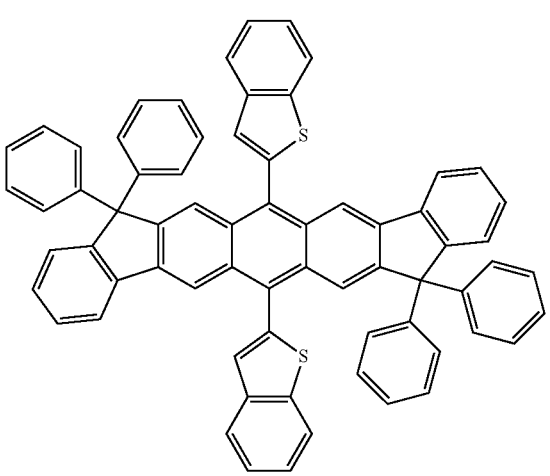
(54)
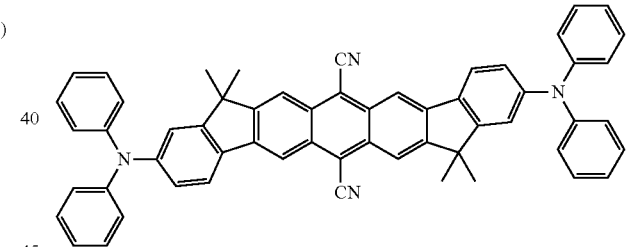
(55)
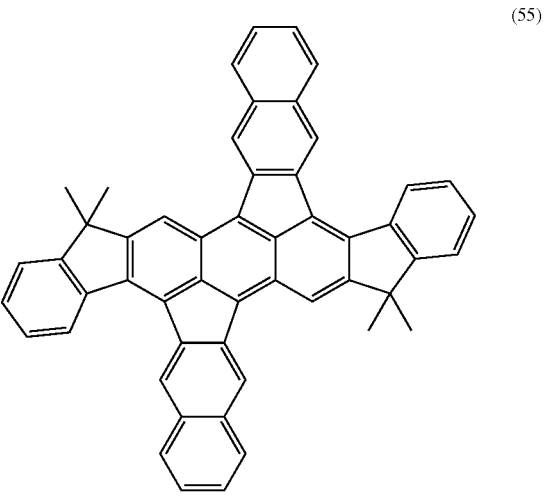

(56)
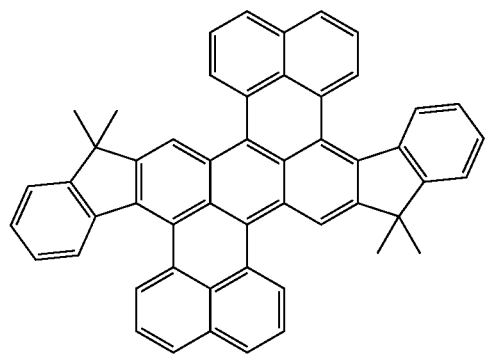
(57)
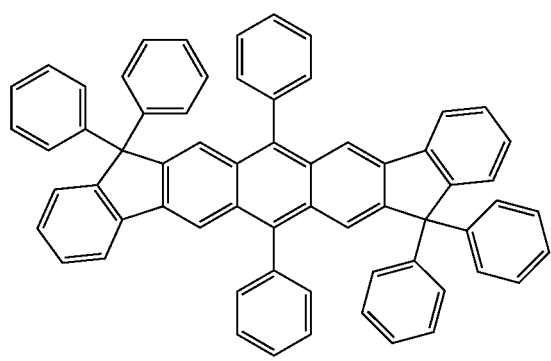
(58)
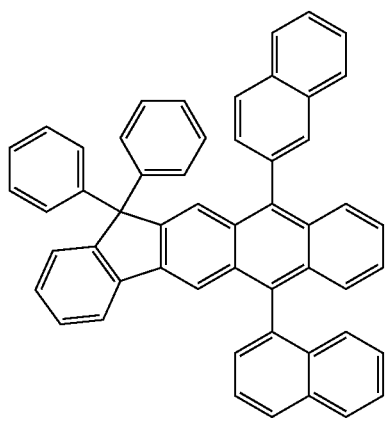
(59)
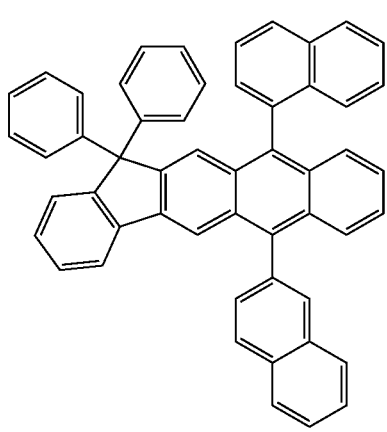
(60)
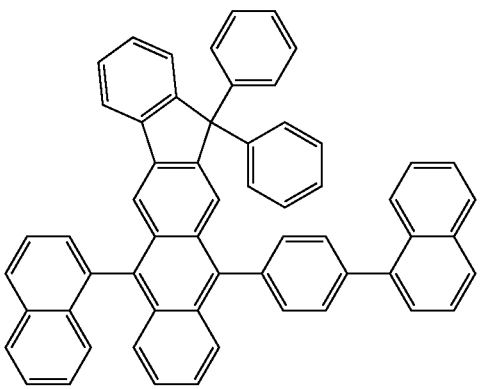
(61)
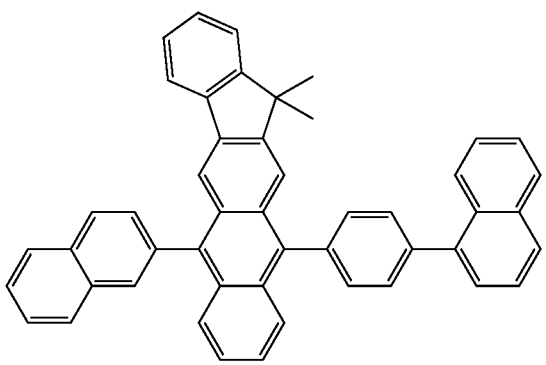
(62)
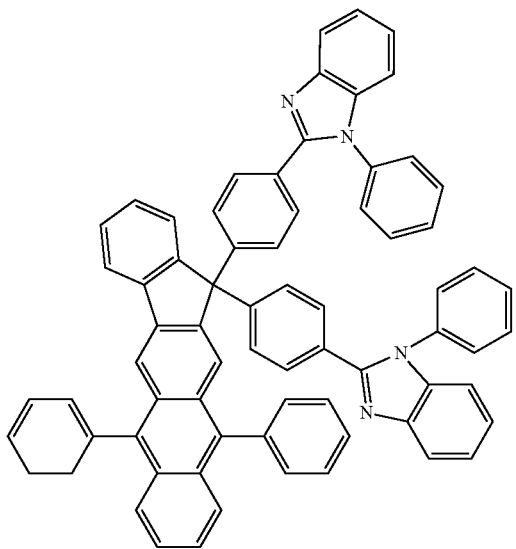

(63)
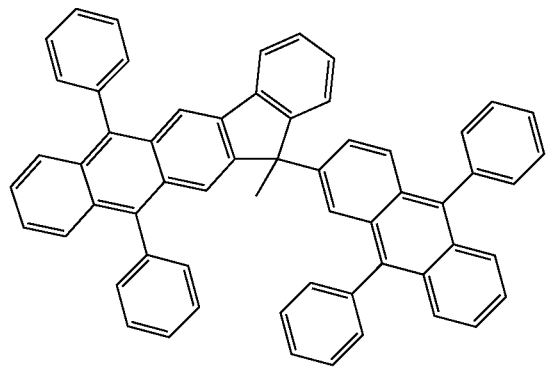
(64)
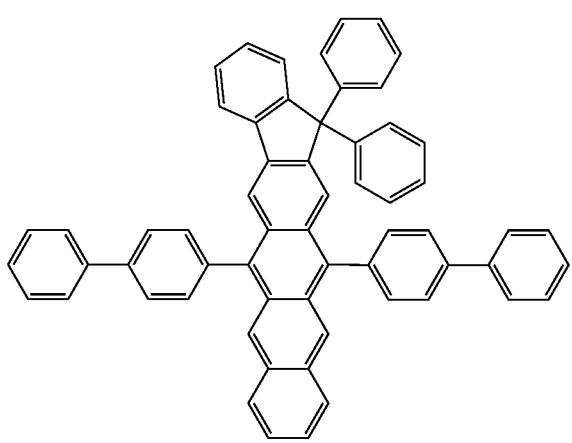
(65)
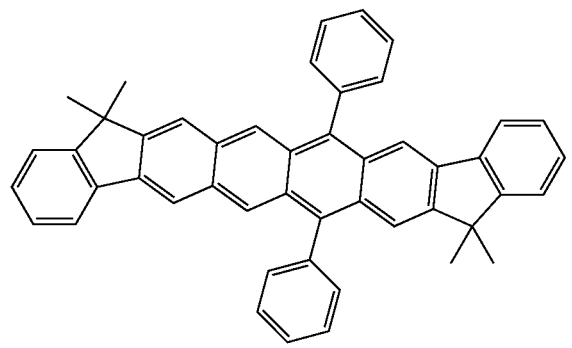
(66)
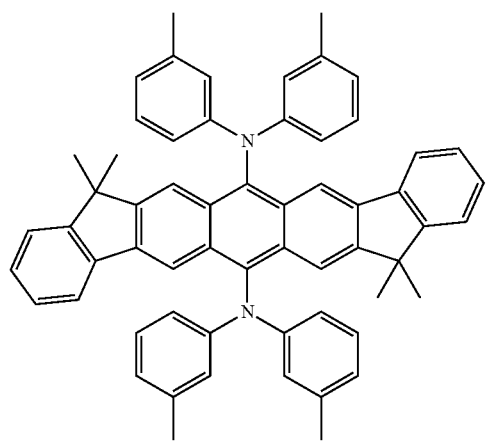
(67)
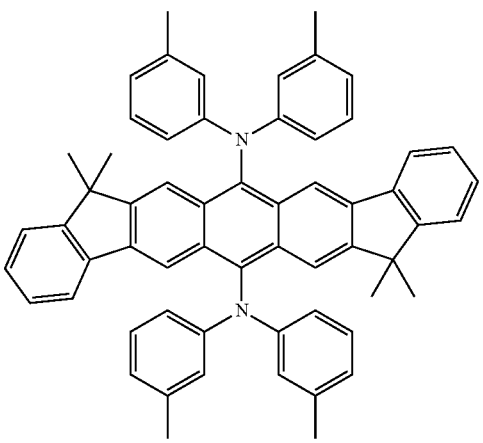
(68)
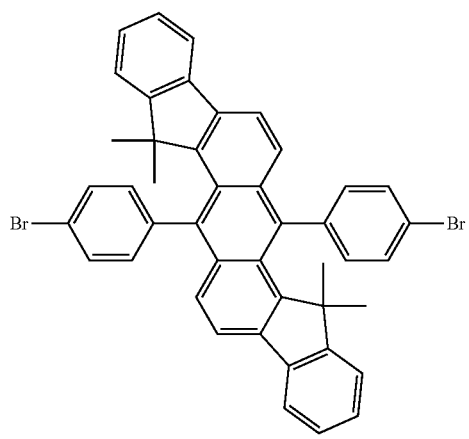
(69)
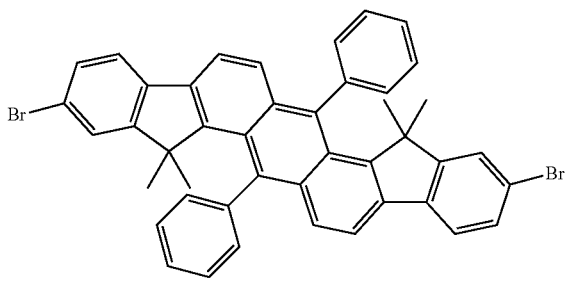
(70)
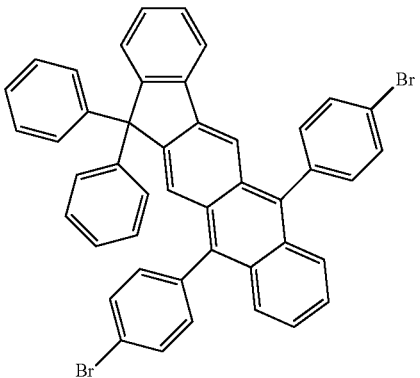

(71)
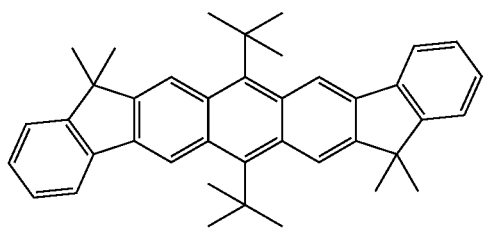
(75)
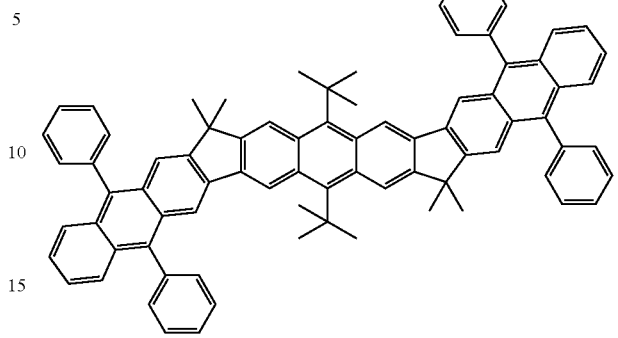
(72)
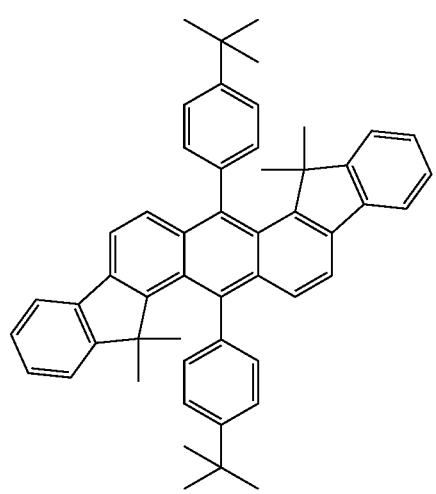
(76)
(73)
(77)
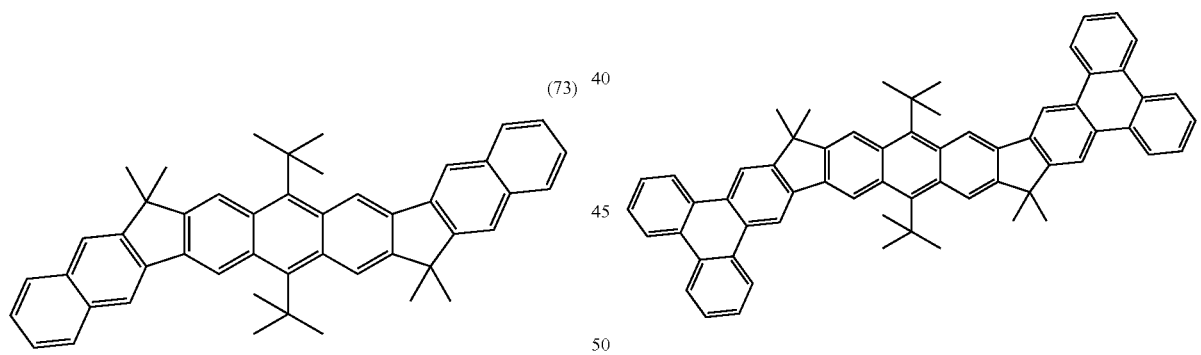
(74)
(78)
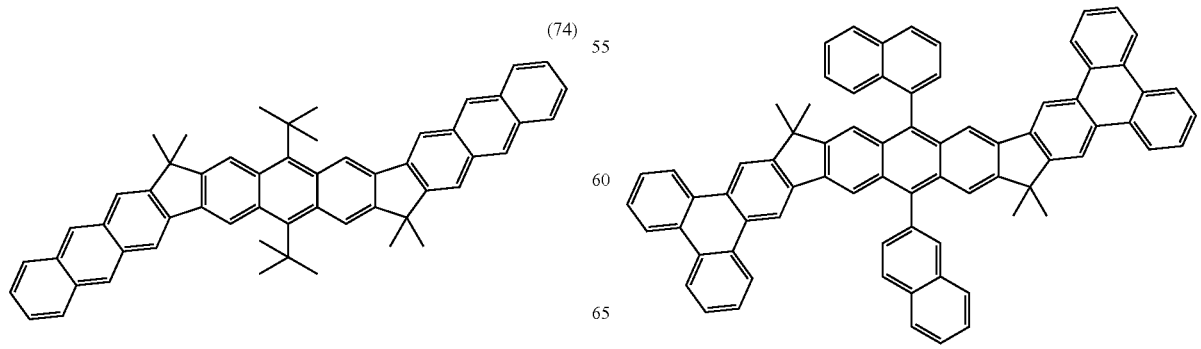

(79)
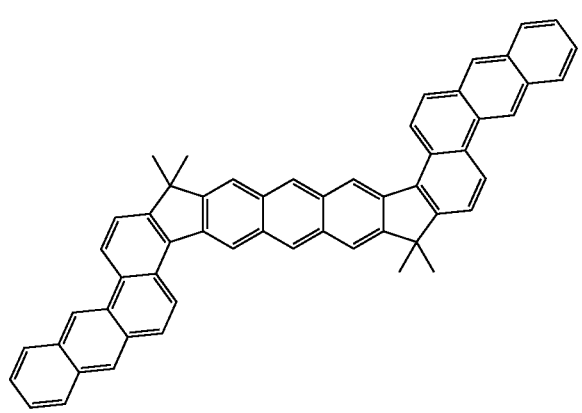
(80)
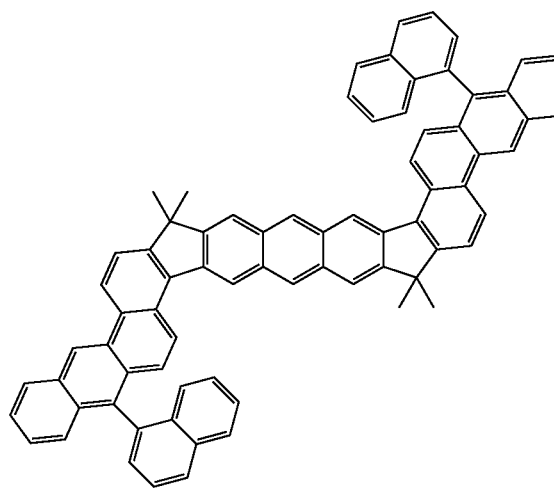
(81)
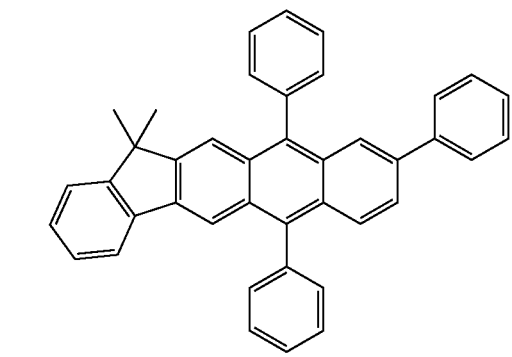
(82)
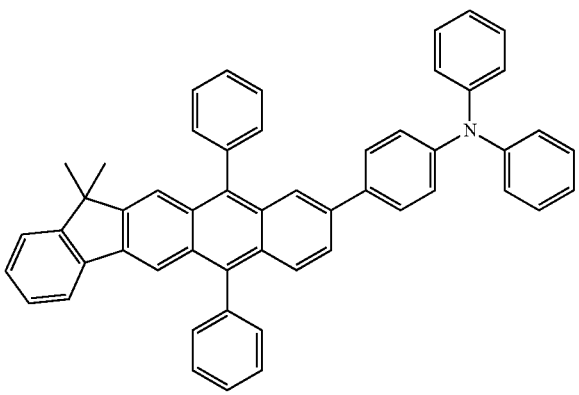
(83)
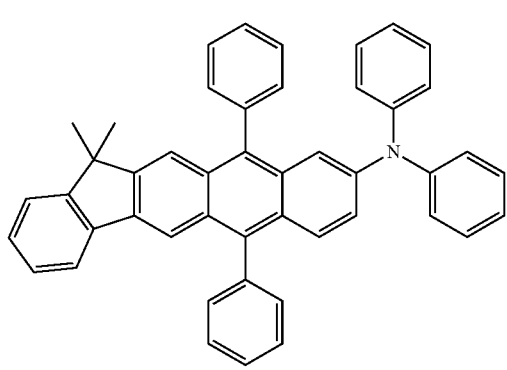
(84)
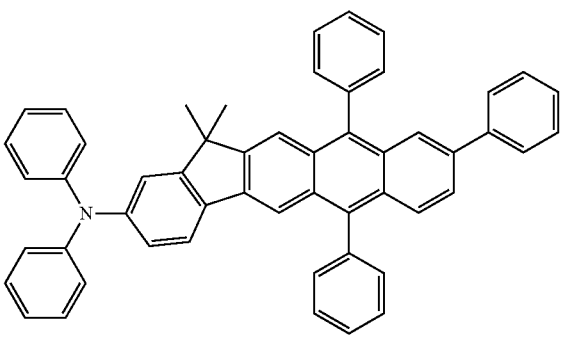

41
-continued
(85)
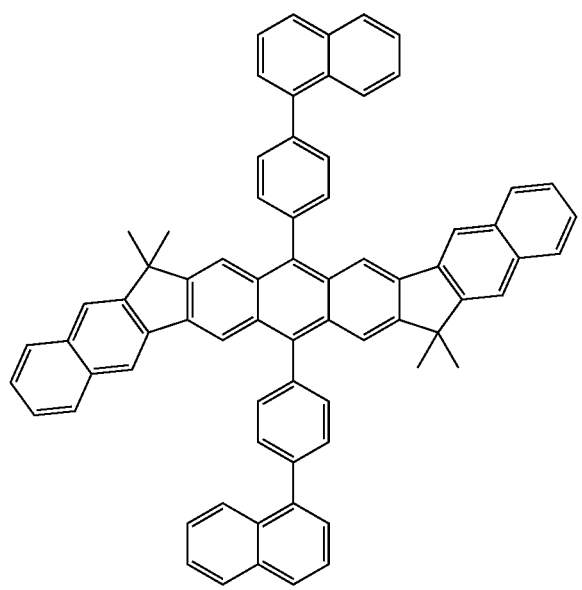
(86)
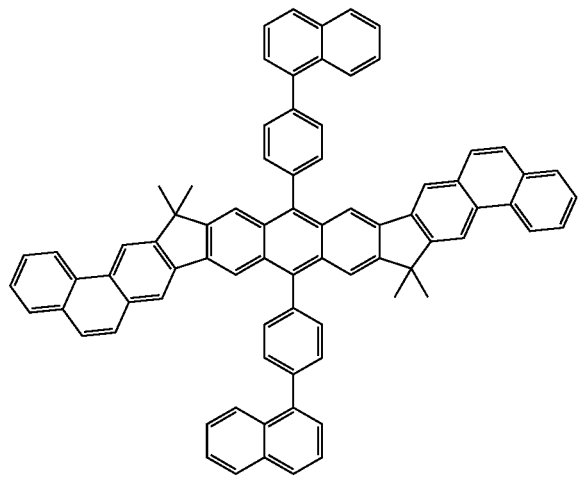
(87)
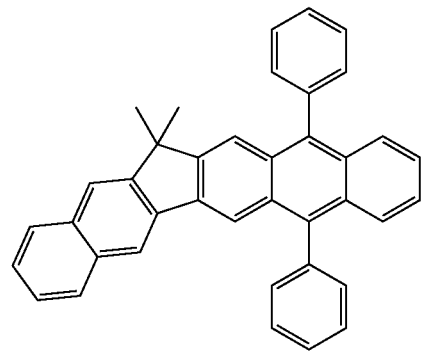
42
-continued
(88)
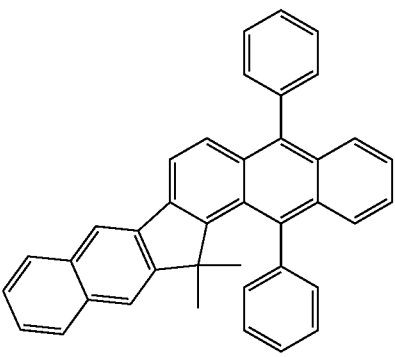
(89)
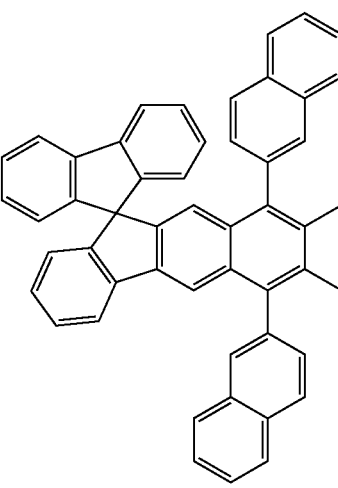
(90)
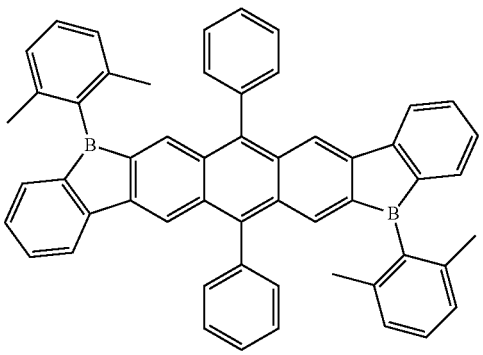
(91)
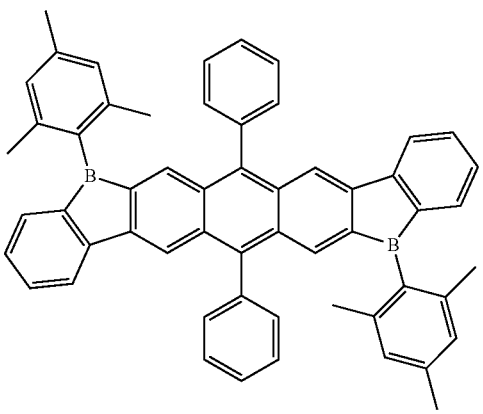

(92)
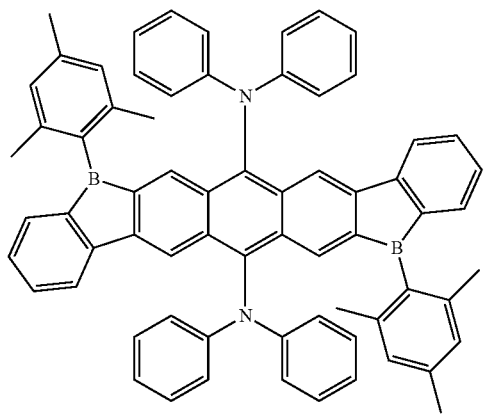
(95)
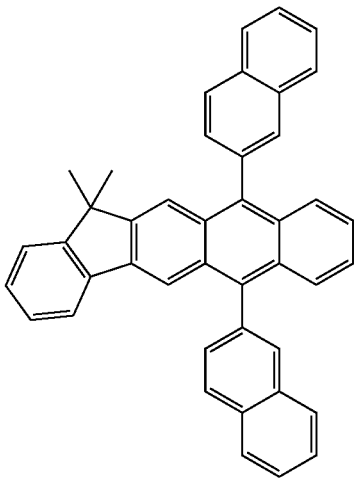
(93)
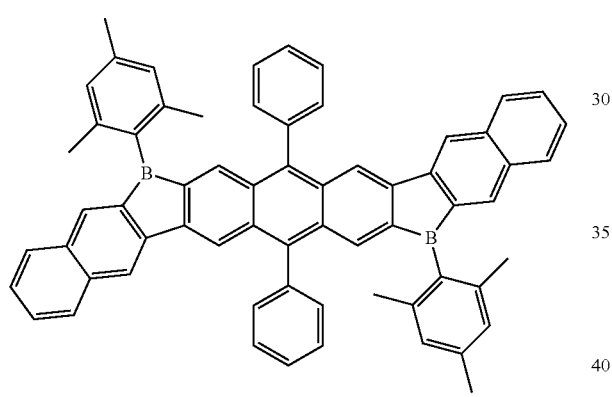
(96)
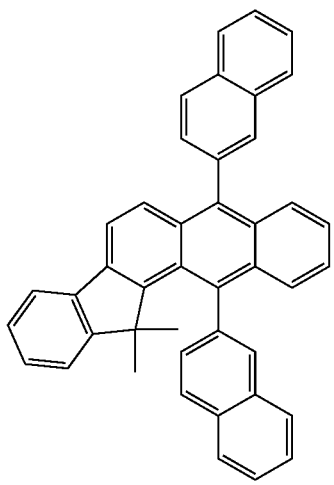
(94)
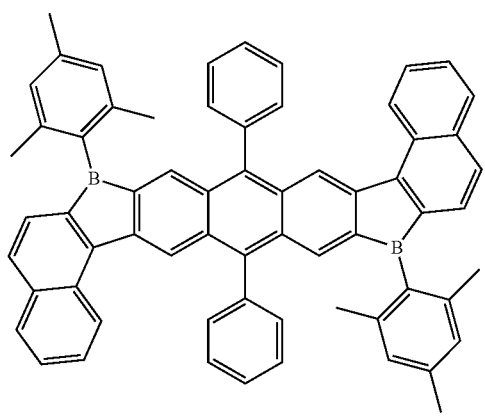
(97)
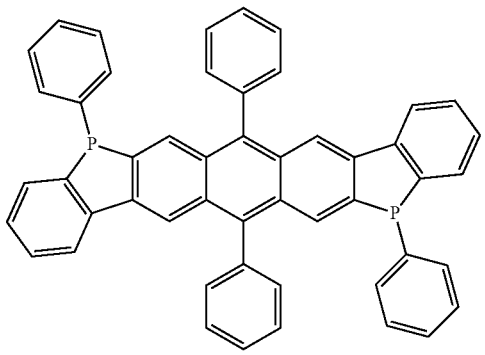

(98)
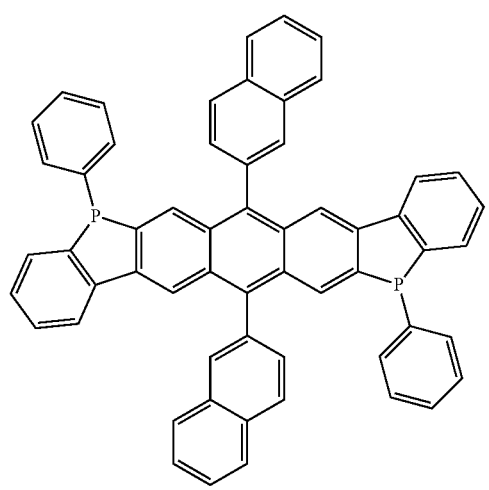
(99)
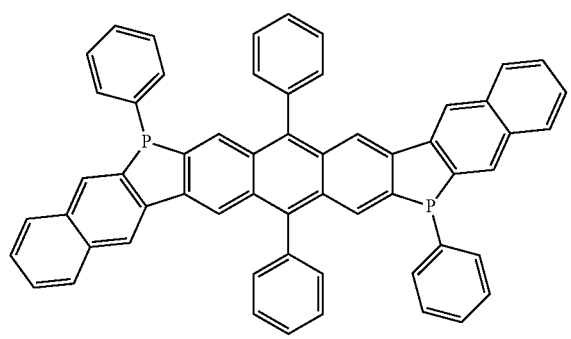
(100)
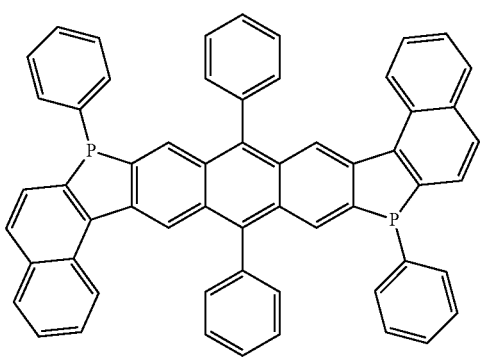
(101)
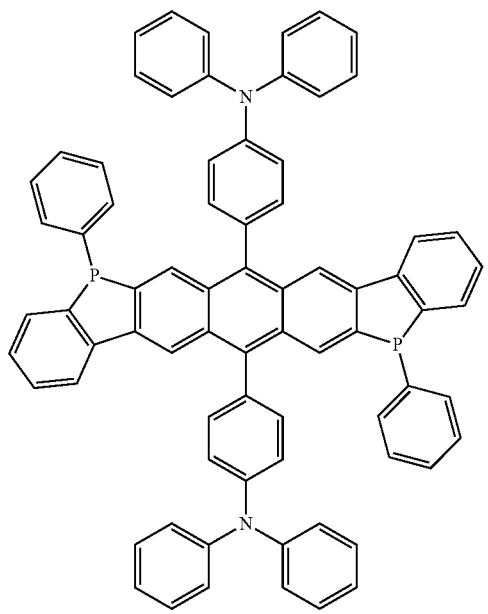
(102)
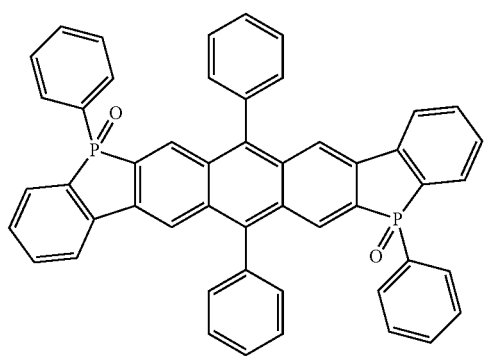
(103)
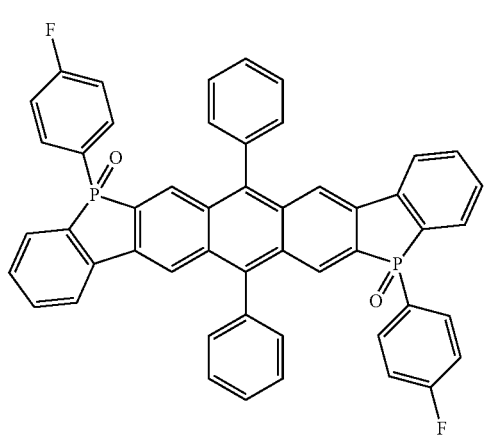

(104)
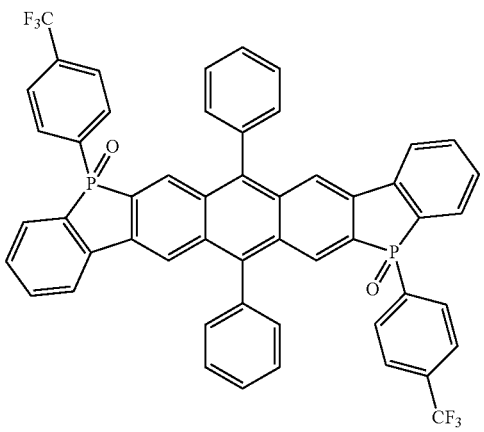
(105)
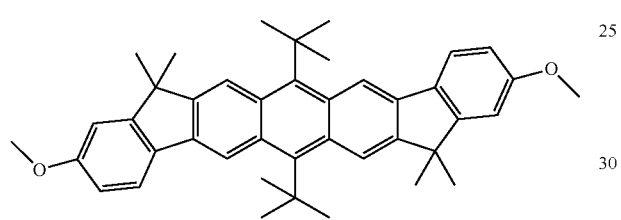
(106)
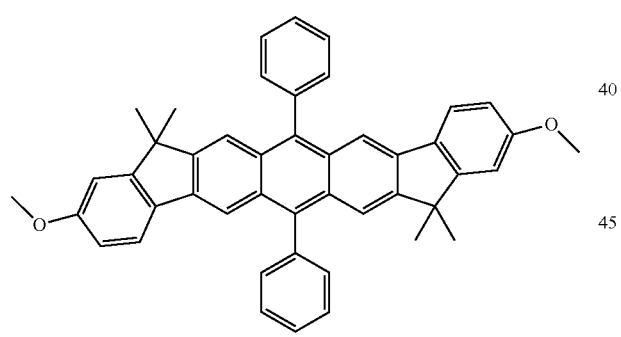
(107)
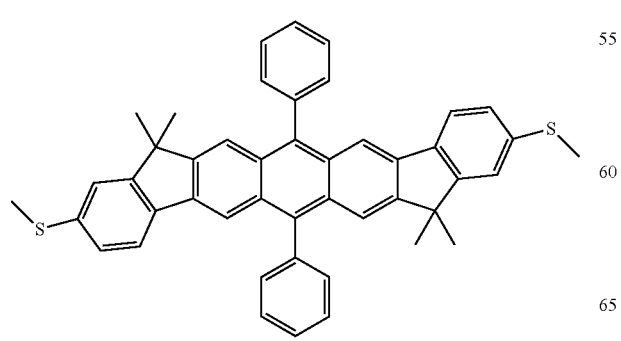
(108)
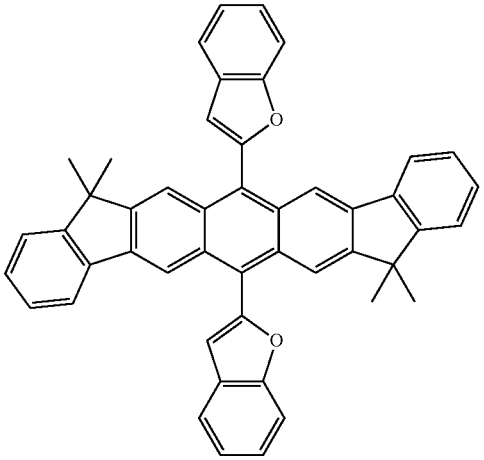
(109)
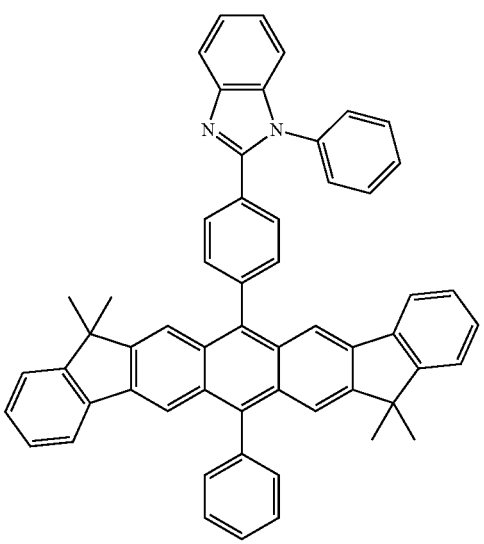
(110)
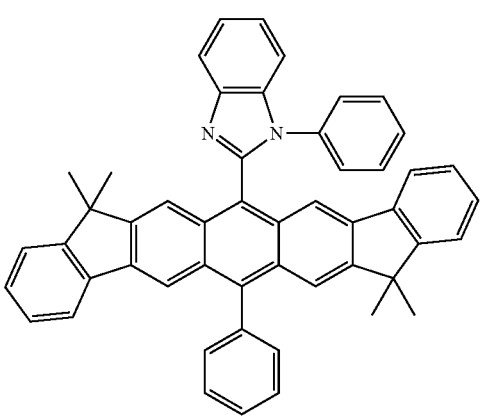

(111)
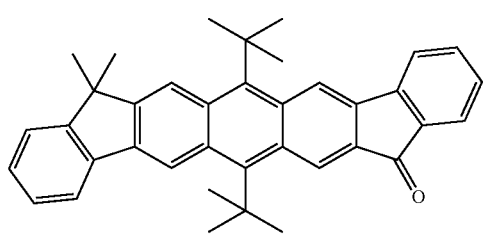
(112)
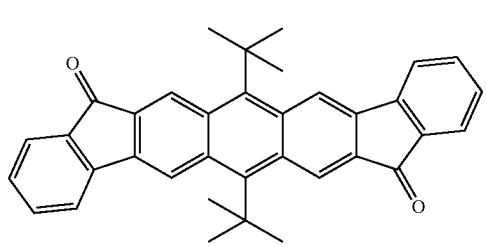
(113)
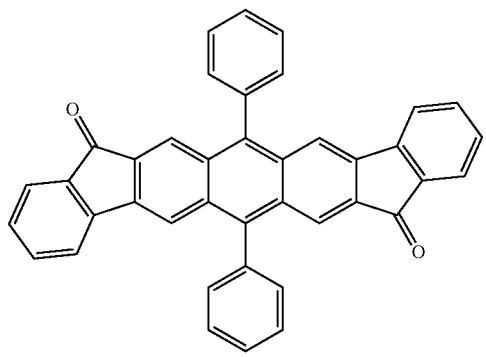
(114)
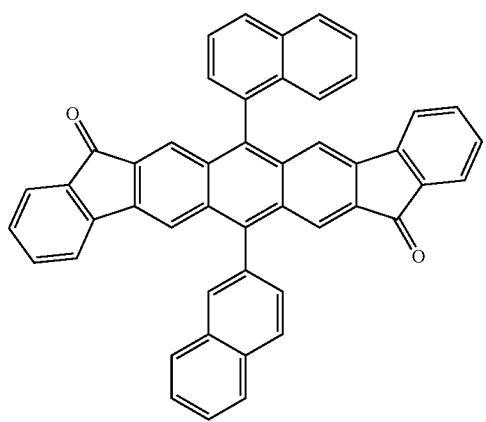
(115)
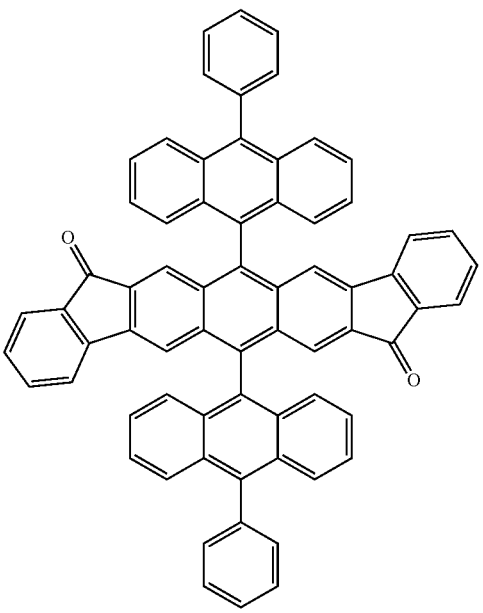
(116)
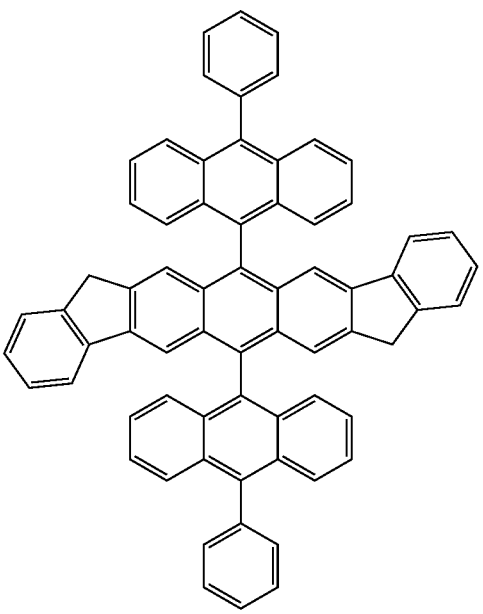
(117)
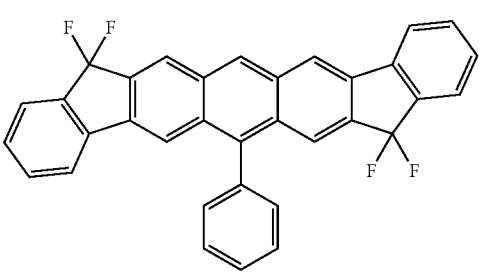

(118)
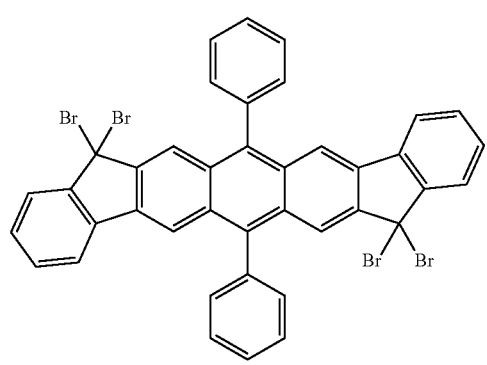
(119)
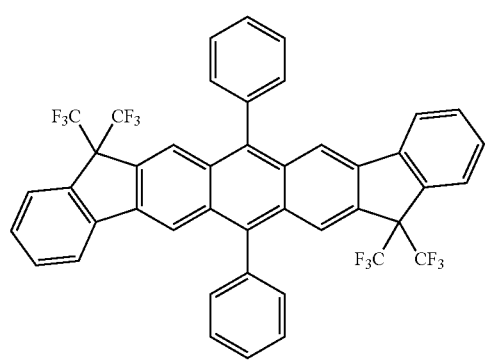
(120)
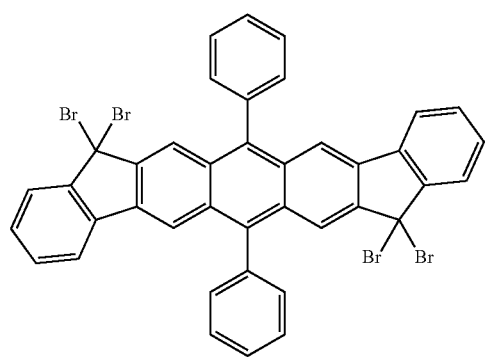
(121)
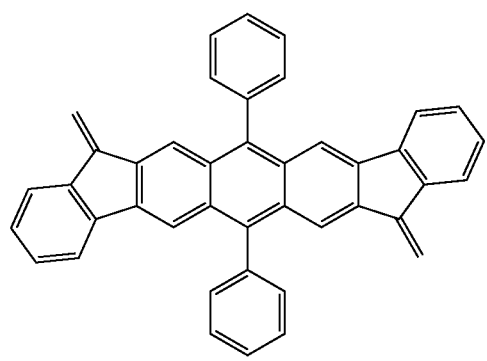
(122)
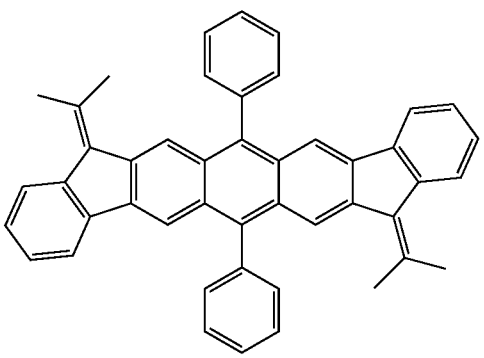
(123)
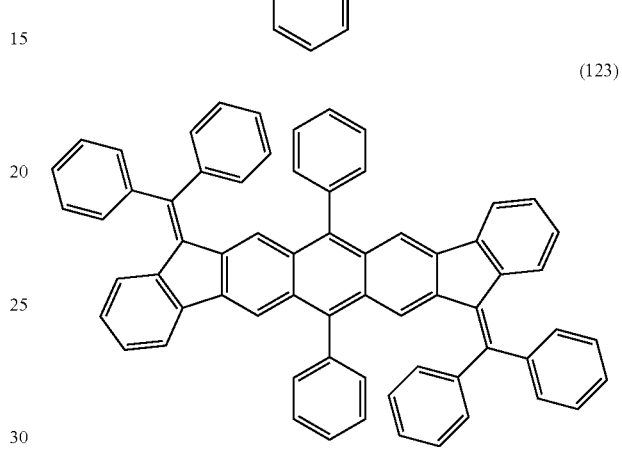
(124)
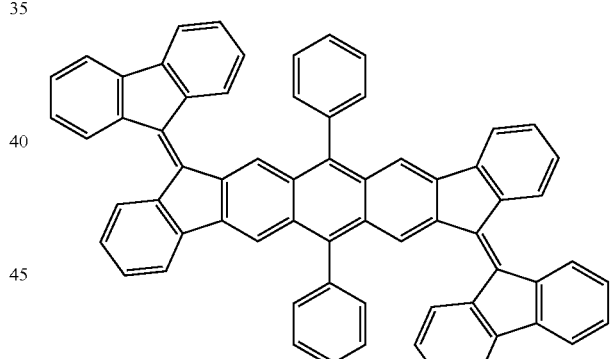
(125)
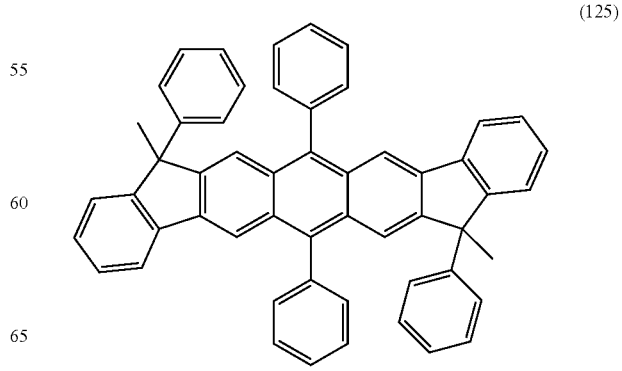

(126)
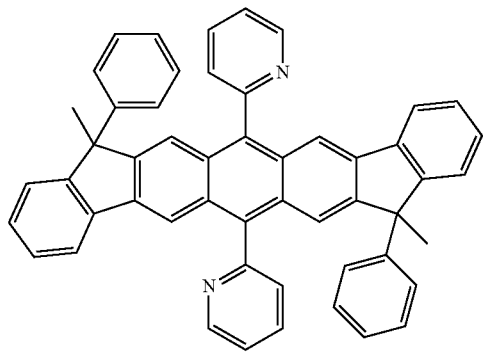
(127)
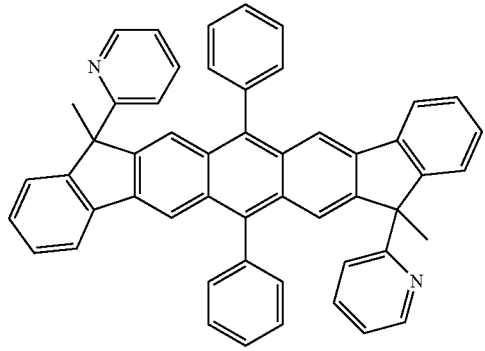
(128)
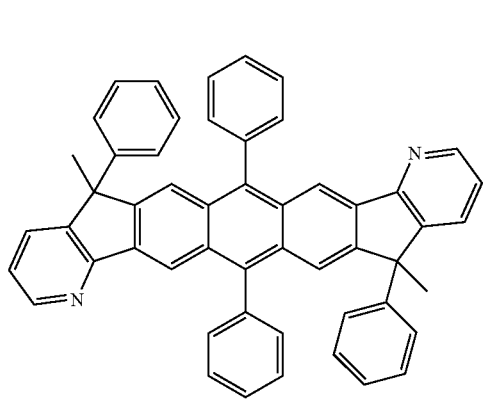
(129)
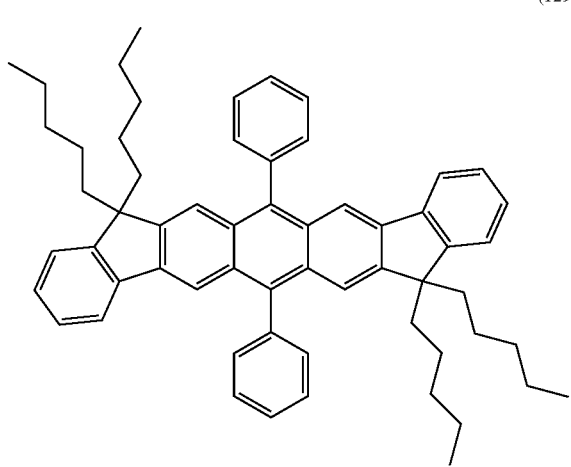
(130)
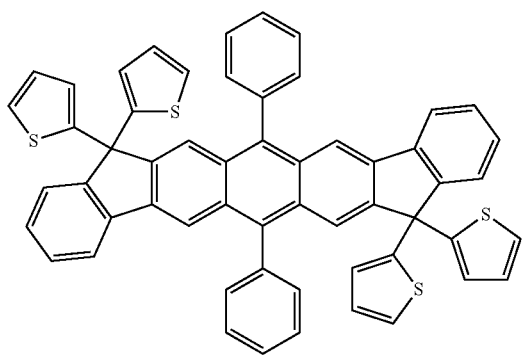
(131)
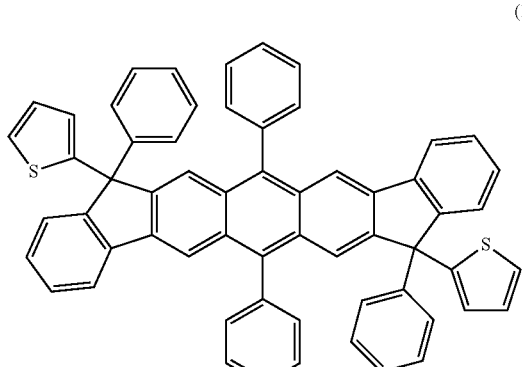
(132)
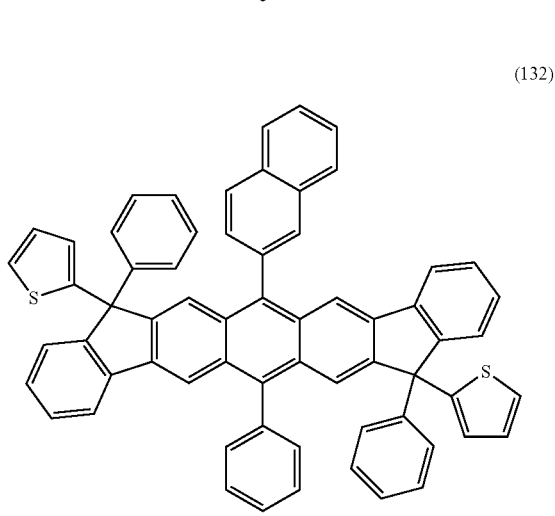
(133)
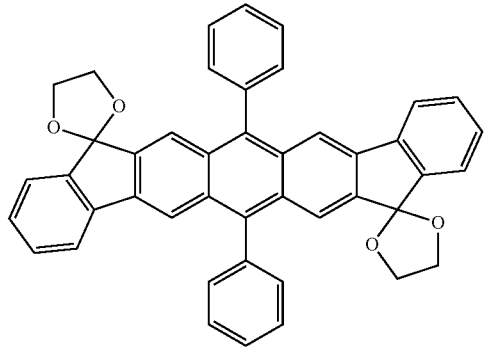

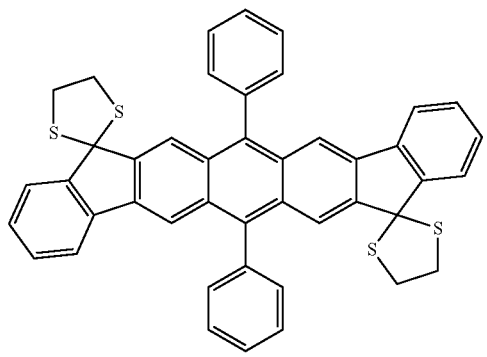

The compounds of the formulae (1) and (2) according to the invention can be prepared by synthetic steps known to the person skilled in the art. The synthesis is depicted by way of example in Scheme 1 below. A suitable starting compound is 2,6-dibromoanthraquinone, which can be obtained from 2,6-diaminoanthraquinone by diazotisation and reaction with CuBr$_2$. The radicals R can be introduced in the form of an arylmetal compound, for example an aryllithium compound or an aryl-Grignard compound, followed by reduction of the alcohols formed. The bromide can be reacted with a diboron compound, for example bis(pinacolato)diboron, with palladium catalysis to give the corresponding boronic acid derivative, which can be reacted with a 2-haloalkyl benzoate in a Suzuki coupling. The radicals on the bridge X are then introduced by reaction with an aryllithium compound or an aryl-Grignard compound, and the cyclisation to give the compound of the formula (1) or (2) is carried out under acidic conditions. Depending on the precise cyclisation conditions, the cyclisation may also give mixtures, which can then be separated or also employed in the organic electroluminescent device as a mixture.

Scheme 1

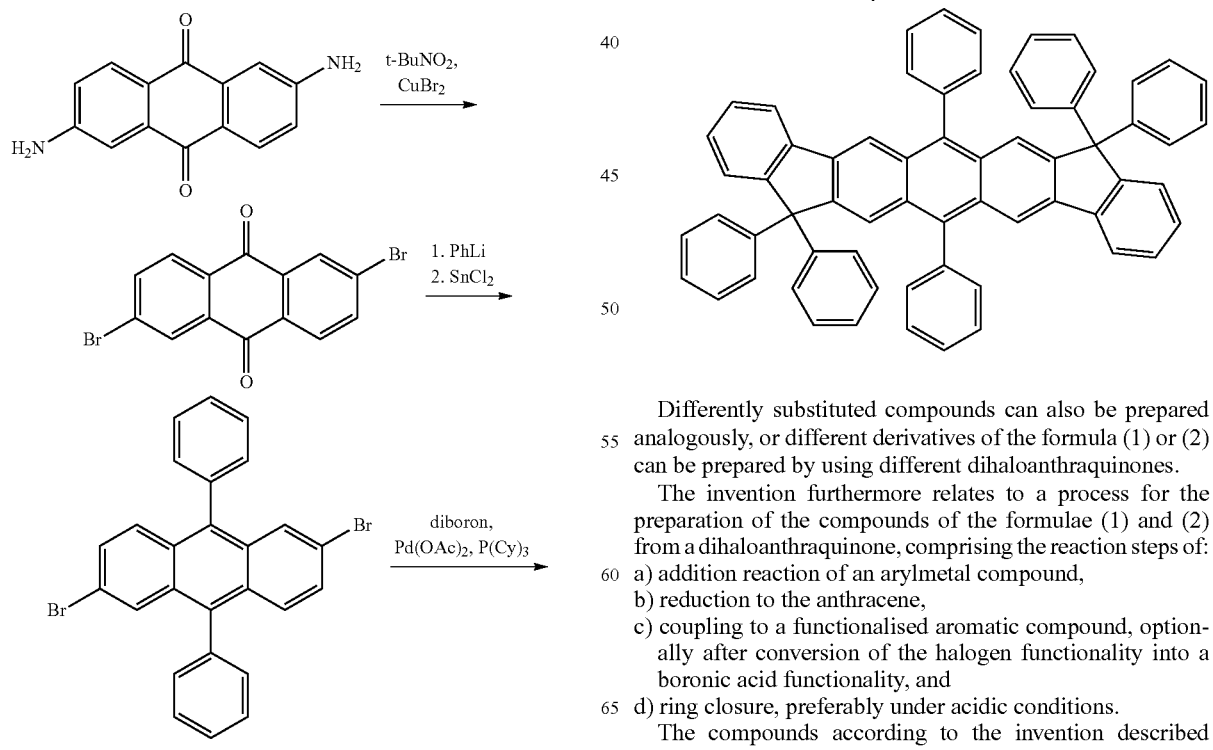

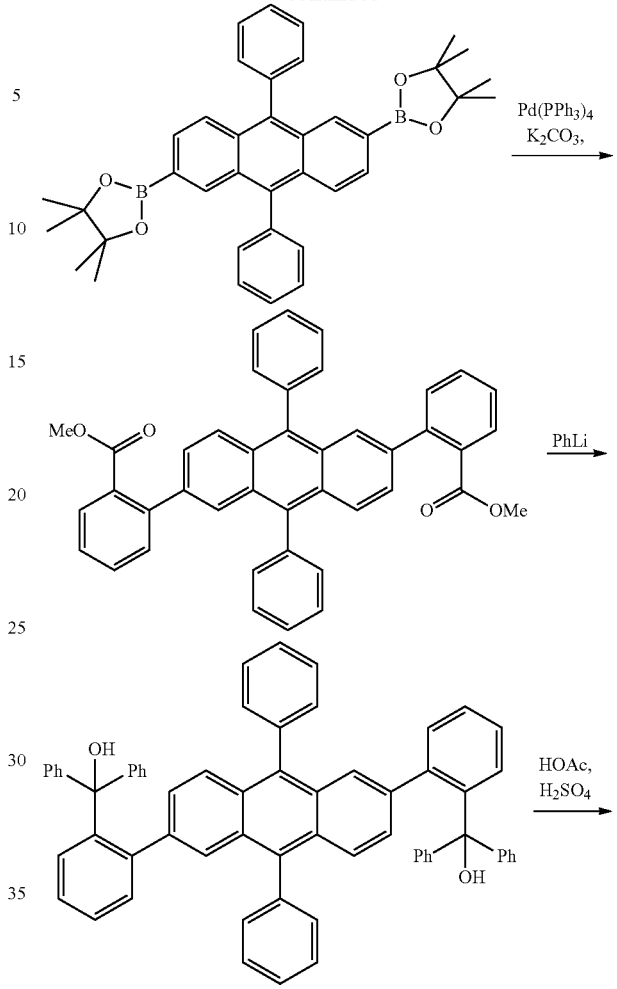

Differently substituted compounds can also be prepared analogously, or different derivatives of the formula (1) or (2) can be prepared by using different dihaloanthraquinones.

The invention furthermore relates to a process for the preparation of the compounds of the formulae (1) and (2) from a dihaloanthraquinone, comprising the reaction steps of:
a) addition reaction of an arylmetal compound,
b) reduction to the anthracene,
c) coupling to a functionalised aromatic compound, optionally after conversion of the halogen functionality into a boronic acid functionality, and
d) ring closure, preferably under acidic conditions.

The compounds according to the invention described above, in particular compounds which are substituted by reactive leaving groups, such as bromine, iodine, boronic acid or boronic acid ester, can be used as monomers for the preparation of corresponding dimers, trimers, tetramers, pentamers, oligomers, polymers or as the core of dendrimers. The oligomerisation or polymerisation here is preferably carried out via the halogen functionality or the boronic acid functionality.

The invention therefore furthermore relates to dimers, trimers, tetramers, pentamers, oligomers, polymers or dendrimers comprising one or more compounds of the formulae (1) and/or (2), where one or more radicals R, $R^1$ or $R^2$ represent bonds between the compounds of the formula (1) or (2) in the dimer, trimer, tetramer or pentamer or bonds from the compound of the formula (1) or (2) to the polymer, oligomer or dendrimer. For the purposes of this invention, an oligomer is taken to mean a compound which has at least six units of the formulae (1) and/or (2). The polymers, oligomers or dendrimers may be conjugated, partially conjugated or non-conjuated. The trimers, tetramers, pentamers, oligomers or polymers may be linear or branched. In the linearly linked structures, the units of the formulae (1) and/or (2) can either be linked directly to one another or linked to one another via a divalent group, for example via a substituted or unsubstituted alkylene group, via a heteroatom or via a divalent aromatic or heteroaromatic group. In branched structures, for example, three or more units of the formulae (1) and/or (2) may be linked via a trivalent or polyvalent group, for example via a trivalent or polyvalent aromatic or heteroaromatic group, to give a branched trimer, tetramer, pentamer, oligomer or polymer.

For the recurring units of the formulae (1) and (2) in dimers, trimers, tetramers, pentamers, oligomers and polymers, the same preferences apply as described above.

For the preparation of the oligomers or polymers, the monomers according to the invention are homopolymerised or copolymerised with further monomers. Suitable and preferred comonomers are selected from fluorenes (for example in accordance with EP 842208 or WO 00/22026), spirobifluorenes (for example in accordance with EP 707020, EP 894107 or WO 06/061181), para-phenylenes (for example in accordance with WO 92/18552), carbazoles (for example in accordance with WO 04/070772 or WO 04/113468), thiophenes (for example in accordance with EP 1028136), dihydrophenanthrenes (for example in accordance with WO 05/014689), cis- and trans-indenofluorenes (for example in accordance with WO 04/041901 or WO 04/113412), ketones (for example in accordance with WO 05/040302), phenanthrenes (for example in accordance with WO 05/104264 or WO 07/017,066) or also a plurality of these units. The polymers, oligomers and dendrimers usually also contain further units, for example emitting (fluorescent or phosphorescent) units, such as, for example, vinyltriarylamines (for example in accordance with WO 07/068,325) or phosphorescent metal complexes (for example in accordance with WO 06/003000), and/or charge-transport units, in particular those based on triarylamines.

The compounds of the formulae (1) and (2) according to the invention are suitable for use in electronic devices, in particular in organic electroluminescent devices (OLEDs, PLEDs). Depending on the substitution, the compounds are employed in various functions and layers.

The invention therefore furthermore relates to the use of compounds of the formula (1) or formula (2) in electronic devices, in particular in organic electroluminescent devices.

The invention still furthermore relates to organic electronic devices comprising at least one compound of the formulae (1) and/or (2), in particular organic electroluminescent devices comprising anode, cathode and at least one emitting layer, characterised in that at least one organic layer, which may be an emitting layer or another layer, comprises at least one compound of the formulae (1) and/or (2).

Apart from the cathode, anode and emitting layer, the organic electroluminescent device may also comprise further layers. These are, for example, selected from in each case one or more hole-injection layers, hole-transport layers, hole-blocking layers, electron-transport layers, electron-injection layers, electron-blocking layers, charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions. However, it should be pointed out here that each of these layers does not necessarily have to be present, and the choice of the layers is always dependent on the compounds used and in particular also on whether the device is a fluorescent or phosphorescent electroluminescent device.

In a further preferred embodiment of the invention, the organic electroluminescent device comprises a plurality of emitting layers, where at least one organic layer comprises at least one compound of the formula (1) or (2). These emission layers particularly preferably have in total a plurality of emission maxima between 380 nm and 750 nm, resulting overall in white emission, i.e. various emitting compounds which are able to fluoresce or phosphoresce and which emit blue and yellow, orange or red light are used in the emitting layers. Particular preference is given to three-layer systems, i.e. systems having three emitting layers, where at least one of these layers comprises at least one compound of the formula (1) or (2) and where the three layers exhibit blue, green and orange or red emission (for the basic structure, see, for example, WO 05/011013). Emitters which have broad-band emission bands and thus exhibit white emission are likewise suitable for white emission.

In a preferred embodiment of the invention, the compounds of the formulae (1) and (2) are employed as host material for fluorescent dopants, in particular for green- and red-fluorescing dopants. In this case, it is preferred for the group X to be a $C(R^1)_2$ group, for the group Ar to be an aryl group and for the groups R to be H, an alkyl group or an aryl group, where at least one group R represents an alkyl or aryl group; preferably, both groups R represent aryl groups. The same preferences apply to the groups X, Ar and R in structures of the formulae (3) to (15), (3a) to (15a), (3b) to (15b) and (3c) to (15c).

In a system comprising host and dopant, a host material is taken to mean the component which is present in the mixture in the higher proportion. In a system comprising one host and a plurality of dopants, the host is taken to mean the component whose proportion in the mixture is the highest.

The proportion of the host material of the formula (1) or (2) in the emitting layer is between 50.0 and 99.9% by vol., preferably between 80.0 and 99.5% by vol., particularly preferably between 90.0 and 99.0% by vol. Correspondingly, the proportion of the dopant is between 0.1 and 50.0% by vol., preferably between 0.5 and 20.0% by vol., particularly preferably between 1.0 and 10.0% by vol.

Preferred dopants in fluorescent devices are selected from the class of the monostyrylamines, the distyrylamines, the tristyrylamines, the tetrastyrylamines and the arylamines. A monostyrylamine is taken to mean a compound which contains one styryl group and at least one, preferably aromatic, amine. A distyrylamine is taken to mean a compound which contains two styryl groups and at least one, preferably aromatic, amine. A tristyrylamine is taken to mean a compound which contains three styryl groups and at least one, preferably aromatic, amine. A tetrastyrylamine is taken to mean a compound which contains four styryl groups and at least one, preferably aromatic, amine. For the purposes of this invention, an arylamine or an aromatic amine is taken to mean a compound which contains three aromatic or heteroaromatic ring systems bonded directly to the nitrogen, at least one of which is preferably a condensed ring system having at least 14 aromatic ring atoms. The styryl groups are particularly preferably stilbenes, which may also be further substituted on the double bond or on the aromatic ring system. Examples of dopants of this type are substituted or unsubstituted tristilbenamines or further dopants which are described, for example, in WO 06/000388, WO 06/058737, WO 06/000389, WO 07/065,549 and WO 07/115,610. Further preferred dopants are compounds in accordance with WO 06/122630. Examples of arylamines are diarylaminoanthracenes, where the diarylamino group is bonded in the 2- or 9-position, bis(diarylaminoanthracenes), where the diarylamino groups are bonded in the 2,6- or 9,10-position, diarylaminopyrenes, bis(diarylamino)pyrenes, diarylaminochrysenes or bis(diarylamino)chrysenes. Preferred dopants are furthermore diarylamine derivatives or bis(diarylamine) derivatives of monobenzoindenofluorene or dibenzoindenofluorene, for example in accordance with WO 08/006,449 or WO 07/140,847.

Suitable dopants for which the compound of the formula (1) or formula (2) is a suitable host material are furthermore the structures depicted in the following table and the derivatives of these structures which are disclosed in JP 06/001973, WO 04/047499, WO 06/098080, WO 07/065,678, US 2005/0260442 and WO 04/092111.

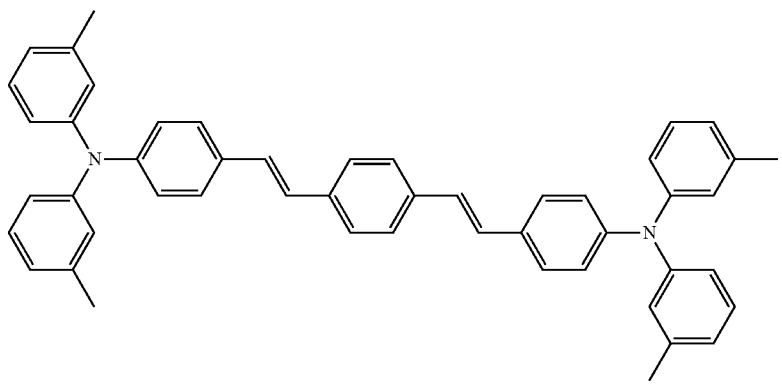 [SMILES: Cc1cccc(N(c2ccc(/C=C/c3ccc(/C=C/c4ccc(N(c5cccc(C)c5)c5cccc(C)c5)cc4)cc3)cc2)c2cccc(C)c2)c1]

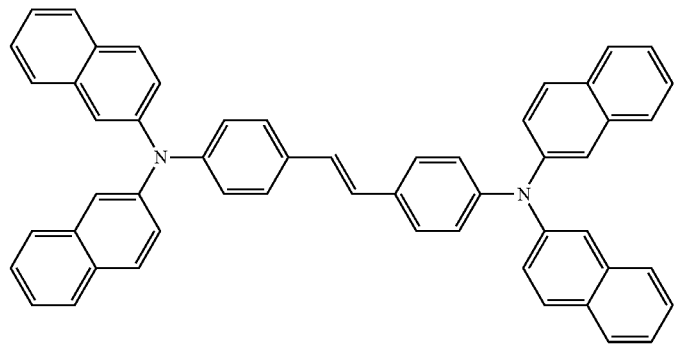 [SMILES: C(=C\c1ccc(N(c2ccc3ccccc3c2)c2ccc3ccccc3c2)cc1)/c1ccc(N(c2ccc3ccccc3c2)c2ccc3ccccc3c2)cc1]

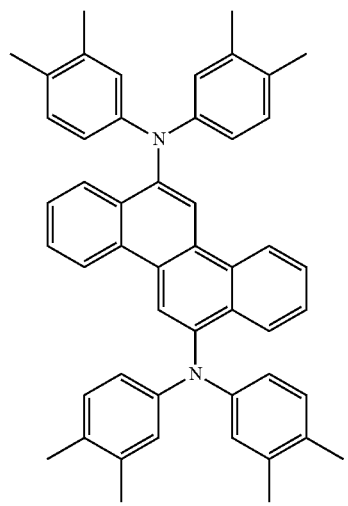

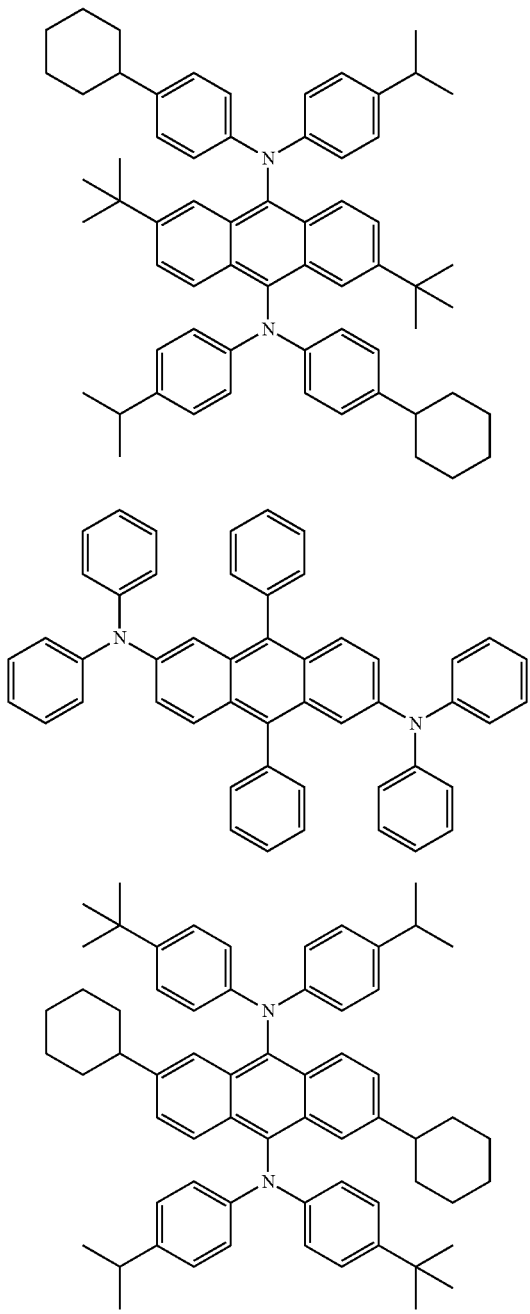

In a further preferred embodiment of the invention, the compounds of the formulae (1) and (2) are employed as emitting materials. The compounds are preferred, in particular, if the radicals R stand for an aromatic or heteroaromatic ring system. This leads to emitting compounds which exhibit deep-blue emission with a very narrow emission spectrum. The compounds are furthermore suitable as emitting compounds If at least one substituent R contains at least one vinylaryl unit, at least one vinylarylamine unit and/or at least one arylamino or diarylamino unit. Preferred arylamino units are the groups of the formulae (16) and (17) depicted above. The same preferences apply to the groups R in structures of the formulae (3) to (15) and (3a) to (15a) and (3b) to (15b) and (3c) to (15c). Particularly preferred dopants are those in which either two radicals R stand for groups of the formula (16) or (17) or in which one radical R stands for a group of the formula (16) or (17) and the other radicals R stand for H, an alkyl group or an aryl group.

The proportion of the compound of the formula (1) or (2) in the mixture of the emitting layer is between 0.1 and 50.0% by vol., preferably between 0.5 and 20.0% by vol., particularly preferably between 1.0 and 10.0% by vol. Correspondingly, the proportion of the host material is between 50.0 and 99.9% by vol., preferably between 80.0 and 99.5% by vol., particularly preferably between 90.0 and 99.0% by vol.

Suitable host materials for this purpose are materials from various classes of substance. Preferred host materials are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 04/081017), the hole-conducting compounds (for example in accordance with WO 04/058911), the electron-conducting compounds, in particular ketones, phosphine oxides, sulfoxides, etc. (for example in accordance with WO 05/084081 and WO 05/084082), the atropisomers (for example in accordance with WO 06/048268), the boronic acid derivatives (for example in accordance with WO 06/117052) or the benzanthracene derivatives (for example in accordance with WO 08/145239). Further suitable host materials are also the compounds according to the invention which are described above. Apart from the compounds according to the invention, particularly preferred host materials are selected from the classes of the oligoarylenes containing naphthalene, anthracene, benzanthracene and/or pyrene or atropisomers of these compounds, the oligoarylenevinylenes, the ketones, the phosphine oxides and the sulfoxides. Apart from the compounds according to the invention, very particularly preferred host materials are selected from the classes of the oligoarylenes containing anthracene, benzanthracene and/or pyrene or atropisomers of these compounds. For the purposes of this invention, an oligoarylene is intended to be taken to mean a compound in which at least three aryl or arylene groups are bonded to one another.

Suitable host materials are furthermore the materials depicted in the following table, and derivatives of these materials, as disclosed in WO 04/018587, WO 08/006,449, U.S. Pat. No. 5,935,721, US 2005/0181232, JP 2000/273056, EP 681019, US 2004/0247937 and US 2005/0211958.

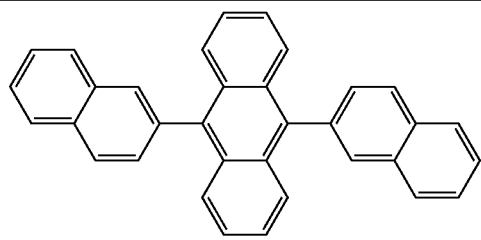

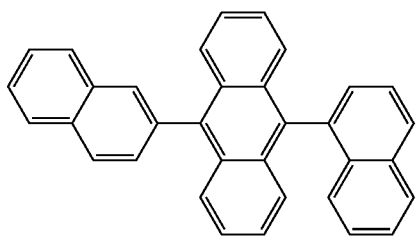

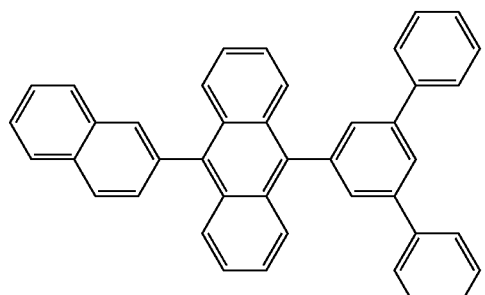

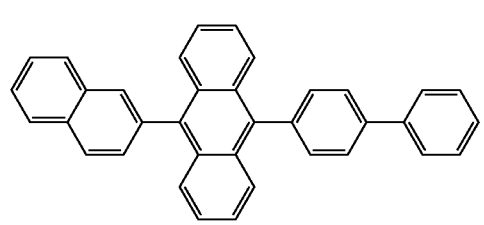

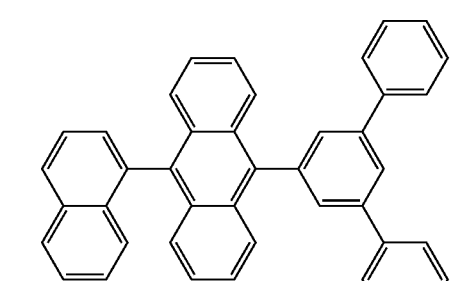

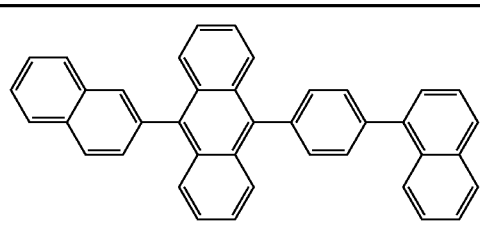

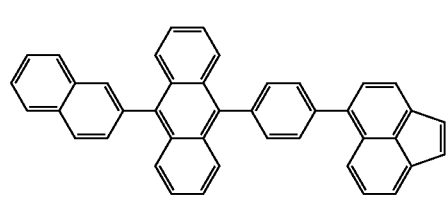 [SMILES: C1=Cc2ccc(-c3ccc(-c4c5ccccc5c(-c5ccc6ccccc6c5)c5ccccc45)cc3)c3cccc1c23]

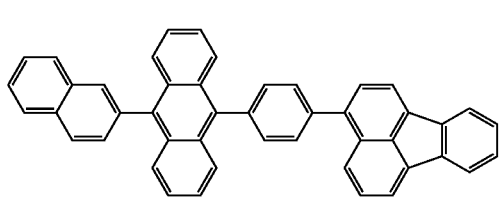 [SMILES: c1ccc2c(c1)-c1cccc3c(-c4ccc(-c5c6ccccc6c(-c6ccc7ccccc7c6)c6ccccc56)cc4)ccc-2c13]

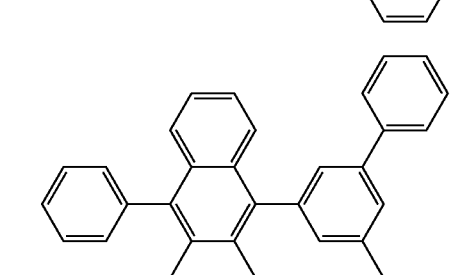

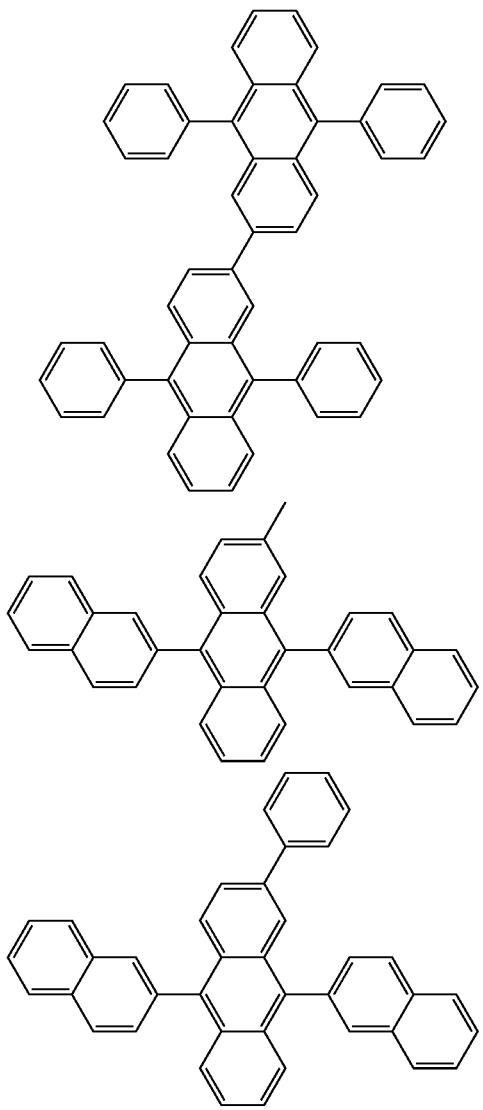

In yet a further embodiment of the invention, the compounds of the formulae (1) and (2) are employed as hole-transport material or as hole-injection material. The compounds are then preferably substituted by at least one group N(Ar$^1$)$_2$, preferably by at least two groups N(Ar$^1$)$_2$, and/or they contain further groups which improve hole transport. The groups N(Ar$^1$)$_2$ are preferably selected from the formulae (16) and (17) described above. This applies, in particular, to the radicals R on the structures of the formulae (3) to (15) and (3a) to (15a) and (3b) to (15b) and (3c) to (15c). Further preferred groups which improve hole transport are, for example, the groups N(R$^1$), S or O, in particular N(R$^1$), as bridging unit X or electron-rich heteroaromatic groups, in particular thiophene, pyrrole or furan, as group Ar. The compound is preferably employed in a hole-transport or hole-injection layer. For the purposes of this invention, a hole-injection layer is a layer which is directly adjacent to the anode. For the purposes of this invention, a hole-transport layer is a layer which is between a hole-injection layer and an emission layer. If the compounds of the formulae (1) and (2) are used as hole-transport or hole-injection material, it may be preferred for them to be doped with electron-acceptor compounds, for example with F$_4$-TCNQ or with compounds as described in EP 1476881 or EP 1596445.

In yet a further embodiment of the invention, the compounds of the formulae (1) and (2) are employed as electron-transport material. It is preferred here for one or both bridging groups X, preferably both, to stand for C=O, P(=O), SO or SO$_2$ and for the substituents R to stand for H, an alkyl group, an aryl group or a heteroaryl group, which represents an electron-deficient heterocycle. It is furthermore preferred here for the bridging groups X to stand for C(R$^1$)$_2$ and for one or both substituents R to contain an electron-deficient heterocycle, such as, for example, imidazole, pyrazole, thiazole, benzimidazole, benzothiazole, triazole, oxadiazole, benzothiadiazole, phenanthroline, etc. This applies, in particular, to the groups X and R on the structures of the formulae (3) to (14) and (3a) to (14a) and (3b) to (14b) and (3c) to (14c). It may furthermore be preferred for the compound to be doped with electron-donor compounds.

Apart from the materials according to the invention, suitable charge-transport materials, as can be used in the hole-injection or hole-transport layer or in the electron-transport layer of the organic electroluminescent device according to the invention, are, for example, the compounds disclosed in Y. Shirota et al., *Chem. Rev.* 2007, 107(4), 953-1010, or other materials as employed in these layers in accordance with the prior art.

Suitable hole-transport or hole-injection materials which can be used in the electroluminescent device according to the invention comprising a compound of the formula (1) or (2) are, for example, the materials indicated in the following table.

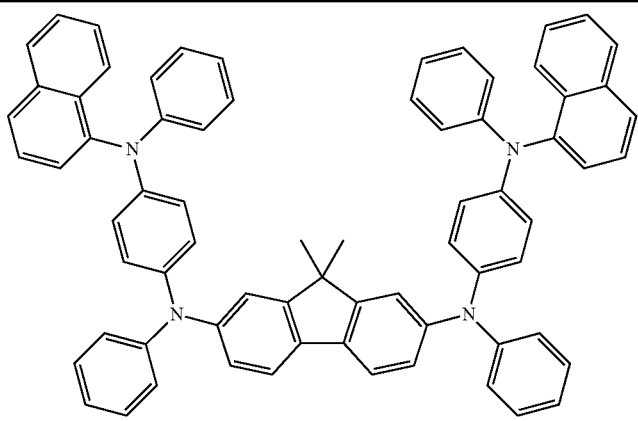

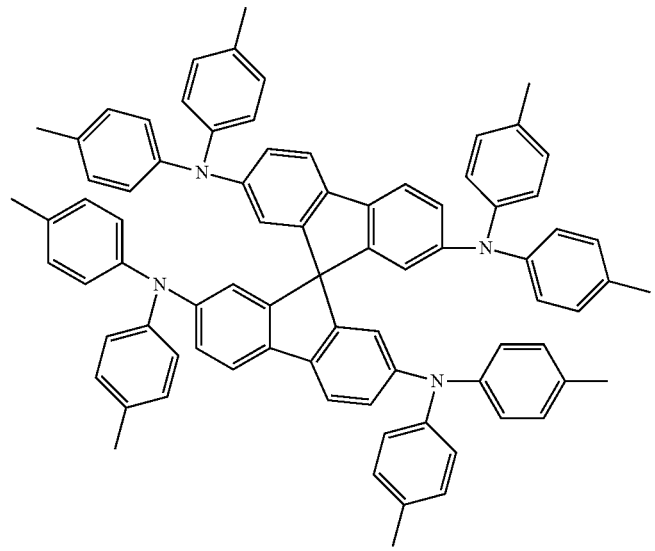
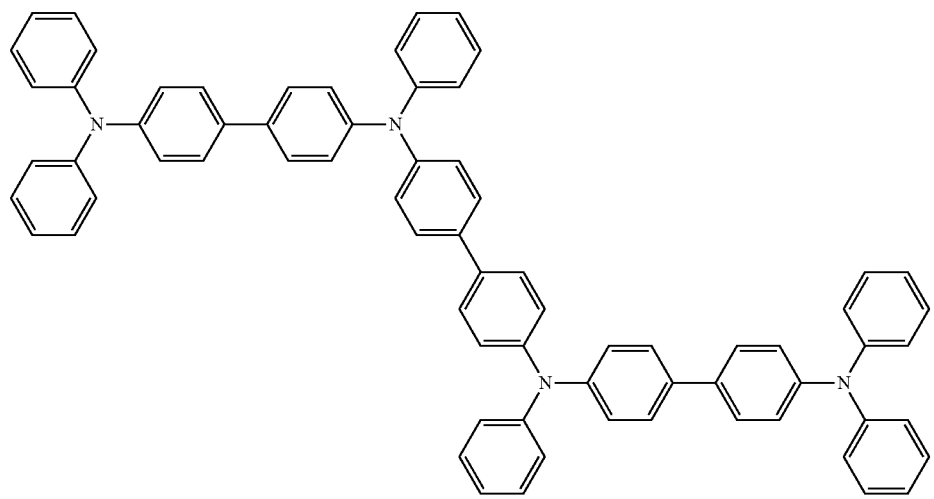 [SMILES: c1ccc(N(c2ccccc2)c2ccc(-c3ccc(N(c4ccccc4)c4ccc(-c5ccc(N(c6ccccc6)c6ccc(-c7ccc(N(c8ccccc8)c8ccccc8)cc7)cc6)cc5)cc4)cc3)cc2)cc1]
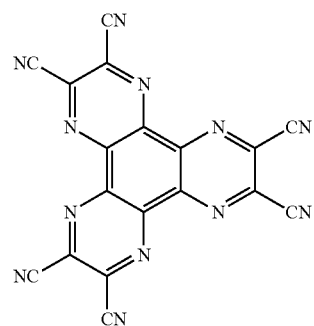 [SMILES: N#Cc1nc2c3nc(C#N)c(C#N)nc3c3nc(C#N)c(C#N)nc3c2nc1C#N]

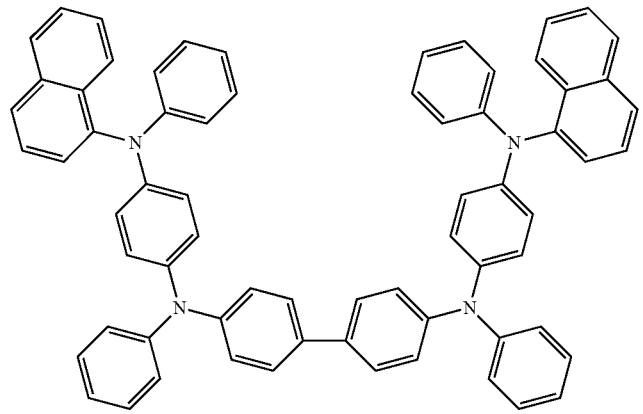 [SMILES: c1ccc(N(c2ccc(-c3ccc(N(c4ccccc4)c4ccc(N(c5ccccc5)c5cccc6ccccc56)cc4)cc3)cc2)c2ccc(N(c3ccccc3)c3cccc4ccccc34)cc2)cc1]
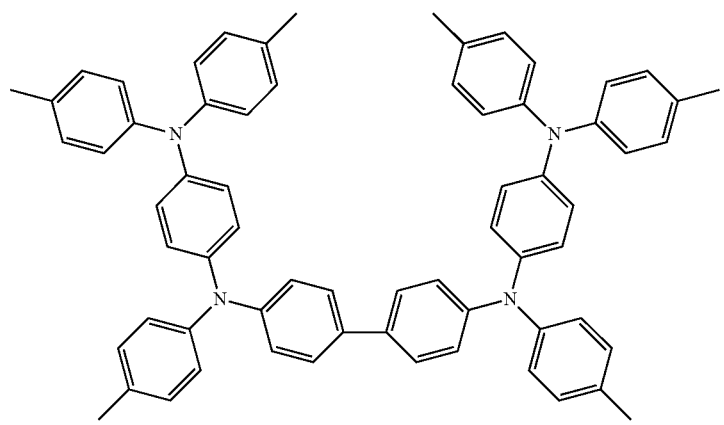
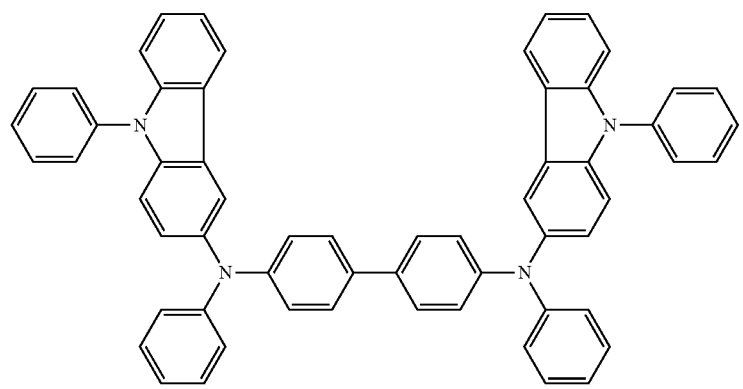 [SMILES: c1ccc(N(c2ccc(-c3ccc(N(c4ccccc4)c4ccc5c(c4)c4ccccc4n5-c4ccccc4)cc3)cc2)c2ccc3c(c2)c2ccccc2n3-c2ccccc2)cc1]

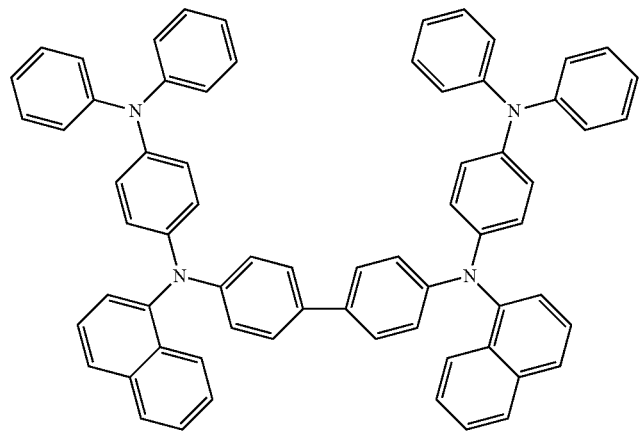 [SMILES: c1ccc(N(c2ccccc2)c2ccc(N(c3ccc(-c4ccc(N(c5ccc(N(c6ccccc6)c6ccccc6)cc5)c5cccc6ccccc56)cc4)cc3)c3cccc4ccccc34)cc2)cc1]
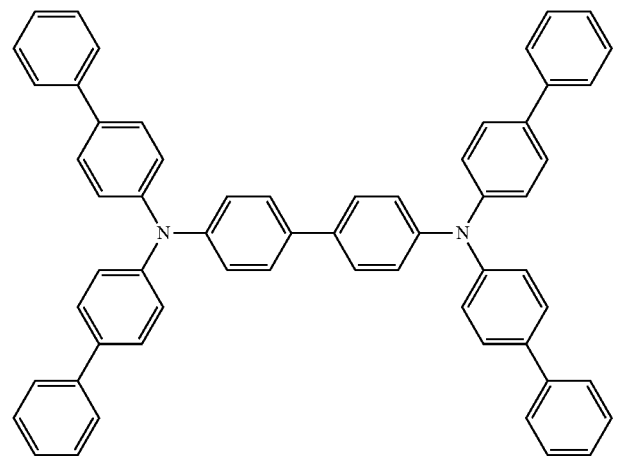 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]
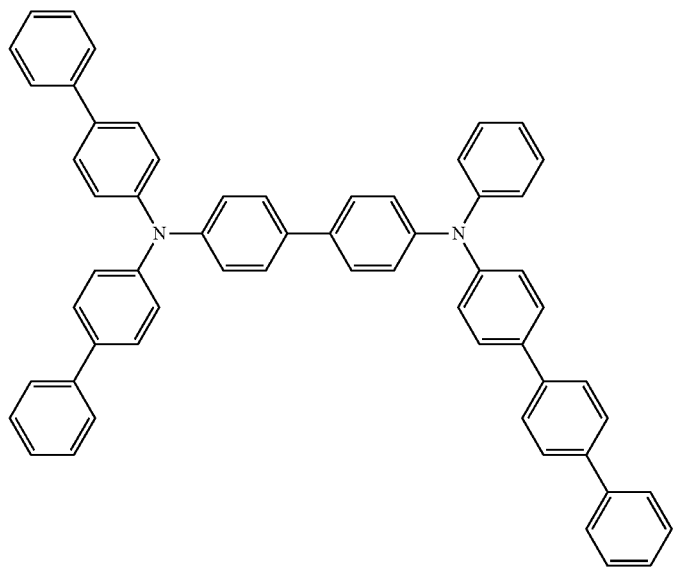 [SMILES: c1ccc(-c2ccc(-c3ccc(N(c4ccccc4)c4ccc(-c5ccc(N(c6ccc(-c7ccccc7)cc6)c6ccc(-c7ccccc7)cc6)cc5)cc4)cc3)cc2)cc1]

-continued
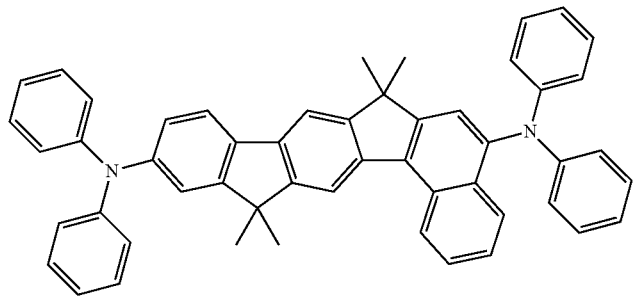 [SMILES: CC1(C)c2cc(N(c3ccccc3)c3ccccc3)ccc2-c2cc3c(cc21)-c1c(cc(N(c2ccccc2)c2ccccc2)c2ccccc12)C3(C)C]
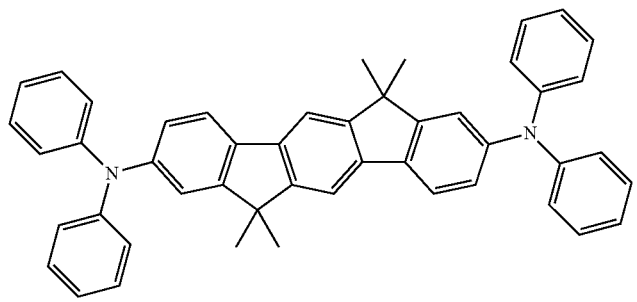 [SMILES: CC1(C)c2cc(N(c3ccccc3)c3ccccc3)ccc2-c2cc3c(cc21)-c1ccc(N(c2ccccc2)c2ccccc2)cc1C3(C)C]
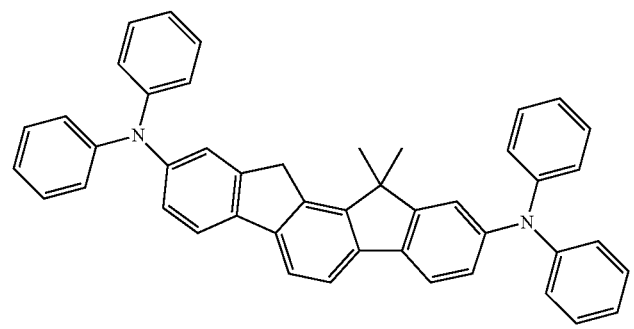 [SMILES: CC1(C)c2cc(N(c3ccccc3)c3ccccc3)ccc2-c2ccc3c(c21)Cc1cc(N(c2ccccc2)c2ccccc2)ccc1-3]
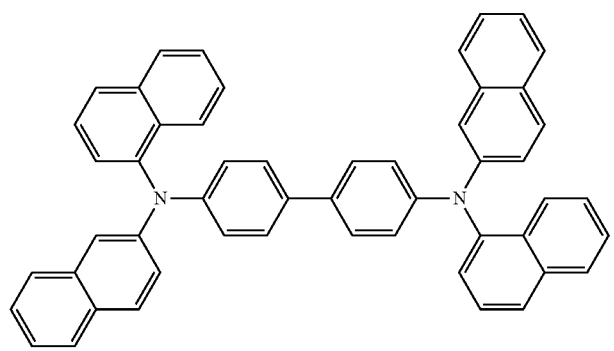 [SMILES: c1ccc2cc(N(c3ccc(-c4ccc(N(c5ccc6ccccc6c5)c5cccc6ccccc56)cc4)cc3)c3cccc4ccccc34)ccc2c1]
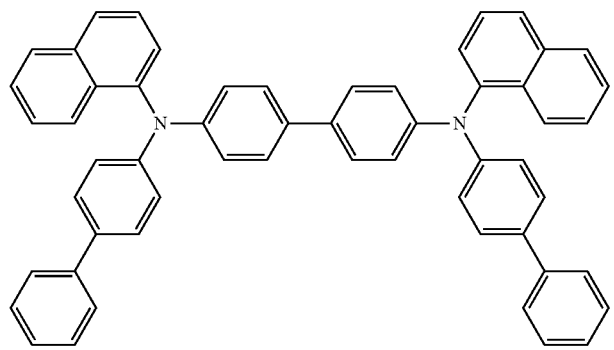 [SMILES: c1ccc(-c2ccc(N(c3ccc(-c4ccc(N(c5ccc(-c6ccccc6)cc5)c5cccc6ccccc56)cc4)cc3)c3cccc4ccccc34)cc2)cc1]

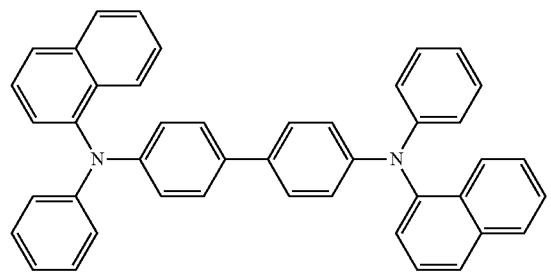 [SMILES: c1ccc(N(c2ccc(-c3ccc(N(c4ccccc4)c4cccc5ccccc45)cc3)cc2)c2cccc3ccccc23)cc1]
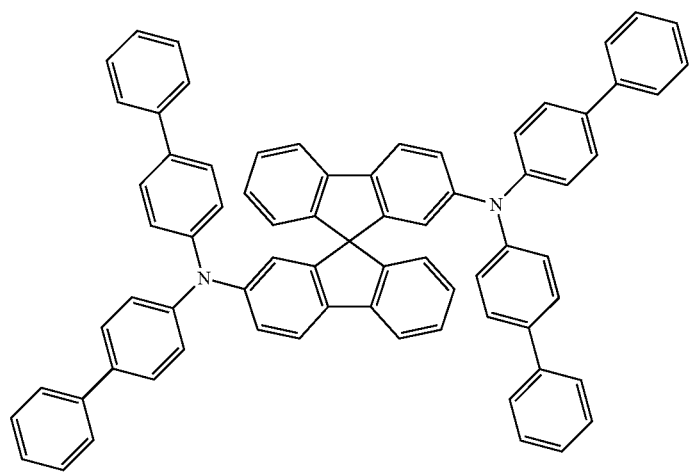 [SMILES: c1ccc(-c2ccc(N(c3ccc(-c4ccccc4)cc3)c3ccc4c(c3)C3(c5ccccc5-4)c4ccccc4-c4ccc(N(c5ccc(-c6ccccc6)cc5)c5ccc(-c6ccccc6)cc5)cc43)cc2)cc1]
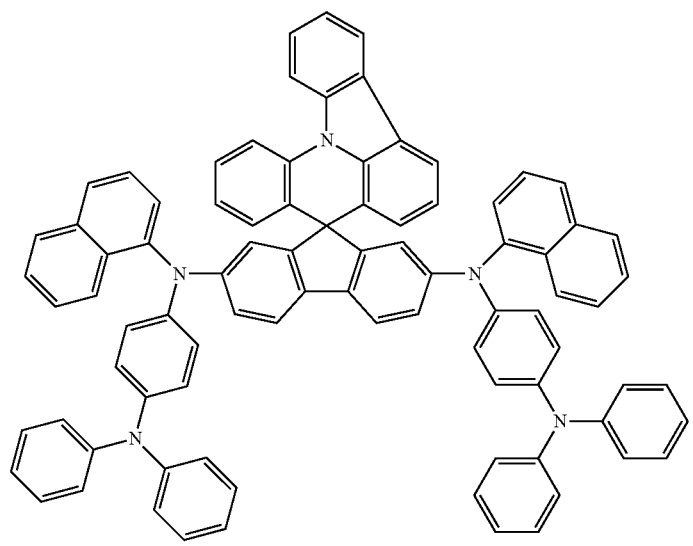 [SMILES: c1ccc(N(c2ccccc2)c2ccc(N(c3ccc4c(c3)C3(c5cc(N(c6ccc(N(c7ccccc7)c7ccccc7)cc6)c6cccc7ccccc67)ccc5-4)c4ccccc4-n4c5ccccc5c5cccc3c54)c3cccc4ccccc34)cc2)cc1]

Further suitable hole-transport and hole-injection materials are derivatives of the compounds depicted above, as disclosed in JP 2001/226331, EP 676461, EP 650955, WO 01/049806, U.S. Pat. No. 4,780,536, WO 98/30071, EP 891121, EP 1661888, JP 2006/253445, EP 650955, WO 06/073054, U.S. Pat. No. 5,061,569 and WO 06/122630.

Suitable electron-transport or electron-injection materials which can be used in the electroluminescent device according to the invention comprising a compound of the formula (1) or (2) are, for example, the materials indicated in the following table.

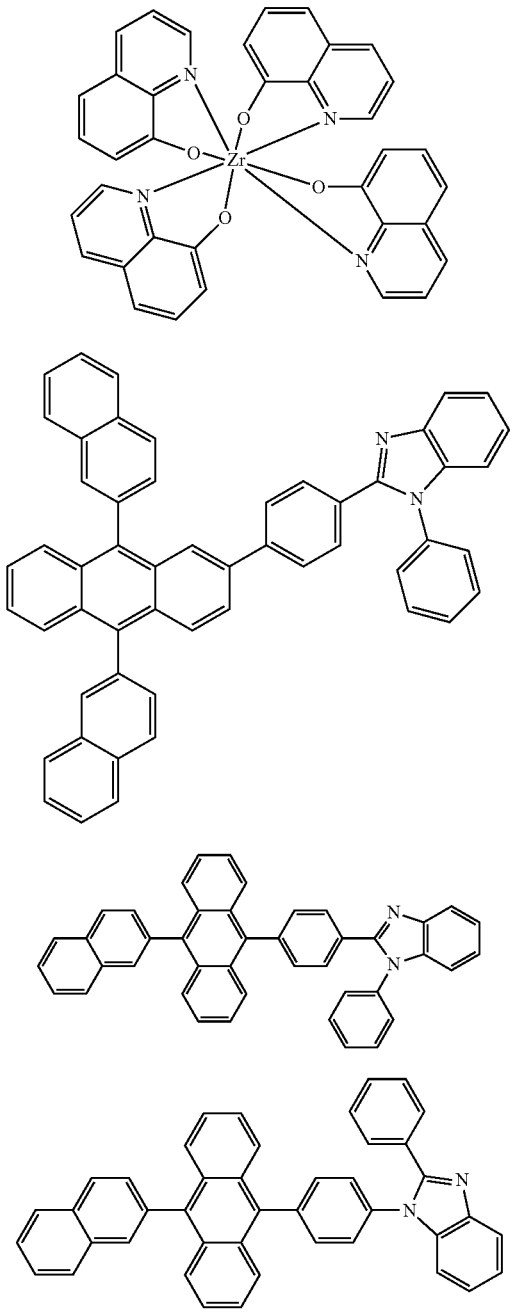

Further suitable electron-transport and electron-injection materials are derivatives of the compounds depicted above, as disclosed in JP 2000/053957, WO 03/060956, WO 04/028217 and WO 04/080975.

Recurring units of the formulae (1) and (2) can also be employed in polymers, either as polymer backbone, as emitting unit, as hole-transporting unit and/or as electron-transporting unit. The preferred substitution patterns here correspond to those described above.

Preference is furthermore given to an organic electroluminescent device, characterised in that one or more layers are applied by a sublimation process, in which the materials are vapour-deposited in vacuum sublimation units at an initial pressure of usually less than $10^{-5}$ mbar, preferably less than $10^{-6}$ mbar. However, it is also possible for the initial pressure to be even lower, for example less than $10^{-7}$ mbar.

Preference is likewise given to an organic electroluminescent device, characterised in that one or more layers are applied by the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or ink-jet printing. Soluble compounds are necessary for this purpose. High solubility can be achieved through suitable substitution of the compounds.

On use in organic electroluminescent devices, the compounds according to the invention have the following surprising advantages over the prior art:

1. The compounds according to the invention have high thermal stability and can be sublimed without decomposition.
2. The compounds according to the invention, in particular those in which R stands for an aromatic or heteroaromatic ring system or which are substituted by diarylamino substituents, have very good blue or green coordinates and are therefore very highly suitable as blue emitters. Furthermore, the compounds have a low Stokes shift and a very narrow emission spectrum.
3. The compounds according to the invention are very highly suitable as host material, in particular for red- and green-fluorescing dopants.
4. The compounds according to the invention, in particular those which are substituted by diarylamino groups and/or which contain S, O or $N(R^1)$ in the bridge X and/or which contain electron-rich heteroaromatic groups as group Ar, are very highly suitable for use as hole-injection and hole-transport material and result in a reduction in the operating voltage.
5. The OLEDs produced using the compounds according to the invention have a very long lifetime.
6. The OLEDs produced using the compounds according to the invention have very high quantum efficiency.

The present application text is directed to the use of the compounds according to the invention in relation to OLEDs and PLEDs and the corresponding displays. In spite of this restriction of the description, it is possible for the person skilled in the art, without further inventive step, also to employ the compounds according to the invention in other electronic devices, for example in organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic laser diodes (O-lasers) or organic photo receptors.

The present invention likewise relates to the use of the compounds according to the invention in the corresponding devices and to these devices themselves.

The invention is described in greater detail by the following examples without wishing to restrict it thereby.

EXAMPLES

The following syntheses are carried out under a protective-gas atmosphere in dried solvents, unless indicated otherwise. The starting materials can be purchased from ALDRICH.

Example 1

2,3,8,9-Dibenzo-1,1,7,7-tetraphenyl-5,11-diphenyl-1,7-dihydrodicyclopenta[b,i]anthracene a) Synthesis of 2,6-dibromoanthraquinone (Lee et al., *Organic Letters* 2005, 7(2), 323-326)

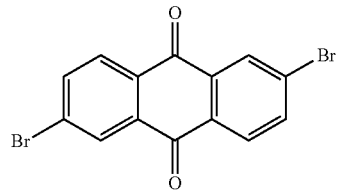 [SMILES: O=C1c2ccc(Br)cc2C(=O)c2ccc(Br)cc21]

62.6 g (255 mmol) of 2,6-diaminoanthraquinone and 124 g (550 mmol) of $CuBr_2$ are initially introduced in 1000 ml of acetonitrile, and 68 ml (515 mmol) of tert-butyl nitrite are added dropwise at an internal temperature of 60° C. After 30 min., the reaction mixture is poured into a mixture of 150 ml of concentrated HCl and 1 l of ice-water, and the solid formed is filtered off with suction, washed with water, EtOH and heptane and dried, giving 89 g (243 mmol, 96%) of a brown solid, which is homogeneous in the $^1$H-NMR and which is employed in the subsequent reaction without further purification.

b) Synthesis of 2,6-dibromo-9,10-diphenylanthracene

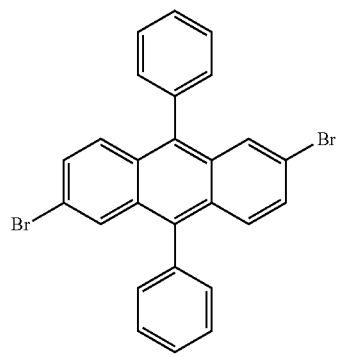 [SMILES: Brc1ccc2c(-c3ccccc3)c3cc(Br)ccc3c(-c3ccccc3)c2c1]

36.6 g (100 mmol) of 2,6-dibromoanthraquinone are dissolved in 600 ml of THF, the solution is cooled to −75° C., and 100 ml of a 2 M phenyllithium solution in THF are added dropwise. After 2 h, the mixture is allowed to come to RT, 50 ml of 4 M HCl are added, the mixture is partitioned between toluene and water, the organic phase is dried over $Na_2SO_4$, and the solvent is removed in vacuo. The residue is taken up in 350 ml of DMF, 68 g (350 mmol) of $SnCl_2$ are added, and the mixture is brought to an internal temperature of 140° C. for 2 h. 180 ml of 2 M HCl are then added at about 40° C., and the precipitate is filtered off with suction, washed with water, EtOH and ethyl acetate and dried at 80° C. in vacuo. Recrystallisation from toluene gives 30.8 g (63 mmol, 63%) of an ochre solid, which is homogeneous according to TLC and $^1$H-NMR and is employed in this form in the subsequent reaction.

c) Synthesis of 9,10-diphenylanthracene-2,6-diboronic acid pinacol ester

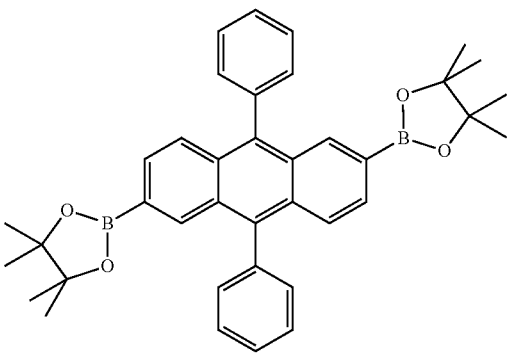

9.5 g (19.5 mmol) of 2,6-dibromo-9,10-diphenylanthracene are dissolved in 240 ml of dry dioxane, 16.3 g (64 mmol) of bis(pinacolato)diboron, 1 g (1.2 mmol) of [1,1'-bis(diphenylphosphino)ferrocene]palladium(II) chloride (complex with dichloromethane (1:1), Pd content: 13%) and 23 g (234 mmol) of potassium acetate are added, the mixture is heated at the boil for 2 h and poured into ice-water, and the precipitate is filtered off with suction, washed with EtOH and dried in vacuo, giving 10 g (17.1 mmol, 88%) of a pale-yellow powder which is homogeneous according to TLC and $^1$H-NMR.

d) Synthesis of 9,10-diphenyl-2,6-(2-carboxymethylphenyl)anthracene

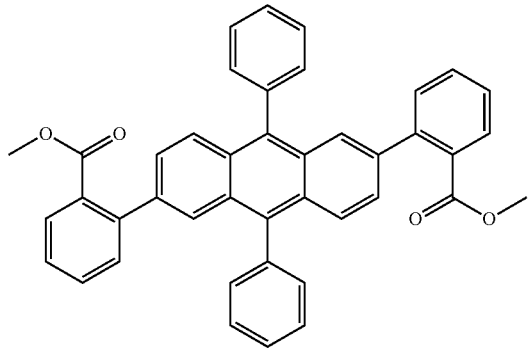

9.4 g (16 mmol) of 9,10-diphenylanthracene-2,6-diboronic acid pinacol ester are heated at the boil for 4 h in a mixture of 115 ml of EtOH, 115 ml of toluene, 60 ml of a 2 M Na$_2$CO$_3$ solution, 4.5 ml (32.3 mmol) of methyl 2-bromobenzoate and 750 mg (0.7 mmol) of Pd(PPh$_3$)$_4$. The reaction mixture is subsequently poured into a mixture of ice-water/MeOH/HCl 1:1:1, and the colourless precipitate is filtered off with suction, washed with water, EtOH and heptane and dried. The solid is dissolved in boiling toluene, the solution is filtered through a layer of silica gel, heptane is added to the filtrate, and the precipitated product is filtered off with suction, giving 8.9 g (14.8 mmol, 92%) of the diester as a colourless powder.

e) Synthesis of (2-{6-[2-(hydroxydiphenylmethyl)phenyl]-9,10-diphenylanthracen-2-yl}phenyl)diphenylmethanol

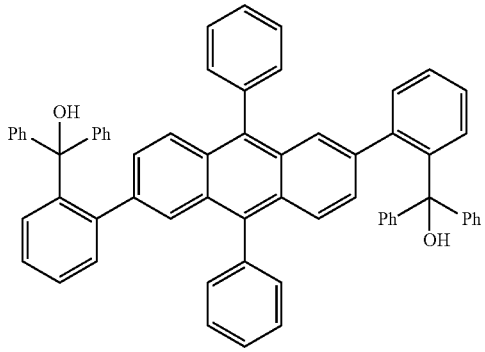 [SMILES: OC(c1ccccc1)(c1ccccc1)c1ccccc1-c1ccc2c(-c3ccccc3)c3cc(-c4ccccc4C(O)(c4ccccc4)c4ccccc4)ccc3c(-c3ccccc3)c2c1]

180 ml of a 0.5 M phenylmagnesium bromide solution (90 mmol) in THF are added at RT to 8.9 g (14.9 mmol) of the diester, and the mixture is heated at the boil for 3 h. After this time, 50 ml of 50% acetic acid are added dropwise, the solvent is removed in vacuo, and the solid remaining is taken up in MeOH, filtered off with suction and washed with MeOH and dried, leaving 11.3 g (13.3 mmol, 90%) of a colourless solid, which, according to TLC and $^1$H-NMR, has a degree of purity of >98%.

f) Synthesis of dibenzo-1,1,7,7-tetraphenyl-5,11-diphenyl-1,7-dihydrodicyclopenta[b,i]anthracene

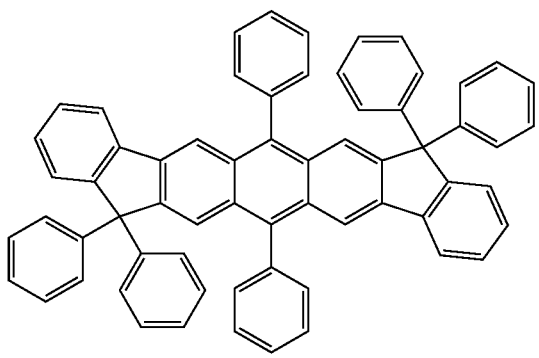 [SMILES: c1ccc(-c2c3cc4c(cc3c(-c3ccccc3)c3cc5c(cc23)C(c2ccccc2)(c2ccccc2)c2ccccc2-5)C(c2ccccc2)(c2ccccc2)c2ccccc2-4)cc1]

10.3 g (12.2 mmol) of the diol are heated at the boil for 2 h in a mixture of 70 ml of glacial acetic acid and 1 ml of conc. HCl. When the reaction is complete, the precipitated solid is filtered off with suction, washed with water, EtOH and heptane and dried. After recrystallisation four times from chlorobenzene and sublimation twice in vacuo (T=340° C., p=1×10$^{-5}$ mbar), 6 g (7.4 mmol, 61%) remain in the form of a pale-yellow glass having a purity, determined by RP-HPLC, of >99.9%.

Example 2

2,3-Benzo-1,1-diphenyl-5,11-diphenyl-1-dihydrocyclopenta[b]anthracene

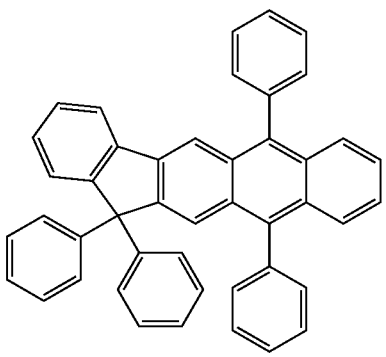 [SMILES: c1ccc(-c2c3ccccc3c(-c3ccccc3)c3cc4c(cc23)-c2ccccc2C4(c2ccccc2)c2ccccc2)cc1]

The synthesis of this compound is carried out analogously to Example 1, with 2-aminoanthraquinone being employed as starting compound.

Example 3

Production of OLEDs

OLEDs are produced by a process which is described in general terms in WO 04/058911 and which is adapted in individual cases to the respective circumstances (for example layer-thickness variation in order to achieve optimum efficiency or colour).

The results for various OLEDs are presented in Examples 4 to 7 below. Glass plates which are coated with structured ITO (indium tin oxide) form the substrates of the OLEDs. The OLEDs consist of the following layer sequence: substrate/hole-injection layer (HTM1) 60 nm/hole-transport layer (HTM2) 20 nm/emission layer (EML) 30 nm/electron-transport layer (ETM) 20 nm and finally a cathode. The materials are vapour-deposited thermally in a vacuum chamber. The emission layer here always consists of a matrix material (host) and a dopant, which is admixed with the host by co-evaporation. The cathode is formed by a 1 nm thin LiF layer and a 100 nm Al layer deposited on top.

Table 1 shows the chemical structures of the materials used to build up the OLEDs.

These OLEDs are characterised by standard methods; for this purpose, the electroluminescence spectra, the efficiency (measured in cd/A), the power efficiency (measured in lm/W) as a function of the luminance, calculated from current-voltage-luminance characteristic lines (IUL characteristic lines), and the lifetime are determined. The lifetime is defined as the time after which the initial luminance of 25,000 cd/m$^2$ has dropped to half. The half-value width (FWHM=full width half maximum) is determined from the electroluminescence spectra.

Table 1 shows the results for some OLEDs (Examples 4 to 7). The host materials and emitter materials according to the invention are the compounds from Examples 1 and 2. Host H1 and emitter material D1 in accordance with the prior art are used as comparative examples.

As can clearly be seen from the results in Table 2, organic electroluminescent devices comprising the compounds according to the invention have a longer lifetime in the case of the matrix example. As can be seen from Table 3, organic electroluminescent devices comprising the compounds according to the invention as dopants have a significantly improved half-value width compared with the prior art.

TABLE 1

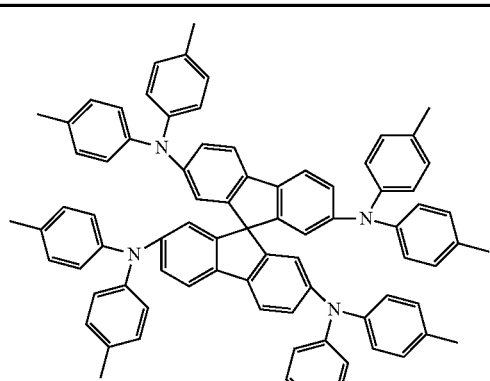

HTM1

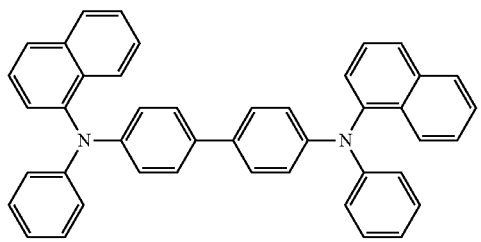 [SMILES: c1ccc(N(c2ccc(-c3ccc(N(c4ccccc4)c4cccc5ccccc45)cc3)cc2)c2cccc3ccccc23)cc1]

HTM 2

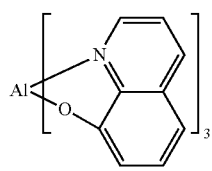

ETM1

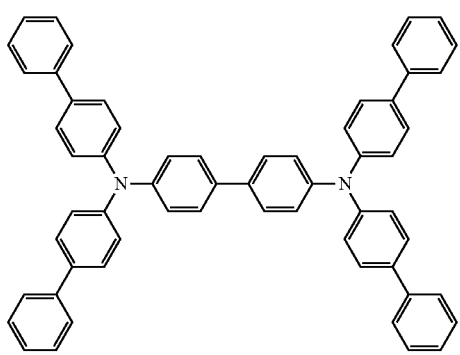 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]

HTM 3

TABLE 1-continued

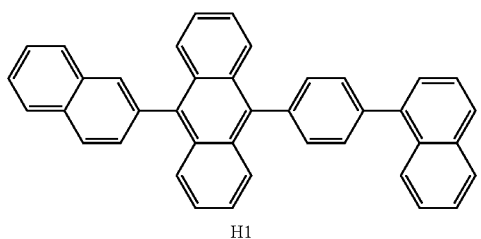

H1

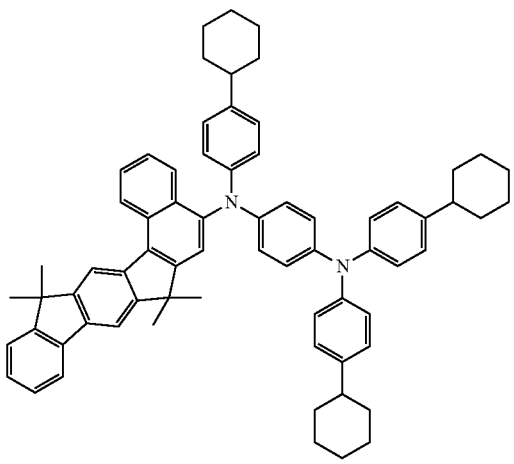 [SMILES: CC1(C)c2ccccc2-c2cc3c(cc21)-c1c(cc(N(c2ccc(C4CCCCC4)cc2)c2ccc(N(c4ccc(C5CCCCC5)cc4)c4ccc(C5CCCCC5)cc4)cc2)c2ccccc12)C3(C)C]

D1

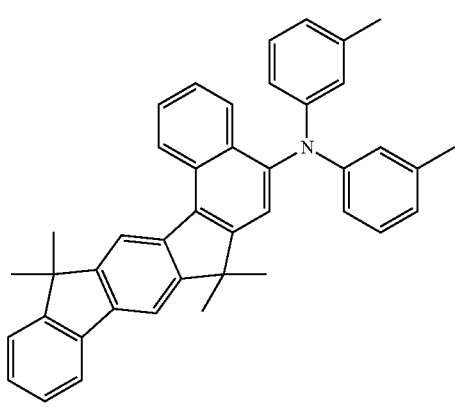 [SMILES: Cc1cccc(N(c2cccc(C)c2)c2cc3c(c4ccccc24)-c2cc4c(cc2C3(C)C)-c2ccccc2C4(C)C)c1]

D2

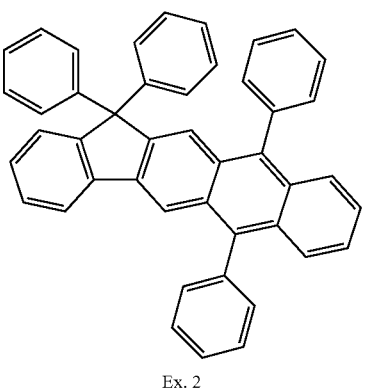

Ex. 2

TABLE 1-continued

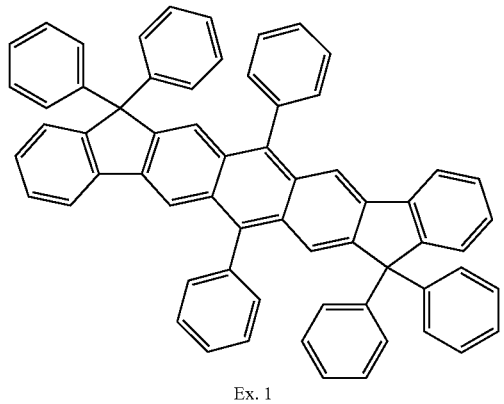

Ex. 1 formula (2)

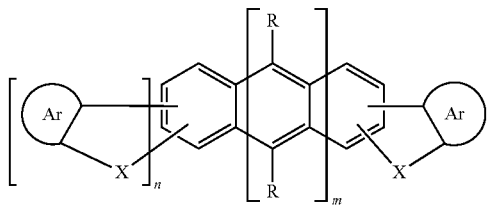

TABLE 2

| Ex. | EML | ETM | Colour | Max. eff. (cd/A) | Voltage (V) at 1000 cd/m² | CIE | Lifetime at 25000 cd/m² (h) |
|---|---|---|---|---|---|---|---|
| 4 comparison | H1 + 5% of D1 | ETM1 | green | 18.3 | 5.3 | x = 0.29/ y = 0.60 | 300 |
| 5 | Ex. 2 + 5% of D1 | ETM1 | green | 22.5 | 4.9 | x = 0.29/ y = 0.62 | 410 |

TABLE 3

| Ex. | EML | ETM | Colour | Max. eff. (cd/A) | Voltage (V) at 1000 cd/m² | CIE | FWHM |
|---|---|---|---|---|---|---|---|
| 6 comparison | H1 + 5% of D2 | ETM1 | blue | 3.9 | 5.7 | x = 0.14/ y = 0.12 | 49 |
| 7 | H1 + 1% of Ex. 1 | ETM1 | blue | 3.1 | 5.7 | x = 0.14/ y = 0.09 | 24 |

The significantly narrower half-value width of the emission peak is illustrated in FIG. 1. The photoluminescence spectra and the half-value width of compound D2 depicted above (dotted line; compound in accordance with WO 08/006,449) with the compound according to the invention from Ex. 1 (solid line) in toluene are depicted here.

The invention claimed is:

1. A compound of the formulae (1) and (2):

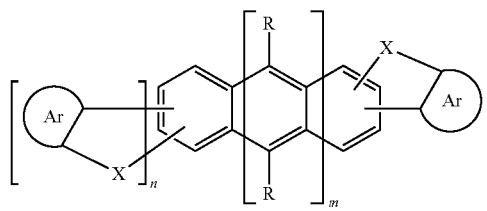

formula (1)

in which one or more unsubstituted carbon atoms in the anthracene unit optionally is replaced by nitrogen;

X is, on each occurrence, identically or differently, a $C(R^1)_2$;

Ar is on each occurrence, identically or differently, an aryl group having 6 to 40 C atoms or a heteroaryl group having 2 to 40 C atoms, each of which is optionally substituted by one or more radicals $R^2$;

$R^1$ is on each occurrence, identically or differently, a straight-chain alkyl having 1 to 5 C atoms or a branched or cyclic alkyl, alkoxy or thioalkoxy group having 3 to 5 carbons where one or more non-adjacent $CH_2$ groups is optionally replaced by $R^3C=CR^3$, $C\equiv C$, or —O— and where one or more H atoms is optionally replaced by F, an aryl group having 6 to 16 C atoms or a heteroaryl group having 2 to 16 C atoms, each which may in each case be substituted by one or more radicals $R^2$, or a combination of two or three of these systems two of the radicals $R^1$ which are bonded in the same bridge atom may also form a ring system with one another here;

R is on each occurrence, identically or differently, an aromatic or heteroaromatic ring system having 5 to 16 aromatic ring atoms, each of which may be substituted by one or more radicals $R^2$;

$Ar^1$ is on each occurrence, identically or differently, an aromatic or heteroaromatic ring system having 5 to 30 aromatic ring atoms, which is optionally substituted by one or more radicals $R^2$; two radicals Ar here which are bonded to the same nitrogen or phosphorus atom is optionally linked to one another by a single bond or a bridge selected from the group consisting of $B(R^3)$, $C(R^3)_2$, $Si(R^3)_2$, $C=O$, $C=NR^3$, $C=C(R^3)_2$, O, S, $S=O$, $SO_2$, $N(R^3)$, $P(R^3)$ and $P(=O)R^3$;

R² is on each occurrence, identically or differently, H, D, F, Cl, Br, I, CHO, N(R³)₂, N(Ar¹)₂, C(=O)Ar¹, P(=O)(Ar¹)₂, S(=O)Ar¹, S(=O)₂Ar¹, CR³=CR³Ar¹, CN, NO₂, Si(R³)₃, B(OR³)₂, OSO₂R³, a straight-chain alkyl, alkoxy or thioalkoxy group having 1 to 40 C atoms or a branched or cyclic alkyl, alkenyl, alkynyl, alkoxy or thioalkoxy group having 3 to 40 C atoms, each of which is optionally substituted by one or more radicals R³, where one or more non-adjacent CH₂ groups is optionally replaced by R³C=CR³, C≡C, Si(R³)₂, Ge(R³)₂, Sn(R³)₂, C=O, C=S, C=Se, C=NR², P(=O)(R³), SO, SO₂, NR³, O, S or CONR³ and where one or more H atoms is optionally replaced by F, Cl, Br, I, CN or NO₂, or a combination of these systems; two or more adjacent substituents R² here optionally form a mono- or polycyclic, aliphatic or aromatic ring system with one another;

R³ is on each occurrence, identically or differently, H, D, F or an aliphatic, aromatic and/or heteroaromatic hydrocarbon radical having 1 to 20 C atoms, in which, in addition, H atoms is optionally replaced by F; two or more adjacent substituents R² here optionally form a mono- or polycyclic, aliphatic or aromatic ring system with one another;

m is 1; and n is 0 or 1.

2. The compound according to claim 1, wherein the compound is of the formulae (3) to (15):

formula (3)

formula (4)

formula (5)

formula (6)

formula (7)

formula (8)

formula (9)

formula (10)

formula (11)

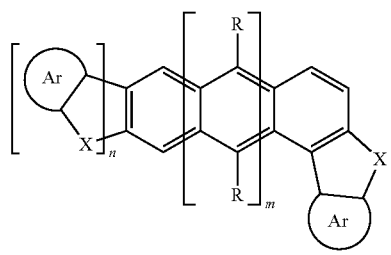
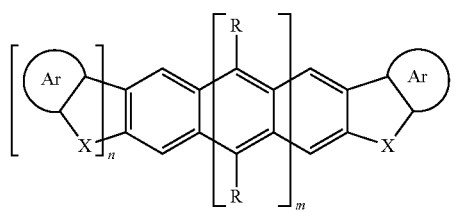
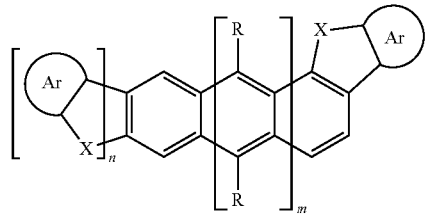
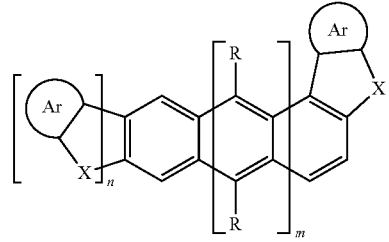
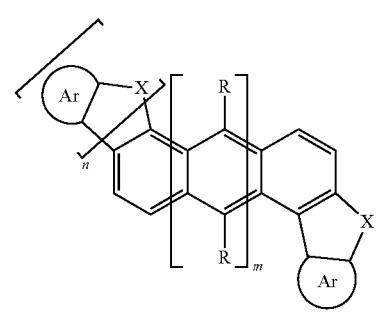
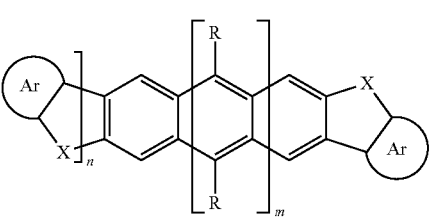
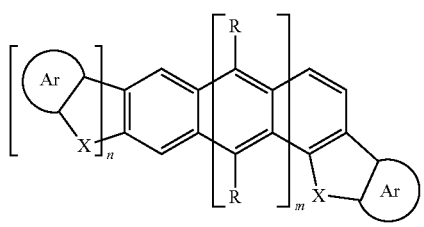
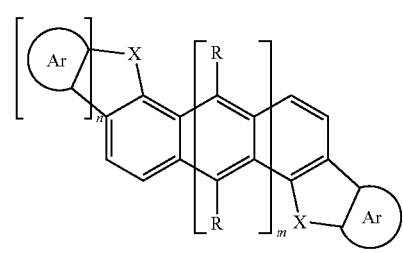
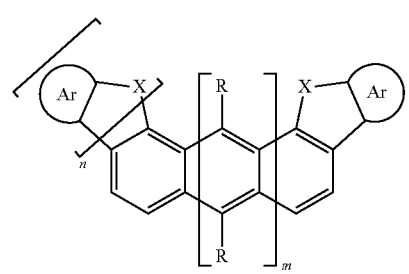

formula (12)

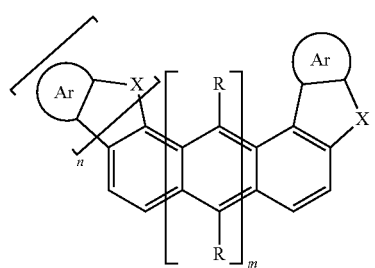

formula (13)

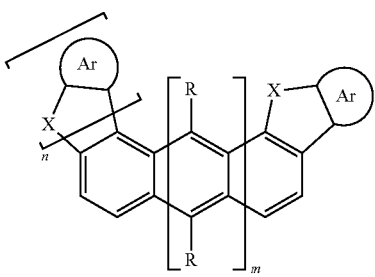

formula (14)

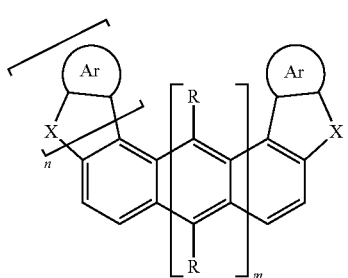

formula (15)

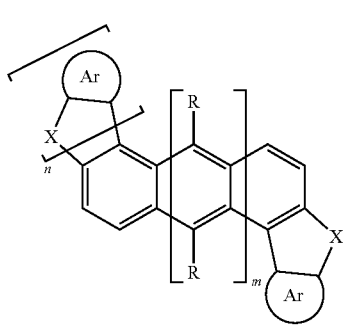

where one or more unsubstituted carbon atoms in the anthracene unit is optionally replaced by nitrogen.

3. The compound according to claim 1, wherein the symbol Ar stands, identically or differently on each occurrence, for an aryl group having 6 to 16 C atoms or for a heteroaryl group having 2 to 16 C atoms, each of which is optionally substituted by one or more radicals $R^2$.

4. The compound according to claim 1, wherein the symbol Ar stands, identically or differently on each occurrence, for benzene, naphthalene, thiophene, pyrrole, furan, pyridine, pyrimidine, pyrazine, pyridazine, quinoline, quinoxaline, benzothiophene, indole or benzofuran.

5. The compound according to claim 1, wherein in the compound is of the formulae (3a) to (15a), (3b) to (15b) and (3c) to (15c):

formula (3a)

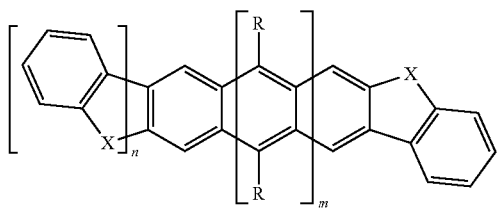

formula (4a)

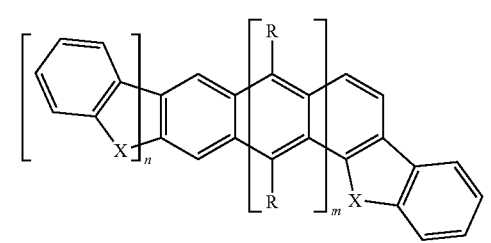

formula (5a)

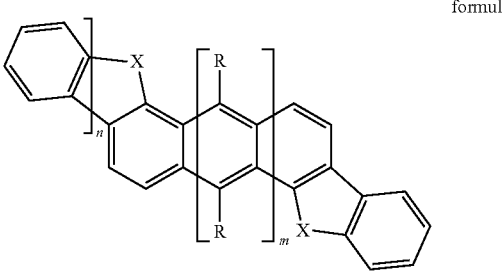

formula (6a)

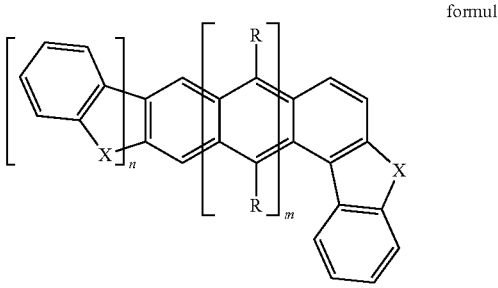

formula (7a)

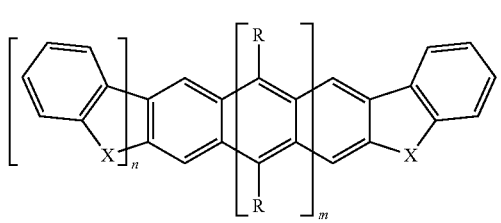

formula (8a)

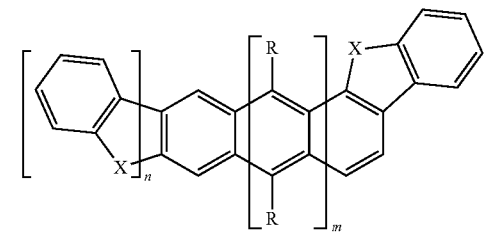

formula (9a)
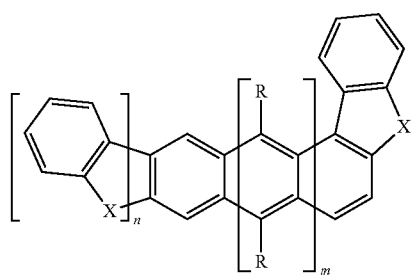
formula (10a)
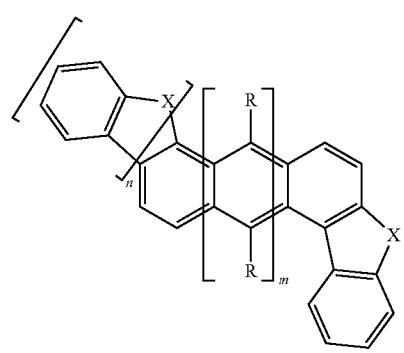
formula (11a)
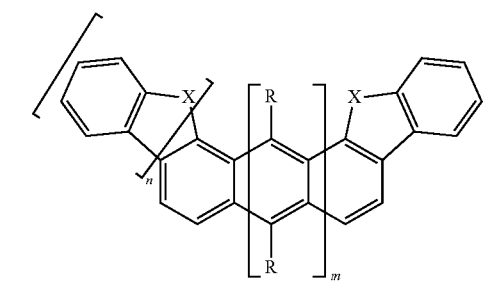
formula (12a)
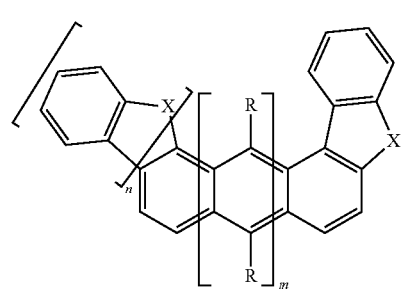
formula (13a)
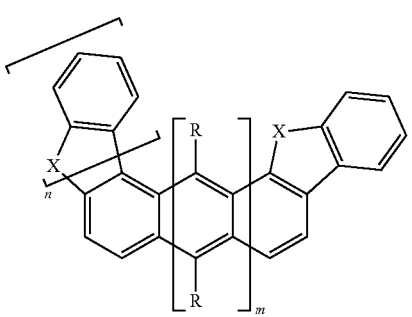
formula (14a)
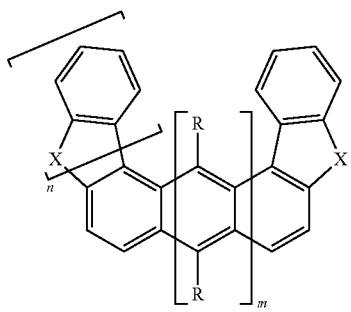
formula (15a)
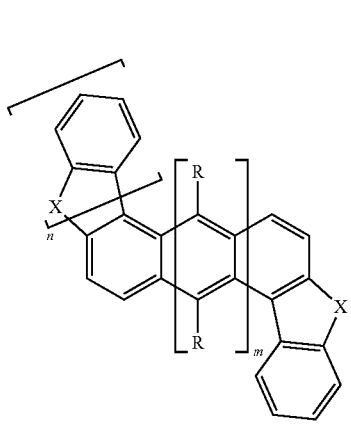
formula (3b)
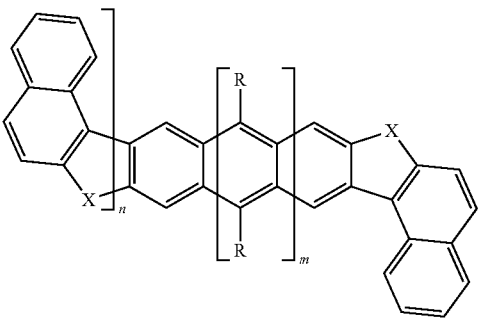
formula (4b)
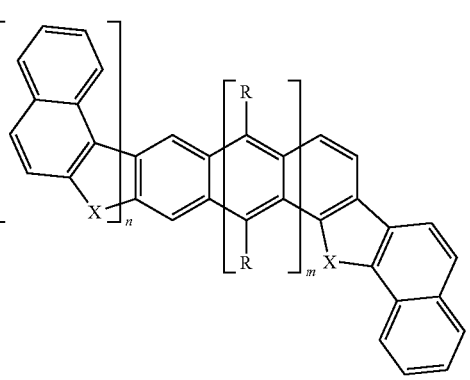

formula (5b)
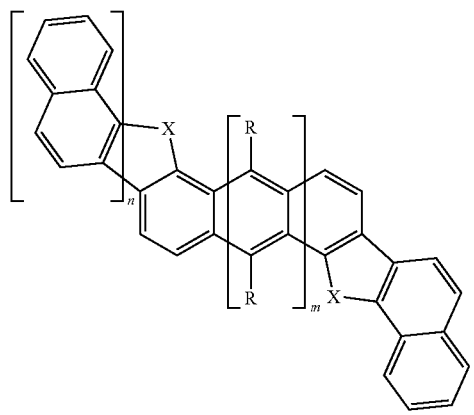
formula (6b)
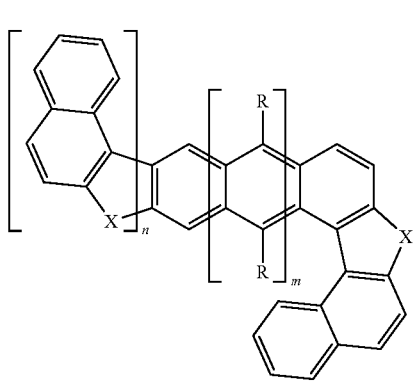
formula (7b)
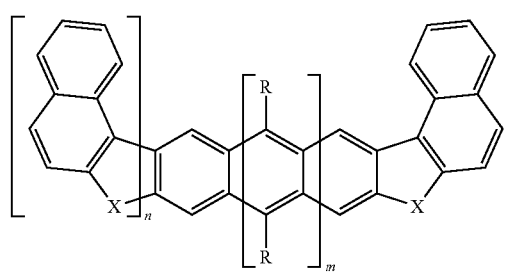
formula (8b)
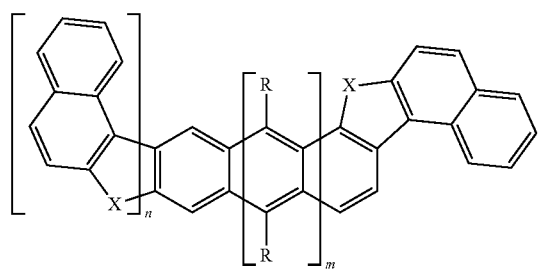
formula (9b)
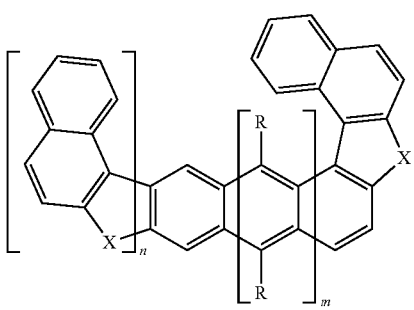
formula (10b)
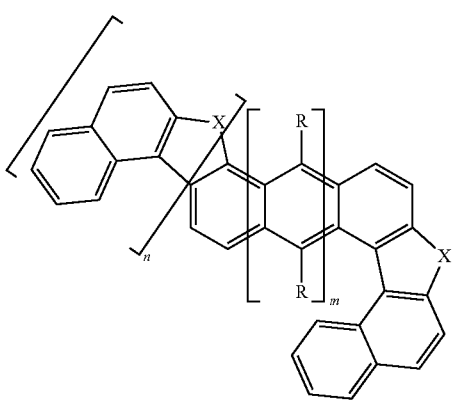
formula (11b)
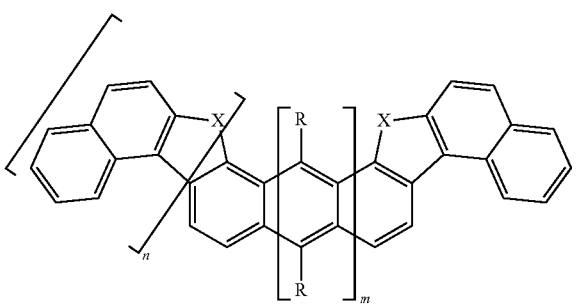
formula (12b)
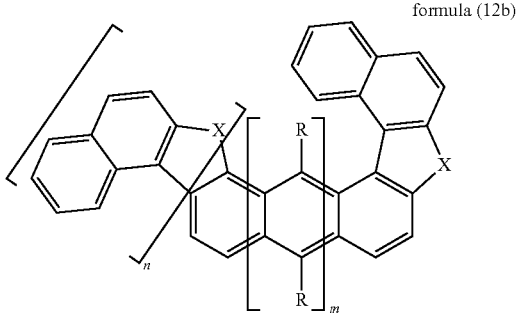

-continued
formula (13b)
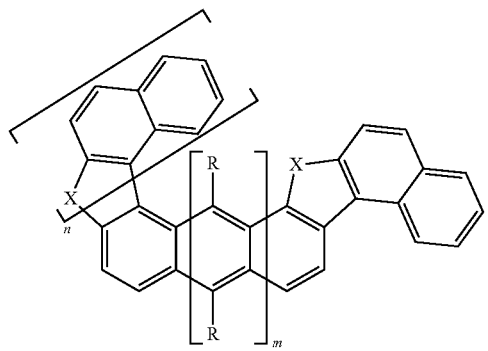
formula (14b)
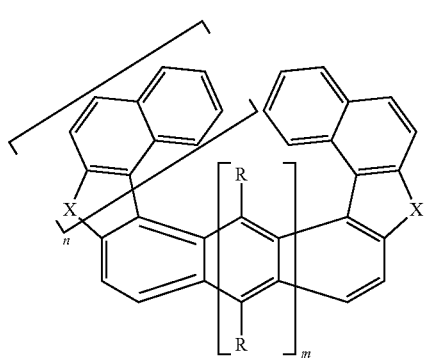
formula (15b)
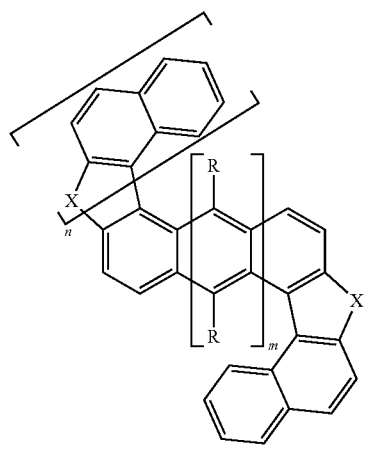
formula (3c)
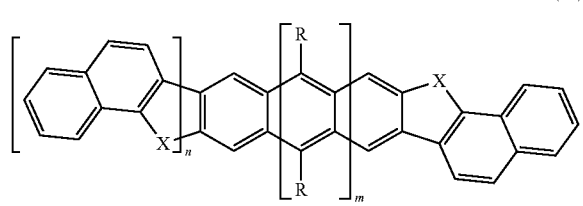
-continued
formula (4c)
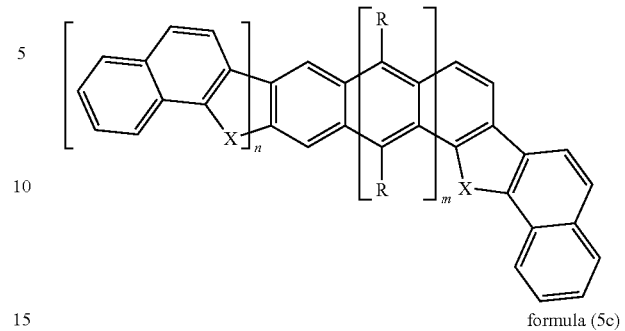
formula (5c)
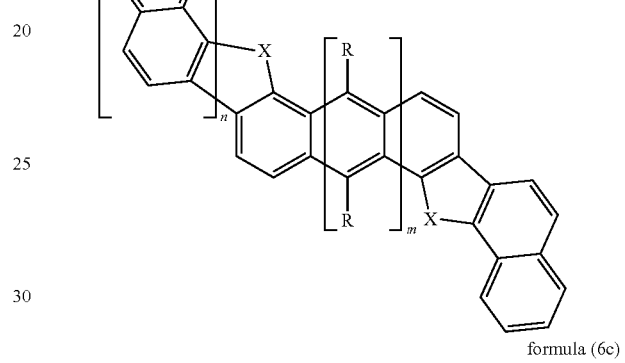
formula (6c)
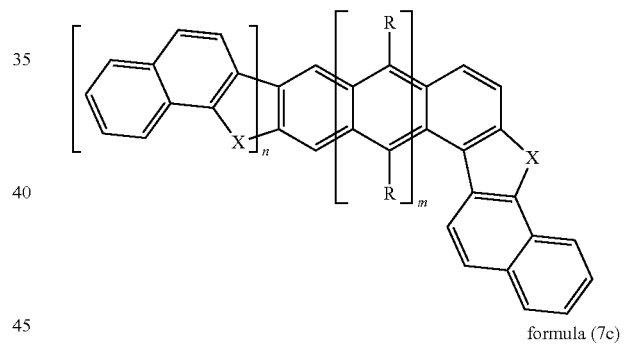
formula (7c)
formula (8c)
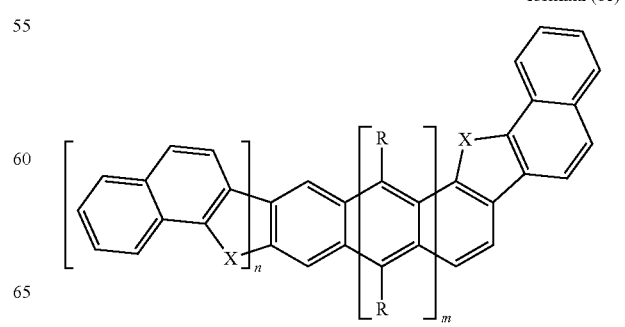

formula (9c)

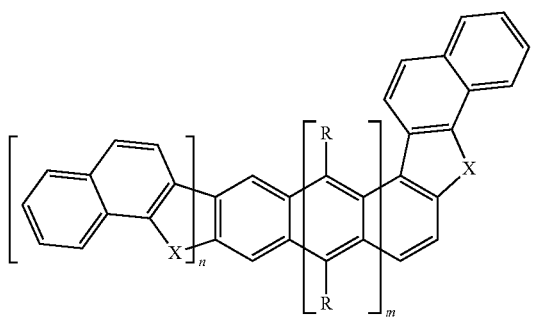

formula (10c)

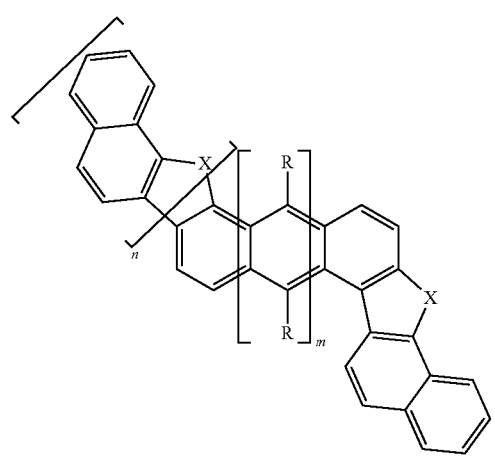

formula (11c)

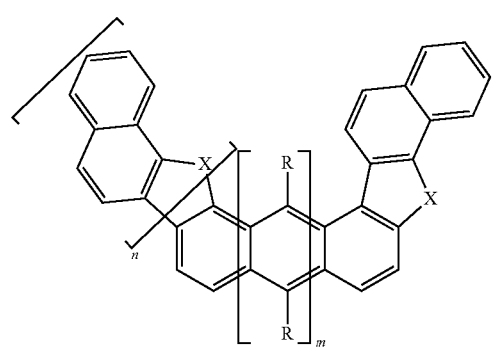

formula (12c)

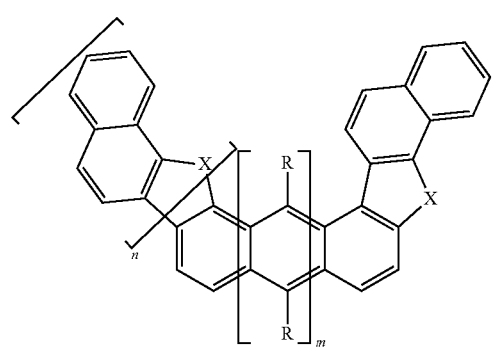

formula (13c)

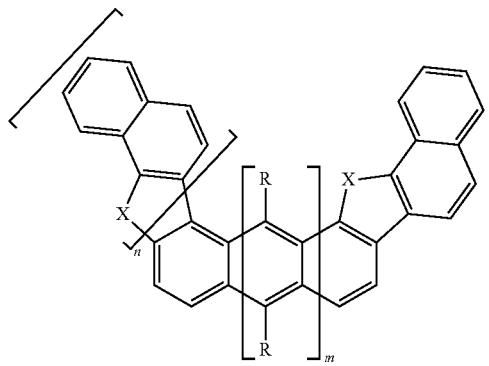

formula (14c)

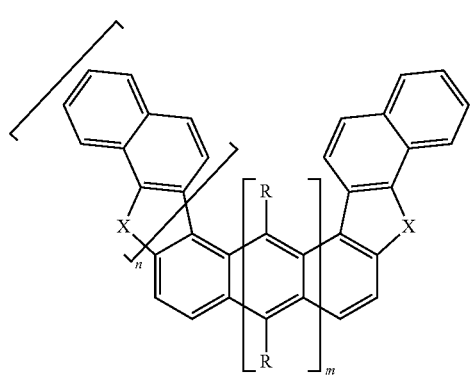

formula (15c)

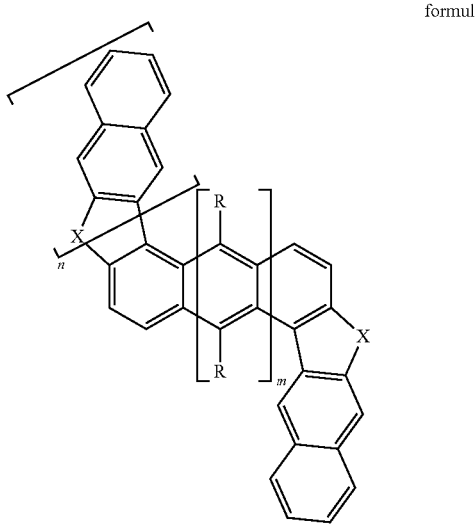

where the symbols and indices have the meanings indicated in claim 1.

6. The compound according to claim 1, wherein the groups Ar are unsubstituted.

7. A process for the preparation of the compound according to claim 1 from a dihaloanthraquinone, comprising the reaction steps of:
a) addition reaction of an arylmetal compound,
b) reduction to the anthracene,
c) coupling to a functionalised aromatic compound, optionally after conversion of the halogen group into a boronic acid derivative, and
d) ring closure.

8. The process according to claim 7, wherein the ring closure is under acidic conditions.

9. A dimer, trimer, tetramer, pentamer, oligomer, polymer or dendrimer comprising one or more of the compounds according to claim 1, where one or more radicals R, $R^1$ or $R^2$ represent bonds between the compounds of the formula (1) or (2) in the dimer, trimer, tetramer or pentamer or bonds from the compound of the formula (1) or (2) to the polymer, oligomer or dendrimer.

10. An electronic device comprising at least one compound according to claim 1.

11. The electronic device according to claim 9, wherein in the devices is selected from the group consisting of organic electroluminescent devices (OLEDs, PLEDs), organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic laser diodes (O-lasers) and organic photoreceptors.

12. An organic electroluminescent device according to claim 10, which comprises an anode, cathode and emitting layer, and further layers selected from in each case one or more hole-injection layers, hole-transport layers, hole-blocking layers, electron-transport layers, electron-injection layers, electron-blocking layers, charge-generation layers and/or further emitting layers, where each of these layers does not necessarily have to be present.

13. The organic electroluminescent device according to claim 11, wherein the compound is employed as host material for fluorescent dopants, as fluorescent dopant, as hole-transport material, as hole-injection material or as electron-transport material.

14. The compound according to claim 1, wherein
$R^1$ is on each occurance, identically or differently, a straight-chain alkyl having 1 to 5 C atoms or a branched or cyclic alkyl, alkoxy or thioalkoxy group having 3 to 5 carbons where one or more non-adjacent $CH_2$ groups is optionally replaced by $R^3C=CR^3$, $C\equiv C$, or —O— and where one or more H atoms is optionally replaced by F, an aryl group having 6 to 16 C atoms or a heteroaryl group having 2 to 16 C atoms, each which may in each case be substituted by one or more radicals $R^2$;

$R^2$ is on each occurrence, identically or differently, H, D, F, Cl, Br, I, CHO, $N(R^3)_2$, $N(Ar^1)_2$, $C(=O)Ar^1$, $P(=O)(Ar^1)_2$, $S(=O)Ar^1$, $S(=O)_2Ar^1$, $CR^3=CR^3Ar^1$, CN, $NO_2$, $Si(R^3)_3$, $B(OR^3)_2$, $OSO_2R^3$, a straight-chain alkyl, alkoxy or thioalkoxy group having 1 to 40 C atoms or a branched or cyclic alkyl, alkenyl, alkynyl, alkoxy or thioalkoxy group having 3 to 40 C atoms, each of which is optionally substituted by one or more radicals $R^3$, where one or more non-adjacent $CH_2$ groups is optionally replaced by $R^3C=CR^3$, $C\equiv C$, $Si(R^3)_2$, $Ge(R^3)_2$, $Sn(R^3)_2$, C=O, C=S, C=Se, $C=NR^2$, $P(=O)(R^3)$, $SO$, $SO_2$, $NR^3$, O, S or $CONR^3$ and where one or more H atoms is optionally replaced by F, Cl, Br, I, CN or $NO_2$, or a combination of these systems; and $R^3$ is on each occurance, identically or differently, H, D, F or an aliphatic, aromatic and/or heteroaromatic hydrocarbon radical having 1 to 20 C atoms, in which, in addition, H atoms is optionally replaced by F.

15. The compound according to claim 1, wherein
m=1 and
n=1.

16. The compound according to claim 1, wherein
m=1,
n=1,
Ar is phenyl and
$R^1$ is phenyl.

* * * * *